US012110292B2

(12) United States Patent
Gray et al.

(10) Patent No.: US 12,110,292 B2
(45) Date of Patent: *Oct. 8, 2024

(54) LIGANDS TO CEREBLON (CRBN)

(71) Applicant: DANA-FARBER CANCER INSTITUTE, INC., Boston, MA (US)

(72) Inventors: Nathanael Gray, Stanford, CA (US); Tinghu Zhang, Brookline, MA (US); Eric Fischer, Chestnut Hill, MA (US); Zhixiang He, Brookline, MA (US); Guangyan Du, Jamaica Plain, MA (US); Katherine Donovan, Boston, MA (US); Radoslaw Nowak, Boston, MA (US); Jing Ting Christine Yuan, Baltimore, MD (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/985,415

(22) Filed: Nov. 11, 2022

(65) Prior Publication Data

US 2023/0312575 A1 Oct. 5, 2023

Related U.S. Application Data

(63) Continuation of application No. 17/255,734, filed as application No. PCT/US2019/039555 on Jun. 27, 2019, now Pat. No. 11,530,219.

(60) Provisional application No. 62/692,167, filed on Jun. 29, 2018.

(51) Int. Cl.
   - C07D 405/14 (2006.01)
   - A61P 35/00 (2006.01)
   - C07D 473/16 (2006.01)
   - C07D 473/34 (2006.01)

(52) U.S. Cl.
   CPC ............ C07D 473/16 (2013.01); A61P 35/00 (2018.01); C07D 405/14 (2013.01); C07D 473/34 (2013.01)

(58) Field of Classification Search
   CPC .................................................. C07D 405/14
   See application file for complete search history.

(56) References Cited

U.S. PATENT DOCUMENTS

| | | |
|---|---|---|
| 10,905,684 B2 | 2/2021 | Chan et al. |
| 11,530,219 B2 * | 12/2022 | Gray .................... C07D 401/04 |
| 2003/0045552 A1 | 3/2003 | Robarge et al. |
| 2005/0143420 A1 | 6/2005 | Moutouh-de ParSeval et al. |
| 2015/0291562 A1 * | 10/2015 | Crew ...................... A61P 7/04 435/375 |

FOREIGN PATENT DOCUMENTS

| | | |
|---|---|---|
| CN | 1968695 A | 5/2007 |
| CN | 101966183 A | 2/2011 |
| CN | 102264720 A | 11/2011 |
| CN | 106660991 A | 5/2017 |
| WO | 02/059106 A1 | 8/2002 |
| WO | 2005110408 A1 | 11/2005 |
| WO | 2010053732 A1 | 5/2010 |
| WO | 2010139266 A1 | 12/2010 |
| WO | 2015/200795 A1 | 12/2015 |
| WO | 2016/007848 A1 | 1/2016 |
| WO | 2017197051 A1 | 11/2017 |
| WO | 2019043214 A1 | 3/2019 |
| WO | 2019140387 A1 | 7/2019 |

OTHER PUBLICATIONS

Luo et al. Cell, 2009, 136, pp. 823-837 (Year: 2009).*
Shi et al. Journal of Immunology Research, vol. 2017, Article ID 9130608, pp. 1-8 (Year: 2017).*
DeNian Ba, Basic Medicine Volume: Molecular Pharmacology, 1st edition, HeilongJiang Science and Technology Press, 1999, pp. 299-302.
CAS No. 1333622-73-3.
CAS No. 1489856-35-0.
El-Zanfally, S. et al. "Derivatives of Glutarimide Likely to Possess Therapeutic Activity", Journal of Pharmaceutical Sciences, 1965, 54(3):467-469.
Yee, Yeung S., et al., "Novel Thalidomide Analogues with Potent NFκB and TNF Expression Inhibition," Med. Chem. Comm., 2011, 2:1-36.
CAS No. 2319109-50-5, 2019.

* cited by examiner

*Primary Examiner* — Matthew P Coughlin
(74) *Attorney, Agent, or Firm* — ArentFox Schiff, LLP; Daniel W. Clarke; Shawn P. Foley

(57) ABSTRACT

Disclosed are compounds with immunomodulatory activity, methods of making the compounds, pharmaceutical compositions containing the compounds, and methods of using the compounds to treat diseases or disorders characterized or mediated by dysfunctional protein activity.

16 Claims, No Drawings

LIGANDS TO CEREBLON (CRBN)

RELATED APPLICATIONS

This application is a continuation of U.S. application Ser. No. 17/255,734, filed on Dec. 23, 2020, which is a national stage application, filed under 35 U.S.C. § 371, of International Application No. PCT/US2019/039555, filed Jun. 27, 2019, which claims the benefit of priority under 35 U.S.C. § 119(e) to U.S. Provisional Application No. 62/692,167, filed on Jun. 29, 2018, each of which is incorporated herein by reference in its entirety.

GOVERNMENT LICENSE RIGHTS

This invention was made with government support under grant number R01CA214608 awarded by the National Institutes of Health. The government has certain rights in the invention.

BACKGROUND OF THE INVENTION

The gene that encodes cereblon (CRBN) was first identified in the course of a study of genes related to memory and learning; the gene was assigned the name CRBN based on its supposed role in the development of cerebral tissues and because its expression in the hippocampus among other areas, is associated with memory and learning processes. Higgins et al., Neurol. 63(10):1927-31 (2004).

Cereblon is a 442-amino acid multifunctional protein located in the cytoplasm, nucleus and peripheral membrane of the human brain and other tissues (Wada et al., Biochem. & Biophys. Res. Comm. 477:388-94 (2016)). It interacts with the DNA damage-binding protein-1 (DDB1), Cullin 4 (Cul4A and Cul4B), and regulator of Cullins 1 (RoC1) to form the functional E3 ubiquitin ligase complex, which is known as the $CRL4^{CRBN}$ E3 ubiquitin ligase complex. Cereblon's role as part of this complex includes targeting proteins for proteolysis (degradation) via a ubiquitin-proteasome pathway. See, e.g., Chang et al., Int. J. Biochem. Mol. Biol. 2(3):287-94 (2011).

Cereblon is closely associated with the metabolism and proliferation of normal cells as well as tumor cells. On one hand, its existence ensures normal metabolic function and normal physiological function of ion channels, which are important to maintaining cell growth and proliferation. On the other hand, cereblon is also involved in the occurrence of many diseases, such as cancer. See, generally, Shi et al., J. Immunol. Res. Article ID 9130608 (2017).

Immunomodulatory drugs ("IMiDs") are a new class of anti-cancer drugs that are derived from thalidomide, a drug which has been approved by the FDA for treatment of multiple myeloma. In addition to thalidomide itself, two such thalidomide analogs, lenalidomide and pomalidomide, have been approved by the FDA (and marketed under the names REVLIMID® and POMALYST®, respectively) for treatment of multiple myeloma (among other diseases). As suggested by their nomenclature, one of the first known properties of IMiDs was their immunomodulatory capacity, including cytokine modulation and T cell co-stimulation (Schafer et al., J. Pharmacol. & Exper. Ther. 305:1222-32 (2003)), resulting in interleukin-2 production in T cells. Subsequently, IMiDs were shown to have pleiotropic effects on a wide range of immune cells including natural killer (NK) cell activation and B cell and monocyte inhibition (Corral et al., J. Immunol. 163:380-6 (1999)). Even more recently, cereblon has been identified as a common primary target for IMiDs.

For example, it has been reported that members of the Ikaros family of transcription factors, Ikaros and Aiolos (encoded by the genes IKZF1 and IKZF3 respectively, are recruited as protein substrates for $CRL4^{CRBN}$ in T cells in response to treatment with lenalidomide and pomalidomide, resulting in enhanced production of IL-2 and other cytokines that regulate T cell function. See, Gandhi et al., Br. J. Hematol. 164:811-21 (2014). It has also been reported that lenalidomide, but not pomalidomide, induces the degradation of the protein kinase casein kinase 1α (CK1α), which exploits CK1α haploinsufficiency associated with 5q-deletion associated myelodysplastic syndrome. Kronke et al., Nature 523:183-8 (2015).

More recently, CRBN-binding compounds named "cereblon modulators" have been developed. For example, CC-122, a new chemical entity termed 'pleiotropic pathway modifier', binds cereblon and promotes degradation of Aiolos and Ikaros in diffuse large B-cell lymphoma (DLBCL) and T cells in vitro, in vivo, and in patients, resulting in both cell autonomous as well as immunostimulatory effects. See, Hagner et al., Blood 126(6):779-89 (2016). CC-885 is another new cereblon modulator. It has been reported that the anti-tumor activity of this drug, which is broader than that of thalidomide, lenalidomide and pomalidomide, is mediated by cereblon-dependent ubiquitination and degradation of the translation termination factor glutathione S-transferase pi gene 1 (GSTP1). See, Matyskiela et al., Nature 535:252-7 (2016).

The exploitation of cereblon as a mediator in disease treatment has also led to the development of hetero-bifunctional PROTACs (PROteolysis TArgeting Chimera) that recruit targeted proteins that are themselves disease mediators (e.g., bronodomnain-containing protein 4 (BRD4)) to $CRL4^{CRBN}$ E3 ubiquitin ligase, leading to degradation of the targeted protein. See, e.g., Lu et al., Cell Cancer Biol. 22(6755~63 (2015).

SUMMARY OF THE INVENTION

A first aspect of the present invention is directed to a compound having a structure represented by formula (I):

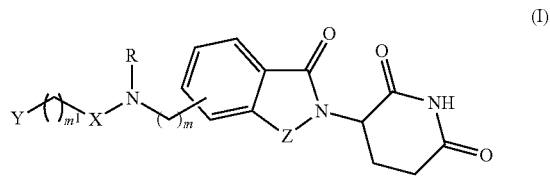

wherein Z is $CH_2$ or C(O); m and $m^1$ are independently an integer from 0-8; R is H or A; X is H or C(O); Y is absent or $NR_1A$ wherein $R_1$ is H or C1-C2 alkyl, and wherein if R is H, then X is C(O), $m^1$ is 1 and Y is $NR_1A$; and if R is A, then X is H, $m^1$ is 0 and Y is absent; and wherein A represents a group selected from (A1)-(A5):

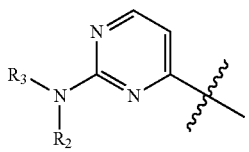
(A1)

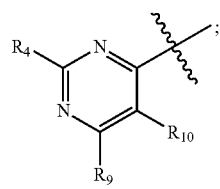
(A5)

wherein $R_2$ is H or C1-C2 alkyl; $R_3$ is optionally substituted C1-C5 alkyl, optionally substituted cyclic (e.g., optionally substituted C6-C14 aryl, optionally substituted C6-C14 heteroaryl, optionally substituted C5-14 carbocyclic and optionally substituted C5-14 heterocyclic), or $R_2$ and $R_3$ together with the N to which they are bound form an optionally substituted heterocyclic group or an optionally substituted heteroaryl group;

wherein $R_4$, $R_9$ and $R_{10}$ are as defined above; or a pharmaceutically acceptable salt or stereoisomer thereof (also referred to herein as "compound/compounds of the present invention").

In some embodiments, m and $m^1$ are independently 0, 1, 2, 3, 4, 5, 6, 7 or 8. In certain embodiments, m and $m^1$ are independently 0, 1, 2, 3, 4, 5 or 6.

In some embodiments, Z is $CH_2$.

Another aspect of the present invention is directed to a pharmaceutical composition that includes a therapeutically effective amount of a compound of the invention, or a pharmaceutically acceptable salt or stereoisomer thereof, and a pharmaceutically acceptable carrier.

A further aspect of the present invention is directed to a method for making a compound of the invention.

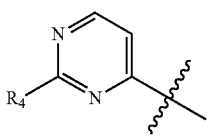
(A2)

wherein $R_4$ represents an optionally substituted cyclic group (e.g., optionally substituted C5-C14 carbocyclic group, an optionally substituted C6-C14 aryl group, an optionally substituted C5-C14 heterocyclic group or an optionally C6-C14 substituted heteroaryl group);

Further aspects of the present invention are directed to methods of treating diseases or disorders involving aberrant activity of a protein that may be a substrate for a complex containing cereblon and the compound, that entails administration of a therapeutically effective amount of a compound of the invention to a subject in need thereof.

Without intending to be bound by any theory of operation, compounds of the present invention exert their therapeutic (e.g., anti-cancer) effects or benefits by a combination of anti-proliferative and immunomodulatory effects. In particular, it is believed that the binding of the compounds to cereblon confers a differentiated substrate specificity on $CRL4^{CRBN}$ E3 ubiquitin ligase. This diversified substrate specificity substantially enlarges the types and numbers of potential targets, thus offering a wide range of therapeutic applications. For example, in addition to, or aside from the expression products of Ikaros family zinc finger protein 1 (IKZF1), and IKZF3, and casein kinase 1 alpha (CK1α), compounds of the present invention may indirectly target a host of different substrates for cereblon-dependent ubiquitination and degradation. Such substrates may include, for example, family with sequence similarity 83 member F (FAM83F), DTW domain containing 1 (DTWD1), IKZF2, IKZF4, IKZF5, zinc finger protein 91 homolog (ZFP91), ZFP62, ZFP36 ring finger protein like (ZFP36L2), ring finger protein 166 (RNF166), Ras-related protein Rab-28 (RAB28), glutathione S-transferase pi 1 (GSTP1), GSPT2, mitochondrial import inner membrane translocase subunit Tim10 (TIMM10), GDNF inducible zinc finger protein 1 (GZF1), early growth response 1 (EGR1), hyper-methylated in cancer 1 (HIC1), HIC2, insulinoma-associated protein 2 (INSM2), odd-skipped related transcription factor 2 (OSR2), protein polybromo-1 (PB1), PR domain zinc finger protein 15 (PRD15), spalt like transcription factor 1 (SALL1), SALL3, SALL4, WIZ, zinc finger and BTB domain-containing protein 17 (ZBT17), ZBTB39, ZBT41, ZBT49, ZBT7A, ZBT7B, ZBTB2, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483, SNF517, ZNF526, ZNF581, ZNF587, ZNF589, ZNF618, ZNF644, ZNF646,

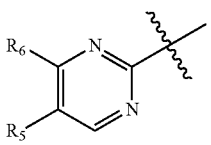
(A3)

wherein $R_5$ represents hydrogen or halo (F, Cl, Br, or I) and $R_6$ represents $NR_7R_8$ wherein $R_7$ represents H and $R_8$ represents an optionally substituted C6-C14 aryl group;

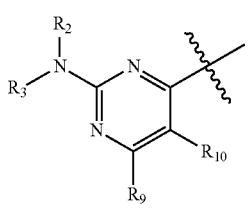
(A4)

wherein $R_2$ and $R_3$ are as defined above, and $R_9$ and $R_{10}$ each represents H or each independently represents C or N provided that at least one of $R_9$ and $R_{10}$ represents N and together with the atoms to which they are bound form an optionally substituted C5-C6 heterocyclic group such as optionally substituted membered C6 heteroaryl group; or ZNF653, ZN6F54, ZNF692, ZNF724, ZNF771, ZNF782, ZNF784, ZNF814, zinc finger and SCAN domain containing 10 (ZSC10), ZSC22, ZC827, and zinc finger with UFM1-specific peptidase domain (ZUFSP).

Also provided are methods of treating a disease or disorder characterized or mediated by aberrant activity of a protein selected from the group consisting of casein kinase 1 alpha (CK1α), family with sequence similarity 83 member F (FAM83F), DTW domain containing 1 (DTWD1), zinc finger protein 91 homolog (ZFP91), ZFP62, ZFP36 ring finger protein like (ZFP36L2), ring finger protein 166 (RNF166), Ikaros family zinc finger protein 1 (IKZF1), IKZF2, IKZF3, IKZF4, IKZF5, Ras-related protein Rab-28 (RAB28), glutathione S-transferase pi 1 (GSTP1), GSPT2, mitochondrial import inner membrane translocase subunit Tim10 (TIMM10), GDNF inducible zinc finger protein 1 (GZF1), early growth response 1 (EGR1), hypermethylated in cancer 1 (HIC1), HIC2, insulinoma-associated protein 2 (INSM2), odd-skipped related transcription factor 2 (OSR2), protein polybromo-1 (PB1), PR domain zinc finger protein 15 (PRD15), spalt like transcription factor 1 (SALL1), SALL3, SALL4, WIZ, zinc finger and BTB domain-containing protein 17 (ZBT17), ZBT41, ZBT49, ZBT7A, ZBT7B, ZBTB2, ZBTB39, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483, SNF517, ZNF526, ZNF581, ZNF587, ZNF589, ZNF618, ZNF644, ZNF646, ZNF653, ZNF654, ZNF692, ZNF724, ZNF771, ZNF782, ZNF784, ZNF814, zinc finger and SCAN domain containing 10 (ZSC10), ZSC22, ZC827, and zinc finger with UFM1-specific peptidase domain (ZUFSP), comprising administering a therapeutically effective amount of the compound of Formula I, or a pharmaceutically acceptable salt or stereoisomer thereof, to a subject in need thereof.

In some embodiments, the disease or disorder is characterized or mediated by aberrant activity of IKZF2.

One advantage of the present invention is that the compounds may provide an effective therapy in cases where the targets might not be otherwise "druggable" in terms of being directly targeted by any current generation IMiDs. The inventive compounds may also be advantageous relative to the cereblon-targeted PROTACS which due to their large flexible linkers can cause pharmacokinetic challenges.

DETAILED DESCRIPTION

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a" "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The term "aberrant" as used herein refers to activity that differs from normal activity of the protein in a non-pathological state. Such aberrant activity might be dysfunctional or dysregulated. Thus, the term aberrant may refer to activity or function of a protein that is greater or less relative to a normal healthy subject.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group.

In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a C2-C12, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is C2-C12, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "ester" is represented by the formula $OC(O)Z^1$ or $C(O)OZ^1$, where $Z^1$ may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula $ZiOZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ketone" is represented by the formula $Z^1C(O)Z^2$, where $A^1$ and $A^2$ independently represent alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonyl" refers to the sulfo-oxo group represented by the formula —$S(O)_2Z^1$, where $Z^1$ may be hydrogen, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonylamino" (or "sulfonamide") is represented by the formula —$S(O)_2NH_2$.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocyclyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, isoindolyl, benzothienyl, benzofuranyl, dibenzofuranyl, indazolyl, benzimidazolyl, benzothiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, where $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl, alkoxy, substituted alkoxy, alkenyl, substituted alkenyl, alkynyl, substituted alkynyl, cyclic, substituted cyclic, carbocyclic, substituted carbocyclic, heterocyclic, substituted heterocyclic, aryl (e.g., benzyl and phenyl), substituted aryl (e.g., substituted benzyl or phenyl), heteroaryl, substituted heteroaryl, aralkyl, substituted aralkyl, halo, hydroxyl, aryloxy, substituted aryloxy, alkylthio, substituted alkylthio, arylthio, substituted arylthio, cyano, carbonyl, substituted carbonyl, carboxyl, substituted carboxyl, amino, substituted amino, amido, substituted amido, sulfonyl, substituted sulfonyl, amino acid, and peptide groups.

Broadly, compounds of the present invention have a structure represented by formula (I):

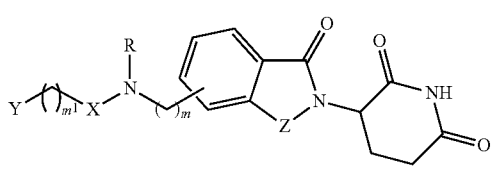

(I)

wherein Z is $CH_2$ or C(O); m and $m^1$ are independently an integer from 0-8; R is H or A; X is H or C(O); Y is absent or $NR_1A$ wherein $R_1$ is H or C1-C2 alkyl, and wherein if R is H, then X is C(O), $m^1$ is 1 and Y is $NR_1A$; and if R is A, then X is H, $m^1$ is 0 and Y is absent; and wherein A represents

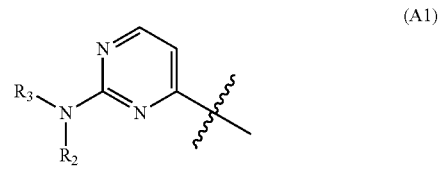

(A1)

wherein $R_2$ is H or C1-C2 alkyl; $R_3$ is optionally substituted C1-C5 alkyl, optionally substituted C6-C14 aryl, optionally substituted C6-C14 heteroaryl, optionally substituted C5-C14 carbocyclic or optionally substituted C5-C14 heterocyclic, or $R_2$ and $R_3$ together with the N to which they are bound form an optionally substituted C6-C14 heterocyclic group or an optionally substituted C6-C14 heteroaryl group;

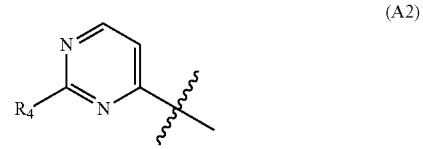

(A2)

wherein $R_4$ represents an optionally substituted cyclic group, e.g., an optionally substituted C5-C14 carbocyclic group, an optionally substituted C6-C14 aryl group, an optionally substituted C5-C14 heterocyclic group or an optionally substituted C6-C14 heteroaryl group;

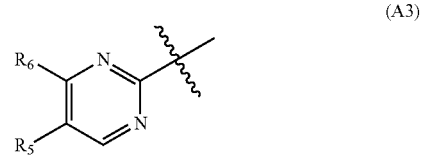

(A3)

wherein $R_5$ represents hydrogen or halo and $R_6$ represents $NR_7R_8$ wherein $R_7$ represents H and $R_8$ represents an optionally substituted C6-C14 aryl group;

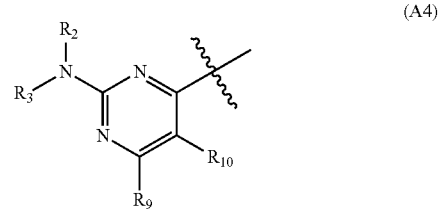

(A4)

wherein $R_2$ and $R_3$ are as defined above, and $R_9$ and $R_{10}$ each represents H or each independently represents C or N provided that at least one of $R_9$ and $R_{10}$ represents N and together with the atoms to which they are bound form an optionally substituted C5-C6 heterocyclic group such as optionally substituted C6 heteroaryl group; or

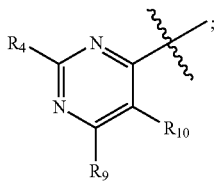

(A5)

wherein $R_4$, $R_9$ and $R_{10}$ are as defined above, or a pharmaceutically acceptable salt or stereoisomer thereof.

In some embodiments, m and $m^1$ are independently 0, 1, 2, 3, 4, 5, 6, 7 or 8. In certain embodiments, m and $m^1$ are independently 0, 1, 2, 3, 4, 5 or 6.

In some embodiments, wherein m is 0, R is H, X is C(O), $m^1$ is 1, Y is $NR_1A$ and $R_1$ is H, the compounds of formula (I) have a structure represented by formula (Ia):

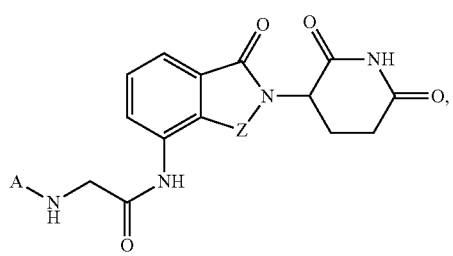

(Ia)

wherein A and Z are as defined above, or a pharmaceutically acceptable salt or stereoisomer thereof.

In some embodiments, wherein A is represented by A1, the compounds of formula (Ia) have a structure represented by formula (Ia1):

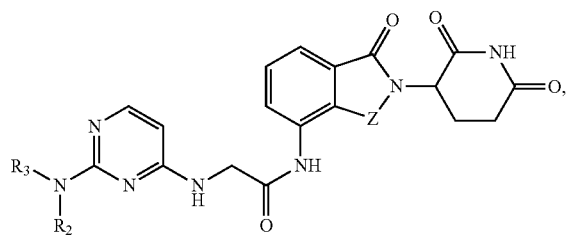

(Ia1)

wherein $R_2$ and $R_3$ are as defined above, or a pharmaceutically acceptable salt or stereoisomer thereof.

In some embodiments, wherein $R_3$ represents aryl (e.g., phenyl) or substituted aryl (e.g., substituted phenyl), the compounds of formula (Ia1) have a structure represented by formula (Ia1a):

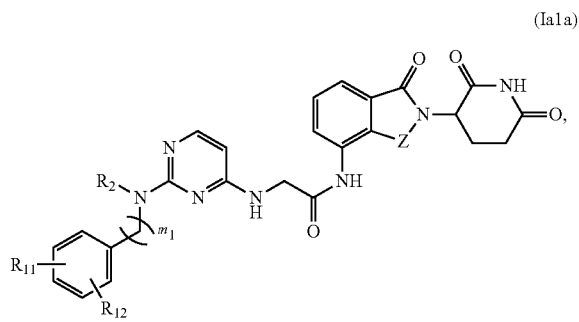

(Ia1a)

wherein $m_1$ is 0 or 1, and $R_{11}$ and $R_{12}$ independently represent H, halo, $CF_3$, or C1-C2 alkoxy, or wherein $R_{11}$ and $R_{12}$ each independently represents C or a heteroatom (e.g., O, N or S) and together with the atoms to which they are bound form an optionally substituted cyclic group, e.g., C5-C14 carbocyclic, C5-C14 heterocyclic, C6-C14 aryl or C6-C14 heteroaryl group (but consistent with use of the term "aryl", the overall ring structure is defined as an optionally substituted aryl group), or a pharmaceutically acceptable salt or stereoisomer thereof.

In some embodiments, wherein $R_3$ represents an optionally substituted heterocyclic group, the compound of formula (Ia1) has a structure represented by formula (Ia1b):

(Ia1b)

wherein $R_2$ is as defined above and $R_{13}$ represents H or optionally substituted C1-C5 alkyl, optionally substituted C6-C14 aryl, optionally substituted C6-C14 heteroaryl, optionally substituted C5-C14 carbocyclic or optionally substituted C5-C14 heterocyclic, or a pharmaceutically acceptable salt or stereoisomer thereof.

In some embodiments, when m is 0 and $R_2$ and $R_3$ together with the atoms to which they are bound form an optionally C5-C14 heterocyclic such as an optionally substituted C6-C14 heteroaryl group, the compound of formula (Ia1) has a structure represented by formula (Ia1c):

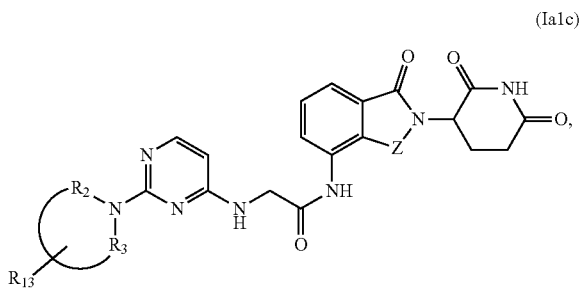

(Ia1c)

wherein $R_{13}$ is as defined above, or a pharmaceutically acceptable salt or stereoisomer thereof.

In some embodiments, wherein A is represented by A2, the compound of formula (Ia) has a structure as represented by formula (Ia2):

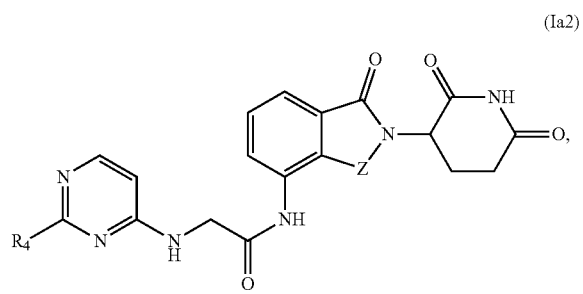

(Ia2)

wherein $R_4$ is as defined above, or a pharmaceutically acceptable salt or stereoisomer thereof.

In some embodiments, wherein m and $m^1$ are 0, X is H, Y is absent and R is A, the compound of formula (I) has a structure as represented by formula (Ib):

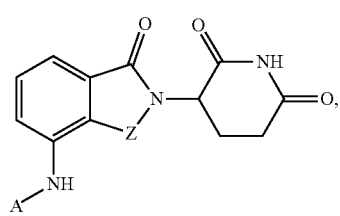

(Ib)

or a pharmaceutically acceptable salt or stereoisomer thereof.

In some embodiments, wherein A is represented by A1, the compound of formula (Ib) has a structure as represented by formula (Ib1):

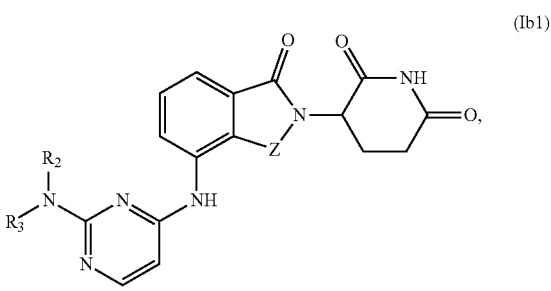

(Ib1)

wherein $R_2$ and $R_3$ are as defined above, or a pharmaceutically acceptable salt or stereoisomer thereof.

In some embodiments, when $R_3$ is an optionally substituted aryl (e.g., phenyl), the compound of formula (Ib1) has a structure represented by formula (Ib1α):

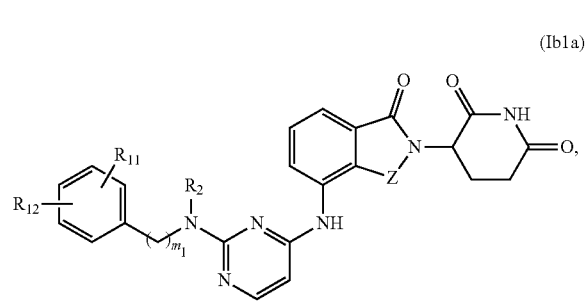

(Ib1a)

wherein $m_1$ is 0 or 1 and $R_2$, $R_{11}$ and $R_{12}$ are as defined above, or a pharmaceutically acceptable salt or stereoisomer thereof.

In some embodiments, the compound of formula (Ib1) has a structure represented by formula (Ib1b):

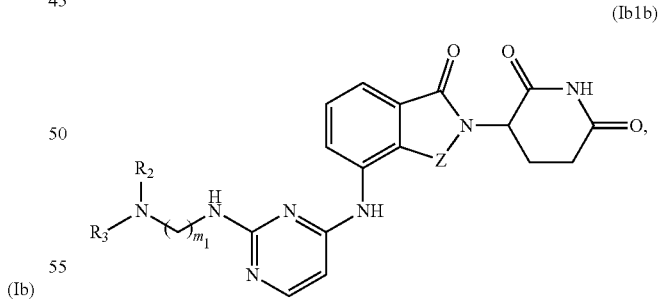

(Ib1b)

wherein $m_1$ is 0 or 1, $R_2$ is as defined above and $R_3$ represents an optionally substituted C5-C14 heterocyclic group, or a pharmaceutically acceptable salt or stereoisomer thereof.

In some embodiments, wherein $R_2$ and $R_3$ together with the atoms to which they are bound form an optionally substituted heterocyclic group such as an optionally substituted heteroaryl group, the compound of formula (Ib1) has a structure represented by formula (Ib1c):

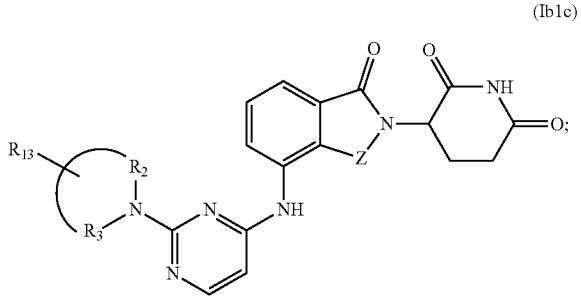

(Ib1c)

wherein R$_{13}$ is as defined above, or a pharmaceutically acceptable salt or stereoisomer thereof.

In some embodiments, wherein A is represented by A2, the compound of formula (Ib) has a structure as represented by formula (Ib2):

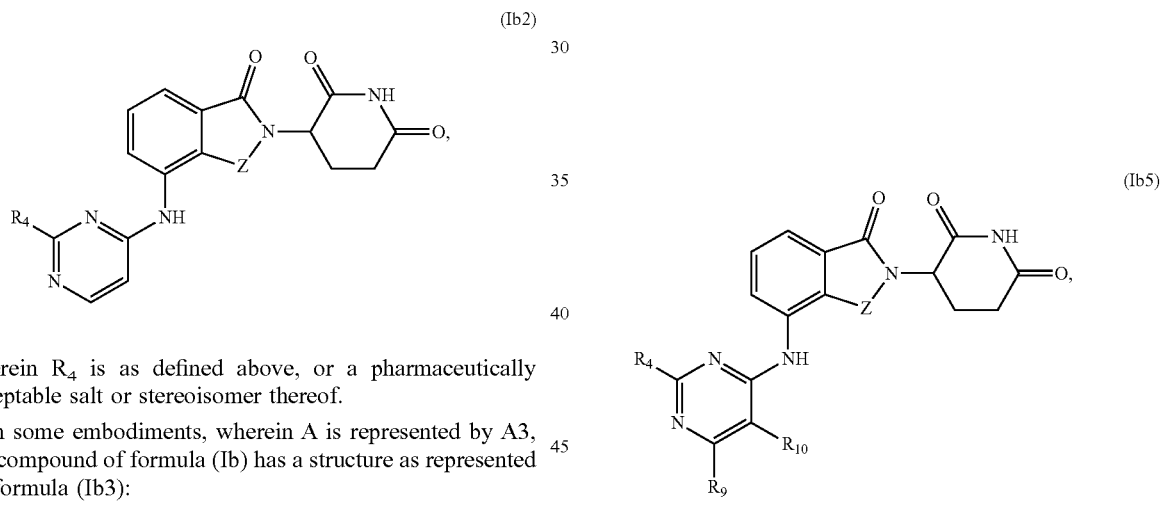

(Ib2)

wherein R$_4$ is as defined above, or a pharmaceutically acceptable salt or stereoisomer thereof.

In some embodiments, wherein A is represented by A3, the compound of formula (Ib) has a structure as represented by formula (Ib3):

(Ib3)

wherein R$_5$ and R$_6$ are as defined above, or a pharmaceutically acceptable salt or stereoisomer thereof.

In some embodiments, wherein A is represented by A4, the compound of formula (Ib) has a structure as represented by formula (Ib4):

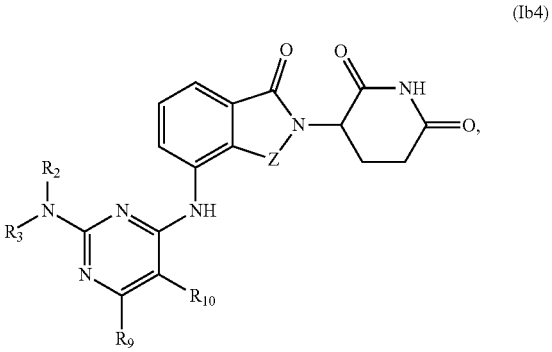

(Ib4)

wherein R$_2$, R$_3$, R$_9$ and R$_{10}$ are as defined above, or a pharmaceutically acceptable salt or stereoisomer thereof.

In some embodiments, wherein A is represented by A5, the compound of formula (Ib) has a structure as represented by formula (Ib5):

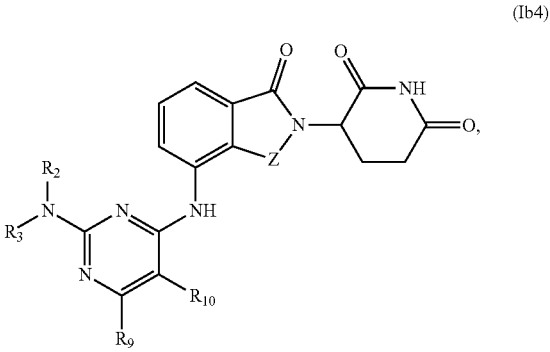

(Ib5)

wherein R$_4$, R$_9$ and R$_{10}$ are as defined above, or a pharmaceutically acceptable salt or stereoisomer thereof.

In some embodiments, wherein X is H, m$^1$ is 0, R is A and Y is absent, the compound of formula (I) has a structure as represented by formula (Ic):

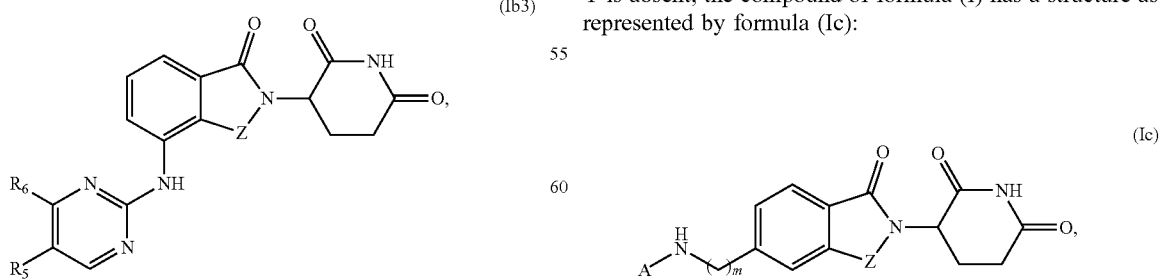

(Ic)

or a pharmaceutically acceptable salt or stereoisomer thereof.

In some embodiments, wherein A is represented by A3, the compound of formula (Ic) has a structure as represented by formula (Ic1):

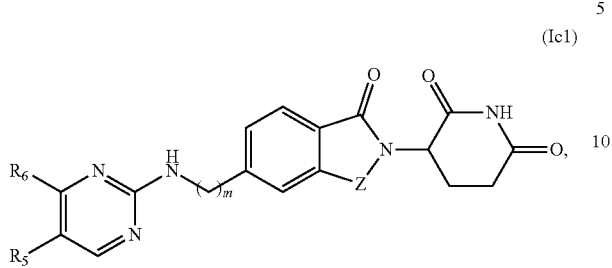

(Ic1)

wherein $R_5$ and $R_6$ are as defined above, or a pharmaceutically acceptable salt or stereoisomer thereof.

With respect to the compounds of the present invention, representative examples of $R_3$, $R_4$ and $R_5$ are as follows:

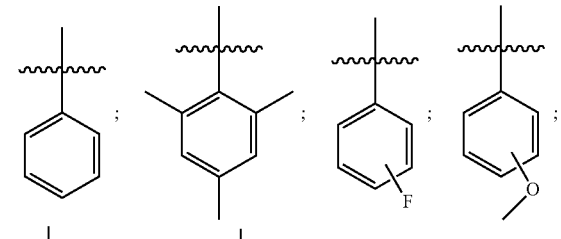

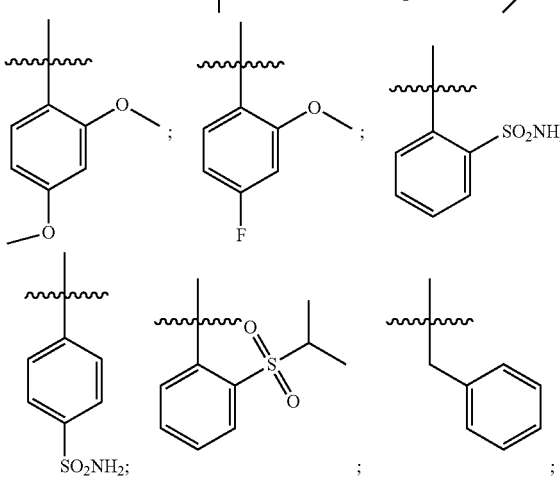

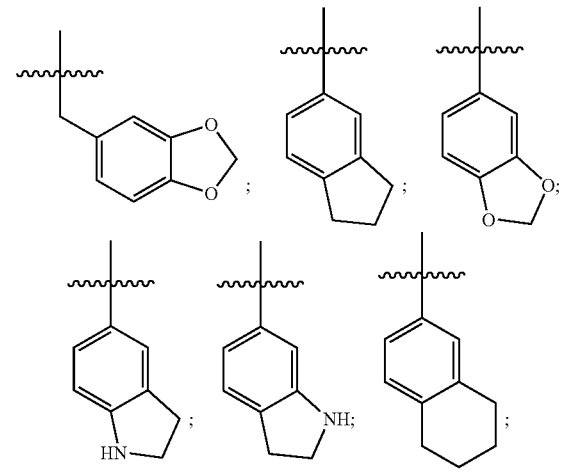

-continued

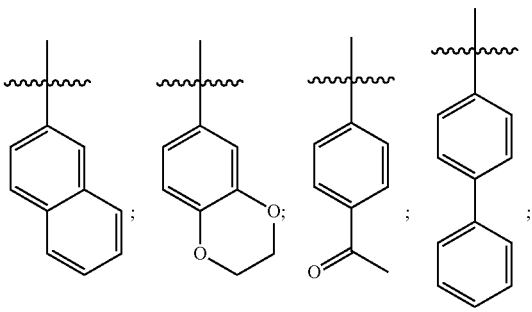

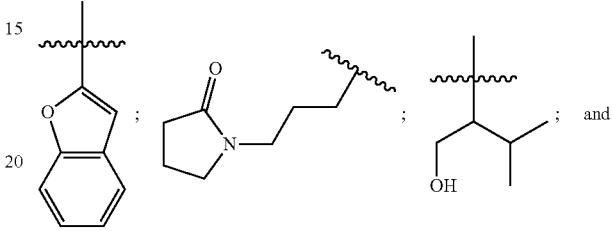

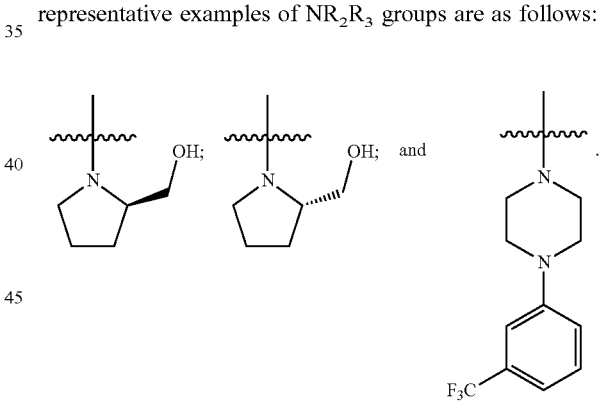

With respect to the compounds of the present invention, representative examples of $NR_2R_3$ groups are as follows:

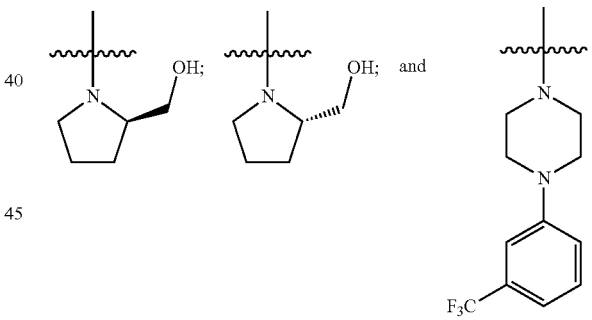

With respect to the compounds of the present invention, representative examples of optionally substituted C5-C6 heterocyclic groups formed by $R_9$ and $R_{10}$ are as follows:

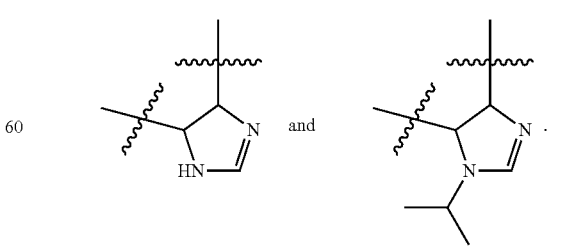

In some embodiments, Z is $CH_2$.

In some embodiments, compounds of the present invention are as follows:
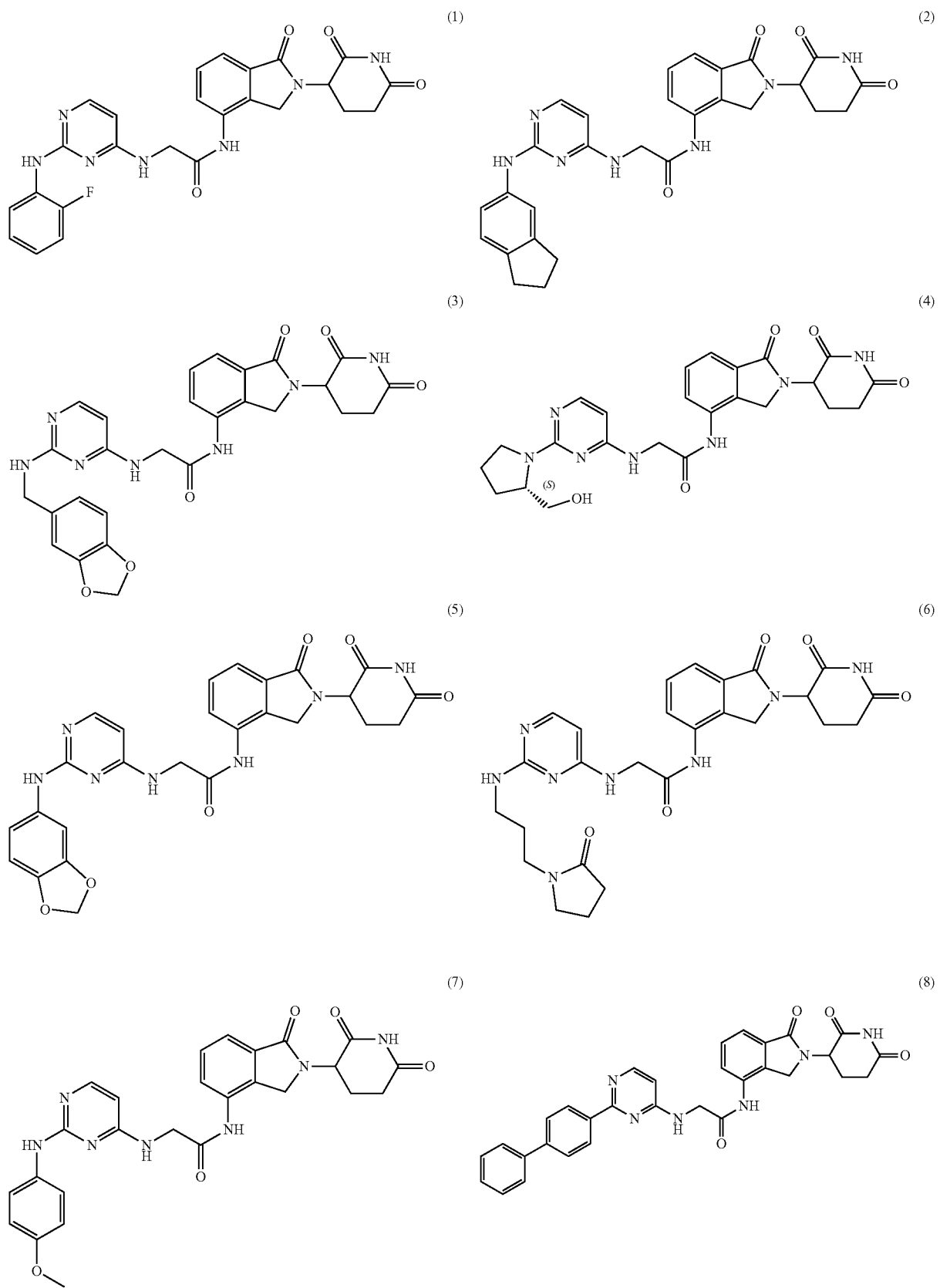

-continued
(9)
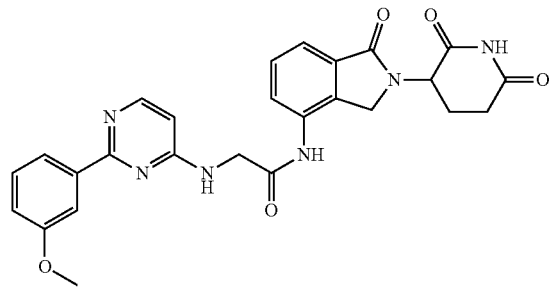
(10)
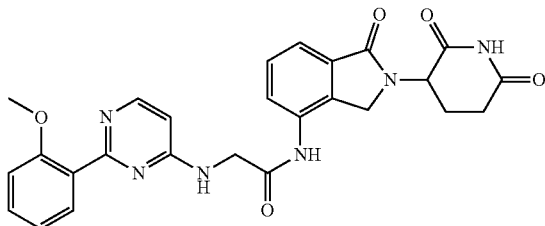
(11)
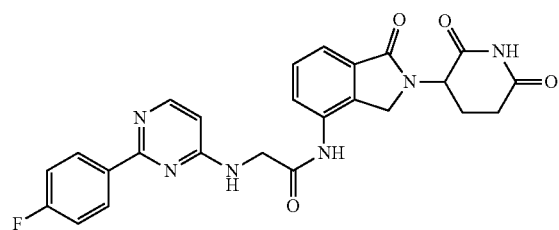
(12)
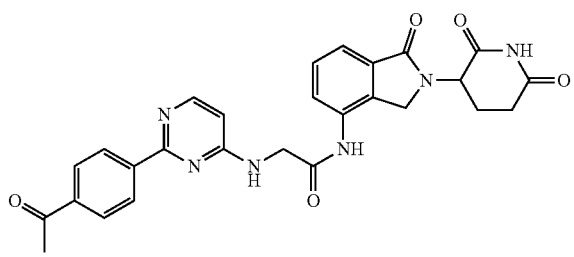
(13)
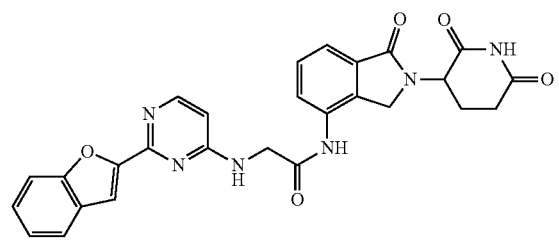
(14)
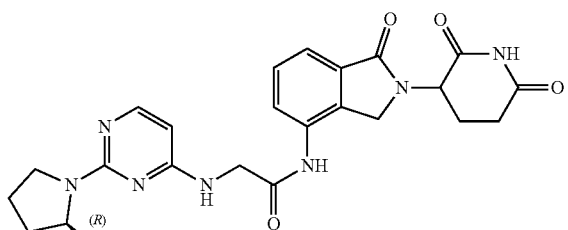
(15)
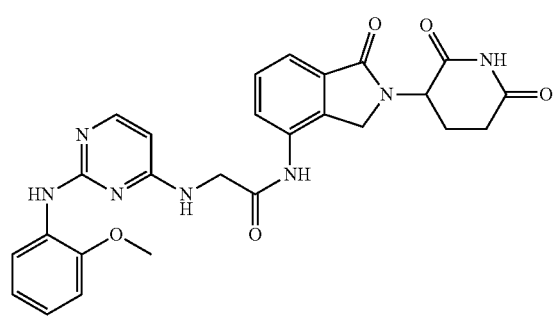
(16)
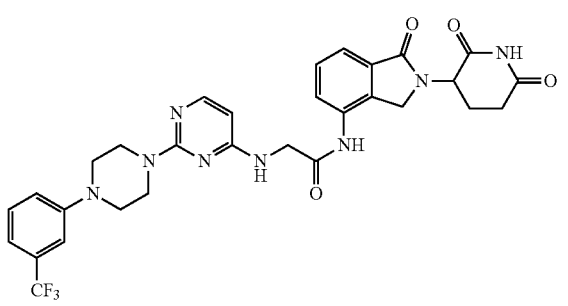
(17)
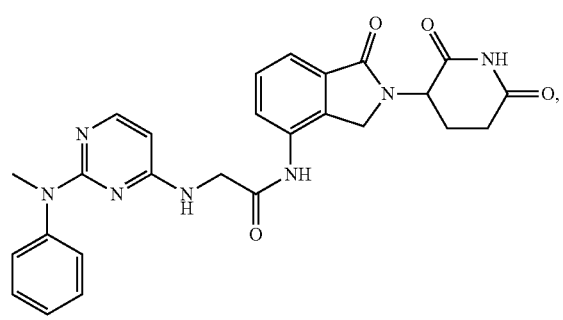
(18)
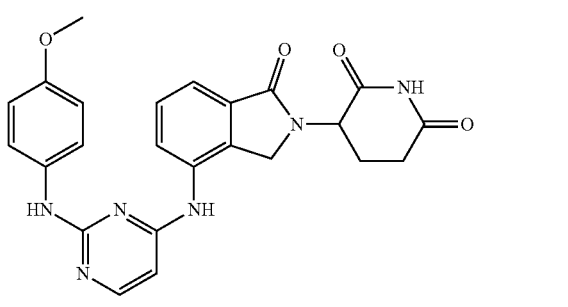

-continued
(19)
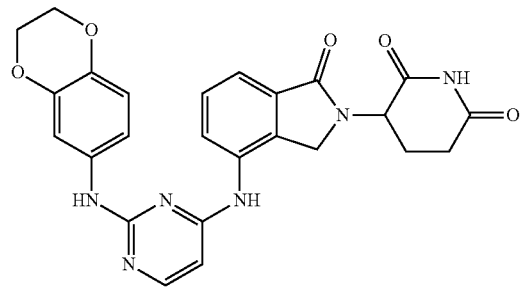
(20)
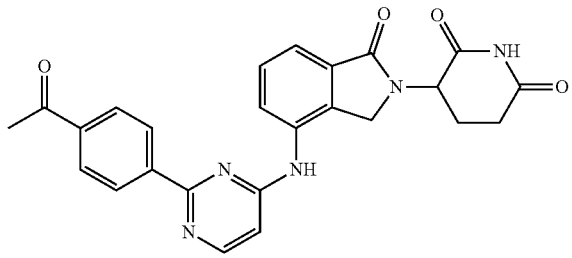
(21)
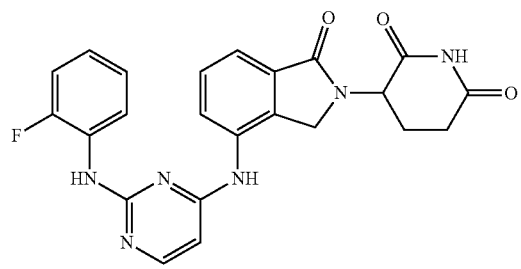
(22)
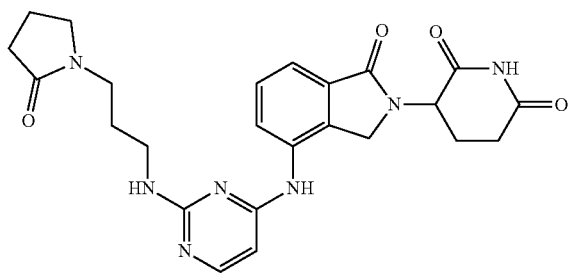
(23)
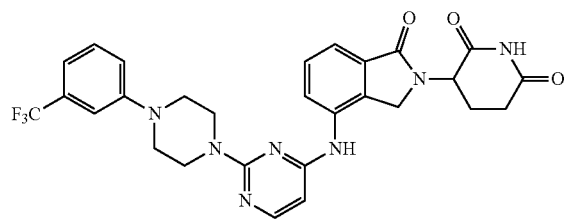
(24)
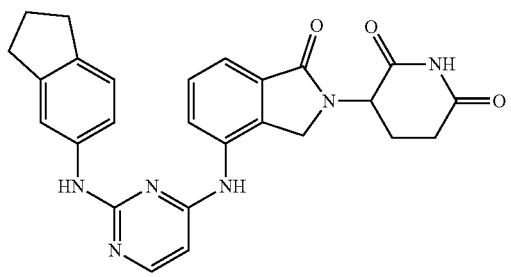
(25)
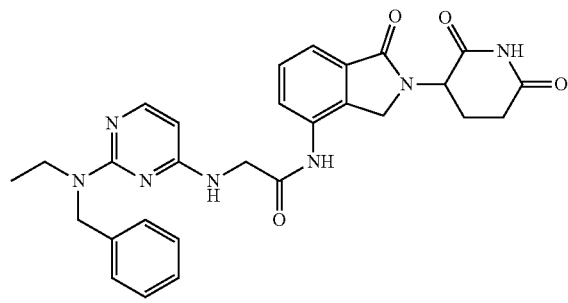
(26)
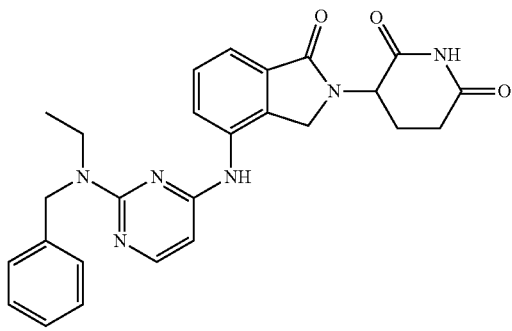
(27)
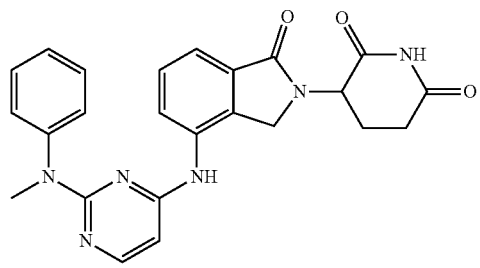
(28)
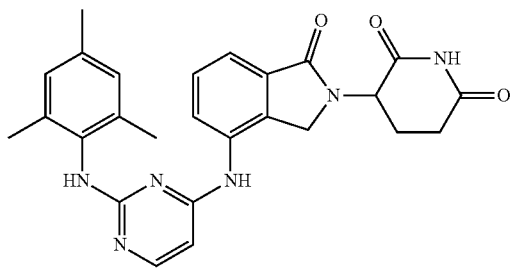

-continued
(29)
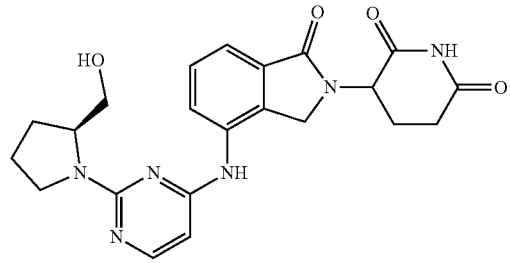
(30)
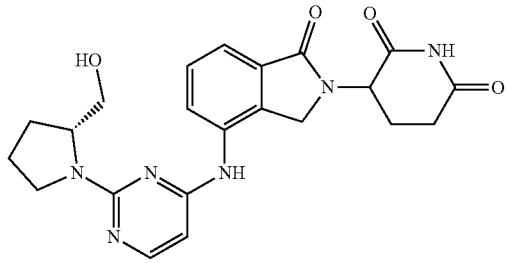
(31)
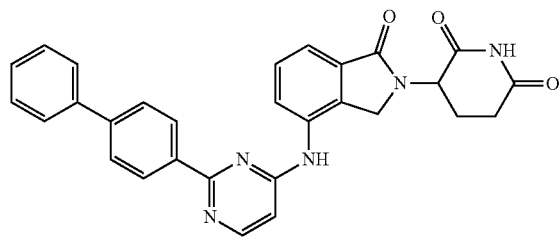
(32)
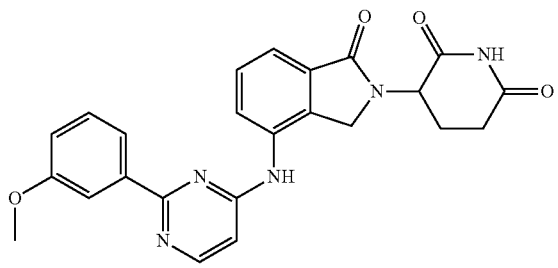
(33)
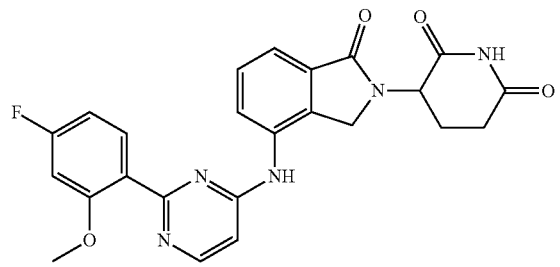
(34)
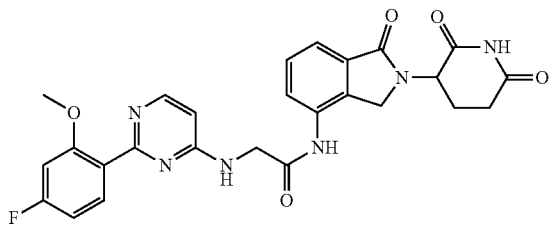
(35)
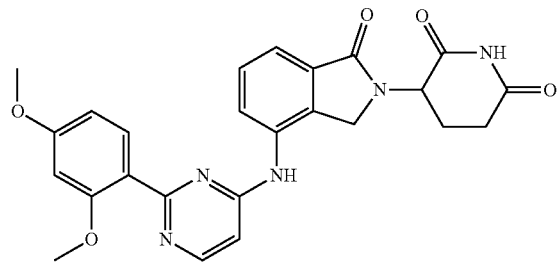
(36)
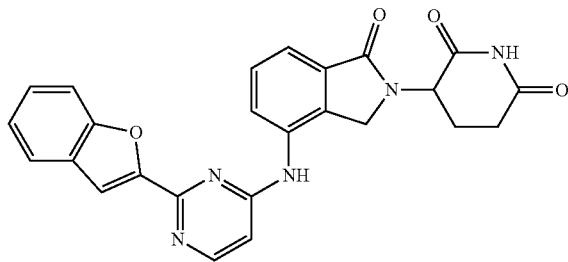
(37)
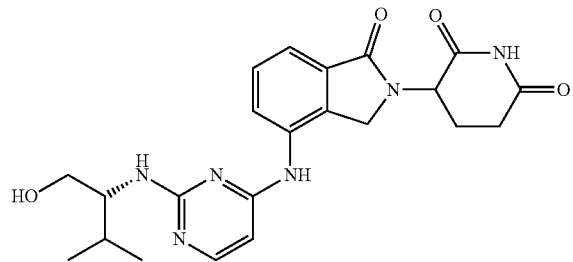
(38)
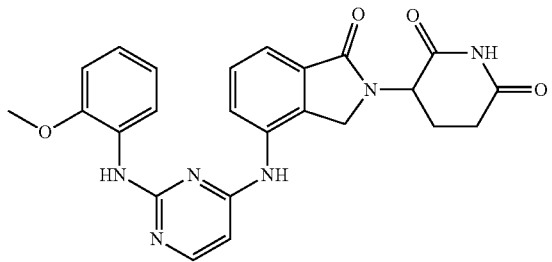

-continued
(39)
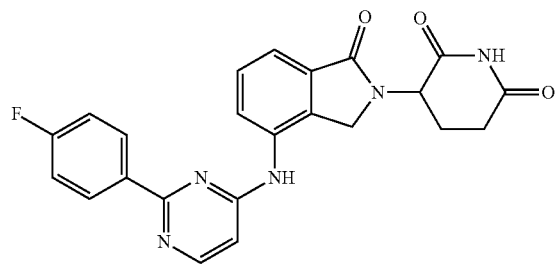
(40)
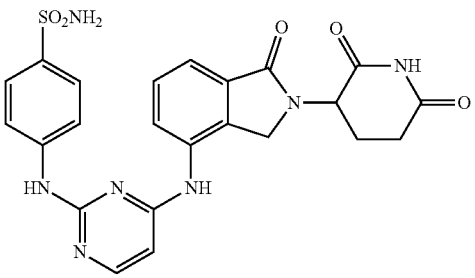
(41)
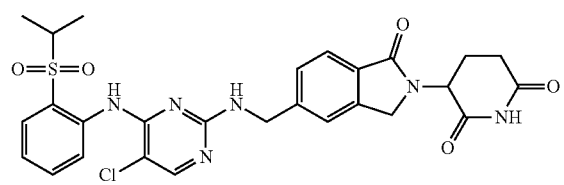
(42)
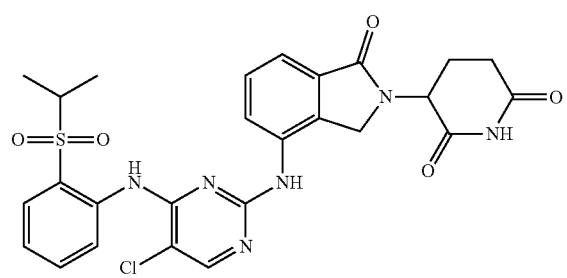
(43)
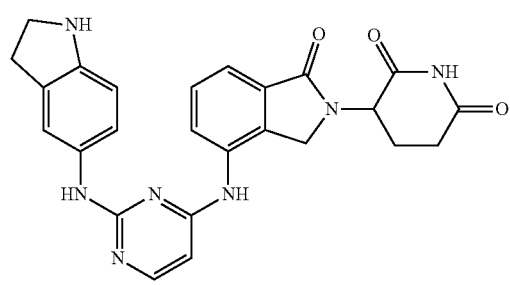
(44)
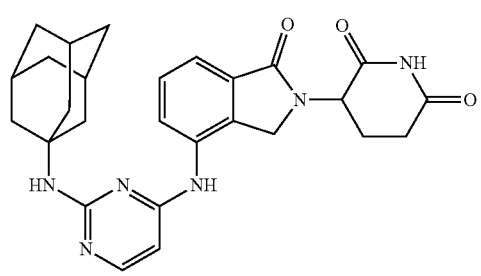
(45)
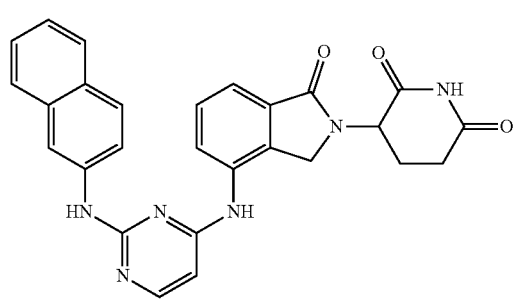
(46)
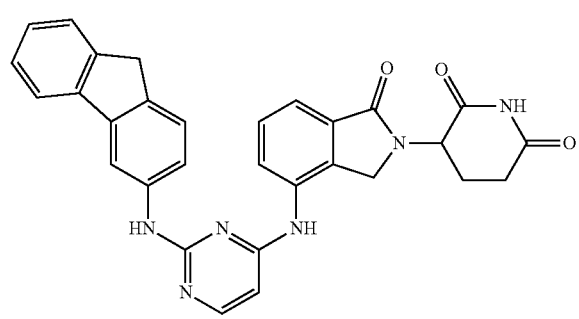
(47)
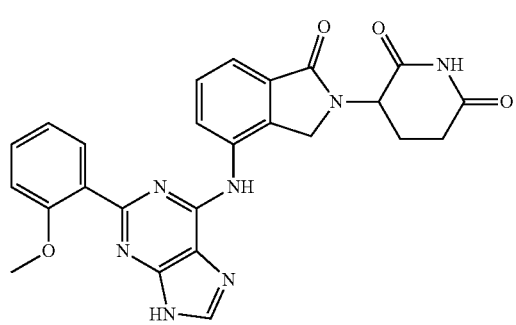
(48)
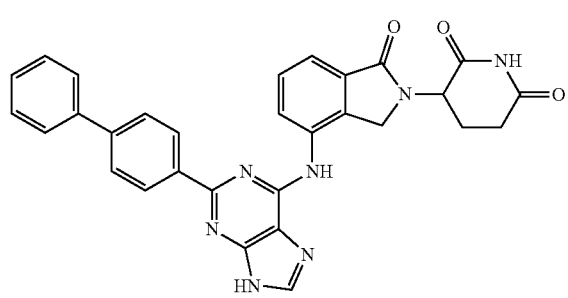

-continued
(49)
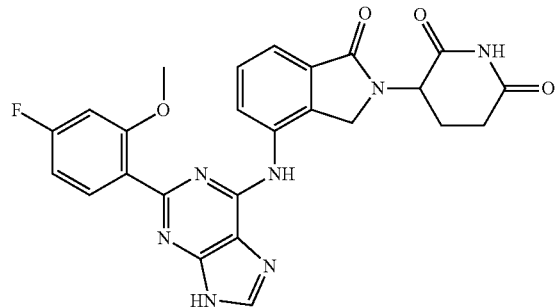
(50)
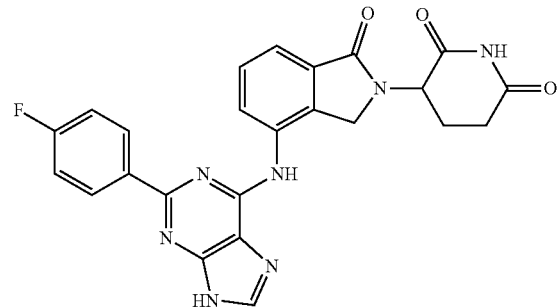
(51)
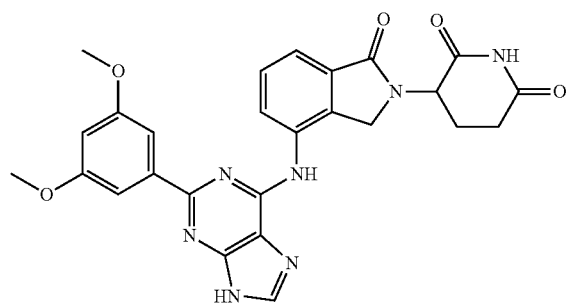
(52)
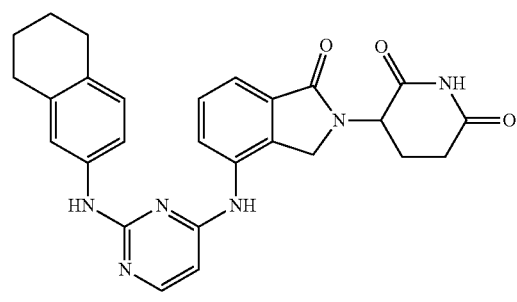
(53)
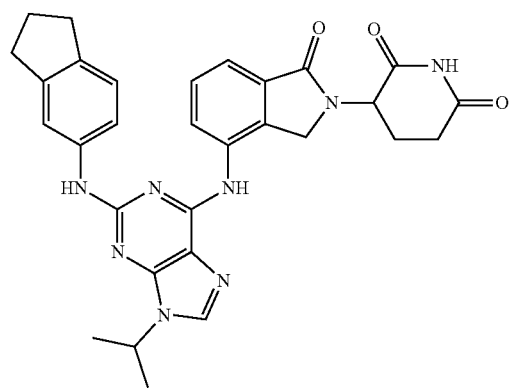
(54)
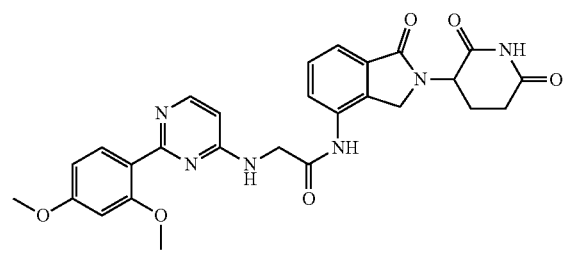
(55)
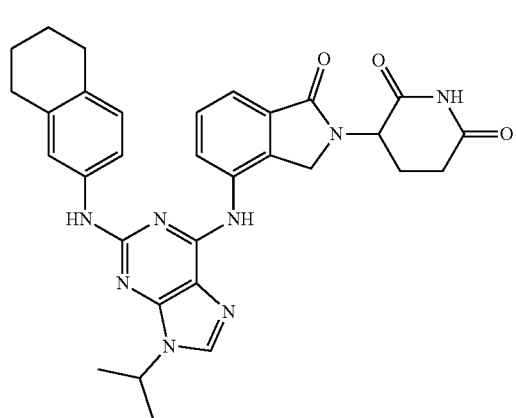
(56)
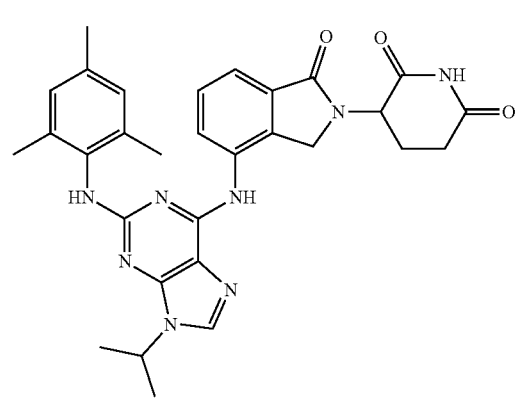

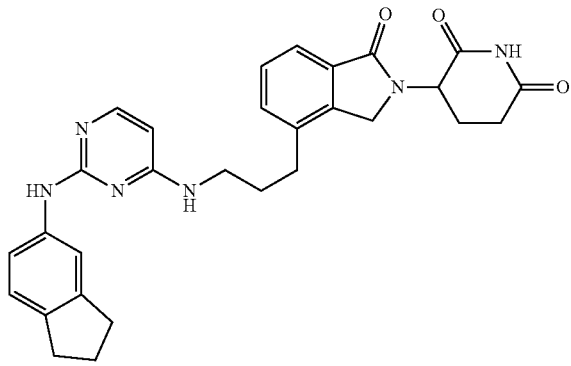

(57)

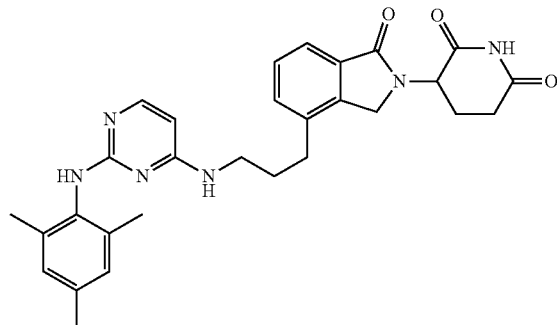

(58)

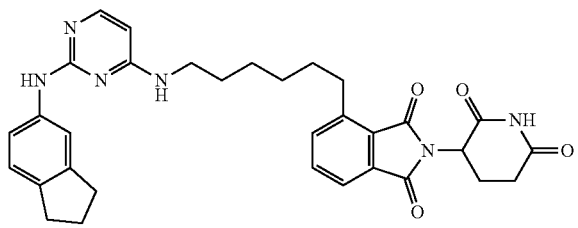

(59)

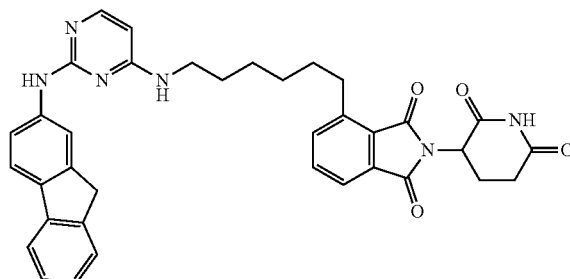

(60)

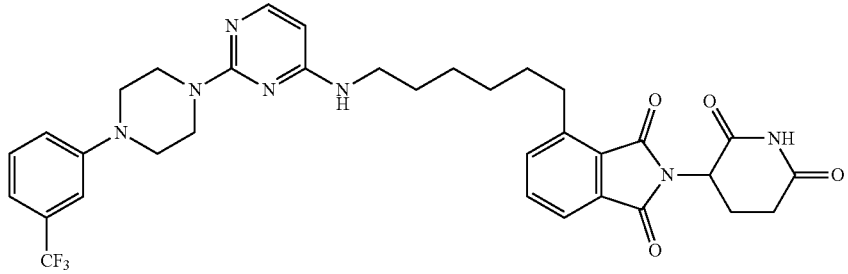

(61)

or a pharmaceutically acceptable salt or stereoisomer thereof.

Compounds of the present application may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, a compound of the present invention is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances.

Compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/ trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present application may be made and used in the form of individual isomers and substantially free of other isomers, or in the form of a mixture of various isomers, e.g., racemic mixtures of stereoisomers.

In addition, the compounds of the present invention embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In another aspect, the present invention is directed to a method for making a compound of the present invention, or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate nonlimiting methods by which the compounds of the invention may be prepared.

Pharmaceutical Compositions

Another aspect of the present invention is directed to a pharmaceutical composition that includes a therapeutically effective amount of a compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, compounds of the present invention may be formulated into a given type of composition in accordance with conventional pharmaceutical practice such as conventional mixing, dissolving, granulating, dragee-making, levigating, emulsifying, encapsulating, entrapping and compression processes (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compositions are formulated for oral or intravenous administration (e.g., systemic intravenous injection).

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of present invention may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The inventive compounds may be formulated for buccal or sublingual administration, examples of which include tablets, lozenges and gels.

The compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of the present invention may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated 1 as to their effectiveness in enhance ng the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound of the present invention or a pharmaceutically acceptable salt or a stereoisomer thereof that is effective in producing the desired therapeutic response in a particular patient suffering from a disease or disorder characterized or mediated by aberrant activity of a protein selected from the group consisting of casein kinase 1 alpha (CK1α), family with sequence similarity 83 member F (FAM83F), DTW domain containing 1 (DTWD1), zinc finger protein 91 homolog (ZFP91), ZFP62, ZFP36 ring finger protein like (ZFP36L2), ring finger protein 166 (RNF166), Ikaros family zinc finger protein 1 (IKZF1), IKZF2, IKZF3, IKZF4, IKZF5, Ras-related protein Rab-28 (RAB28), glutathione S-transferase pi 1 (GSTP1), GSPT2, mitochondrial import inner membrane translocase subunit Tim10 (TIMM10), GDNF inducible zinc finger protein 1 (GZF1), early growth response 1 (EGR1)-, hypermethylated in cancer 1 (HIC1)-, HIC2-, insulinoma-associated protein 2 (INSM2)-, odd-skipped related transcription factor 2 (OSR2), protein polybromo-1 (PB1), PR domain zinc finger protein 15 (PRD15), spalt like transcription factor 1 (SALL1), SALL3, SALL4, WIZ, zinc finger and BTB domain-containing protein 17 (ZBT17), ZBT41, ZBT49, ZBT7A, ZBT7B, ZBTB2, ZBTB39, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483, SNF517, ZNF526, ZNF581, ZNF587, ZNF589, ZNF618, ZNF644, ZNF646, ZNF653, ZNF654, ZNF692, ZNF724, ZNF771, ZNF782, ZNF784, ZNF814, zinc finger and SCAN domain containing 10 (ZSC10), ZSC22, ZC827, and zinc finger with UFM1-specific peptidase domain (ZUFSP).

In some embodiments, the disease or disorder is characterized or mediated by aberrant activity of IKZF2. The term "therapeutically effective amount" includes the amount of the compound of the present invention or a pharmaceutically acceptable salt or a stereoisomer thereof, that when administered, induces a positive modification in the disease or disorder to be treated (e.g., remission), or is sufficient to prevent development or progression of the disease or disorder, or alleviate to some extent, one or more of the symptoms of the disease or disorder being treated in a subject, or which simply kills or inhibits the growth of diseased (e.g., cancer) cells.

The total daily dosage of the compounds of present invention and usage thereof may be decided in accordance with standard medical practice, e.g., by the attending physician using sound medical judgment. The specific therapeutically effective dose for any particular patient will depend upon a variety of factors including the disease or disorder being treated and the severity thereof (e.g., its present status); the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", 10th Edition, A. Gilman, J. Hardman and L. Limbird, eds., McGraw-Hill Press, 155-173, 2001).

Compounds of the present invention may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosage may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, compounds of the present invention may be useful in the treatment of diseases and disorders characterized by aberrant activity of a protein that can be targeted for degradation by cereblon, participates in the inception, manifestation of one or more symptoms or markers, severity or progression of the disease or disorder, and where the degradation of the targeted protein may confer a therapeutic benefit. The diseases or disorders may be said to be characterized or mediated by aberrant protein activity which as disclosed above, may involve elevated protein levels compared to a non-pathological state. A "disease" is generally regarded as a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. In some embodiments, compounds of the application may be useful in the treatment of proliferative diseases and disorders (e.g., cancer or benign neoplasms). As used herein, the term "cell proliferative disease or disorder" refers to the conditions characterized by unregulated or abnormal cell growth, or both, including noncancerous conditions, precancerous conditions, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ecodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus *foliaceus*, paraneoplastic pemphigus, myasthenia gravis, immunoglobulin A nephropathy, autoimmune thyroiditis or Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cerebral malaria, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, graft-versus-host reaction, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sudden infant death syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, cystic fibrosis, uveitis, polymyositis, proctitis, interstitial lung fibrosis, dermatomyositis, arteriosclerosis, amyotrophic lateral sclerosis, asocality, immune response, varicosis, vaginitis, including chronic recurrent yeast vaginitis, depression, and Sudden Infant Death Syndrome.

In other embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) including leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, gestational trophoblastic tumor glioma, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodyplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver (hepatocellular), brain, lung, colorectal (e.g., colon), pancreas, prostate, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, primary CNS lymphoma (PCNSL), marginal zone lymphoma (MZL), leukemia, including chronic lymphocytic leukemia (CLL), childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the brain may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, a precancer or precancerous condition of the lung, benign growths or lesions of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioloalveolar carcinoma, giant cell carcinoma, spindle cell carcinoma, and large cell neuroendocrine carcinoma. Lung cancer includes lung neoplasms having histologic and ultrastructural heterogeneity (e.g., mixed cell types).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH-associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, an precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting the endometrium. Cell proliferative disorders of the endometrium may include endometrial cancer, a precancer or precancerous condition of the endometrium, benign growths or lesions of the endometrium, and malignant growths or lesions of the endometrium, and metastatic lesions in tissue and organs in the body other than the endometrium. Cell proliferative disorders of the endometrium may include hyperplasia, metaplasia, and dysplasia of the endometrium.

The compounds of the present invention may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present application may entail administration of compounds of the present invention or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5 or 6 weeks, and in other embodiments entails a 28-day cycle which includes daily administration for 3 weeks (21 days).

Combination Therapy

Compounds of the present invention may be used in combination with at least one other active agent, e.g., anti-cancer agent or regimen, in treating diseases and disorders. The term "in combination" in this context means that the agents are co-administered, which includes substantially contemporaneous administration, by the same or separate dosage forms, or sequentially, e.g., as part of the same treatment regimen or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of the present invention in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Therapeutics,* 10th ed., McGraw-Hill, New York, 2001; Physician's Desk Reference 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the compound of the invention and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the compound of the present invention and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example in the context of cancer treatment, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of the present invention or a pharmaceutical composition thereof. The kits or pharmaceutical systems of the invention may also include printed instructions for using the compound and composition.

These and other aspects of the present application will be further appreciated upon consideration of the following Examples, which are intended to illustrate certain particular embodiments of the application but are not intended to limit its scope, as defined by the claims.

EXAMPLES

Example 1: Synthesis of N-(2-(2,6-dioxopiperidin-3-yl)-1-oxoisoindolin-4-yl)-2-((2-((2-fluorophenyl)amino)pyrimidin-4-yl)amino)acetamide (1)

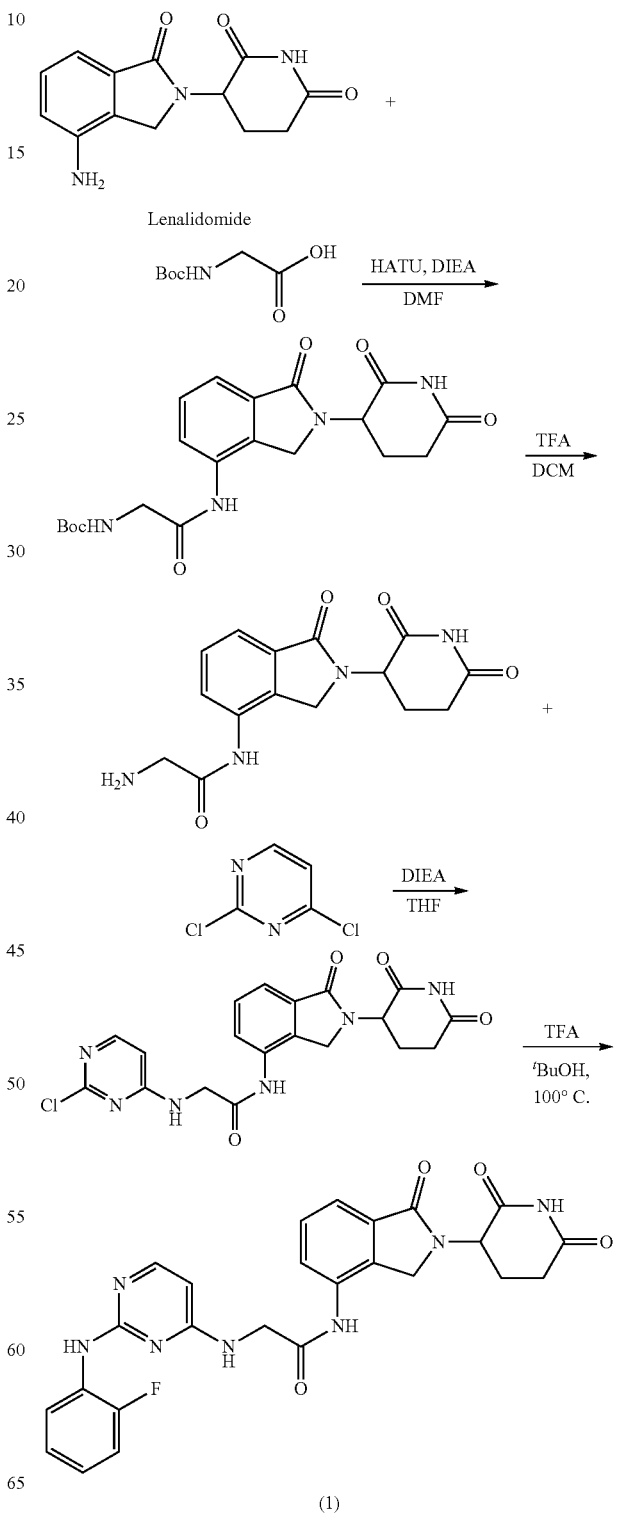

(1)

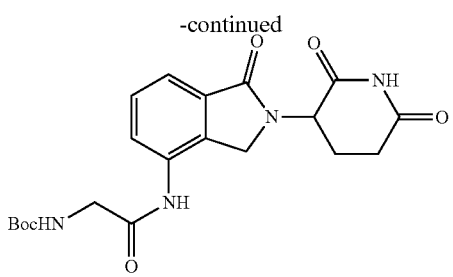

tert-Butyl (2-((2-(2,6-dioxopiperidin-3-yl)-1-oxoisoindolin-4-yl)amino)-2-oxoethyl)-carbamate To a solution of (tert-butoxycarbonyl)glycine (2.1 g, 12 mmol), DIEA (5 mL, 30 mmol) in DMF (30 mL) was added 1-[Bis(dimethylamino)methylene]-1H-1,2,3-triazolo[4,5-b]pyridinium 3-oxid hexafluorophosphate (HATU) (4.94 g, 13 mmol), stirred for 0.5 h, and then Lenalidomide (2.59 g, 10 mmol) was added, the mixture was then stirred at room temperature for another 1h. The mixture was then purified by silica gel (MeOH/DCM=0-10%) to obtain the title compound.

LCMS (m/z): 417 [M+H]$^+$.

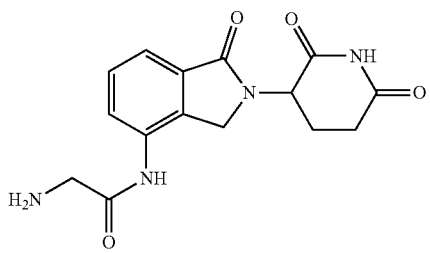 [SMILES: NCC(=O)Nc1cccc2c1CN(C1CCC(=O)NC1=O)C2=O]

2-Amino-N-(2-(2,6-dioxopiperidin-3-yl)-1-oxoisoindolin-4-yl)acetamide

To a solution of tert-Butyl (2-((2-(2,6-dioxopiperidin-3-yl)-1-oxoisoindolin-4-yl)amino)-2-oxoethyl)-carbamate in DCM (30 mL) was added TFA (10 mL), and stirred at room temperature for 3h. The mixture was then concentrated in vacuo, and purified by silica gel (MeOH/DCM=0-30%) to obtain the title compound (972 mg, 23% for 2 steps).

LCMS (m/z): 317 [M+H]$^+$.

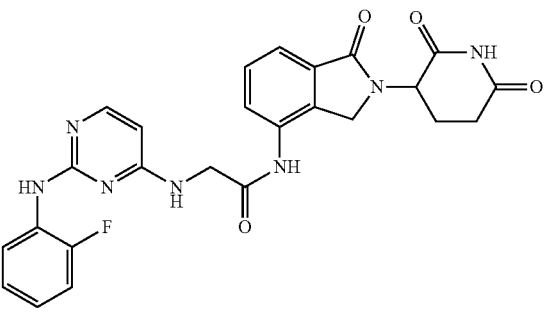

2-((2-chloropyrimidin-4-yl)amino)-N-(2-(2,6-dioxopiperidin-3-yl)-1-oxoisoindolin-4-yl) acetamide To a solution of 2-amino-N-(2-(2,6-dioxopiperidin-3-yl)-1-oxoisoindolin-4-yl)acetamide (972 mg, 2.26 mmol) and 2,4-dichloropyrimidine (332 mg, 2.26 mmol) in THF (20 mL) was added DIEA (1.1 mL, 6.78 mmol), and then stirred overnight. The mixture was then concentrated in vacuo, and purified by silica gel (MeOH/DCM=0-10%) to obtain the title compound (693 mg, 72%).

LCMS (m/z): 429 [M+H]$^+$.

(1)

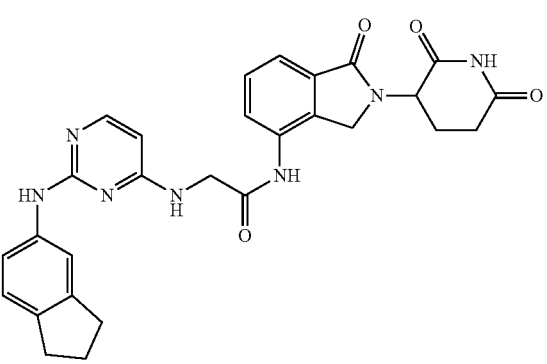

To a solution of 2-((2-chloropyrimidin-4-yl)amino)-N-(2-(2,6-dioxopiperidin-3-yl)-1-oxoisoindolin-4-yl) acetamide (50 mg, 0.12 mmol) and 2-fluoroaniline (13 mg, 0.12 mmol) in $^t$BuOH (1 mL) was added TFA (18 μL, 0.24 mmol), and then the mixture was heated to reflux overnight. The mixture was then concentrated in vacuo, and purified by prep-HPLC (MeOH/H$_2$O, 0.05% TFA) to obtain compound 1 (4.6 mg, 6%).

$^1$H NMR (500 MHz, DMSO-d$_6$) δ 11.05 (s, 1H), 10.18 (s, 1H), 10.06 (s, 1H), 9.38 (t, J=5.7 Hz, 1H), 7.90 (d, J=7.2 Hz, 1H), 7.83-7.74 (m, 2H), 7.57-7.49 (m, 2H), 7.26-7.16 (m, 1H), 7.08-6.97 (m, 1H), 6.45 (d, J=7.2 Hz, 1H), 5.16 (dd, J=13.3, 5.2 Hz, 1H), 4.31-4.22 (m, 4H), 2.93 (ddd, J=17.4, 13.6, 5.4 Hz, 1H), 2.65-2.56 (m, 1H), 2.24 (qd, J=13.2, 4.5 Hz, 1H), 2.03 (ddd, J=10.3, 5.4, 2.8 Hz, 1H).

LCMS (m/z): 504 [M+H]$^+$.

Example 2: Synthesis of 2-((2-((2,3-dihydro-1H-inden-5-yl)amino)pyrimidin-4-yl)amino)-N-(2-(2,6-dioxopiperidin-3-yl)-1-oxoisoindolin-4-yl)acetamide (2)

(2)

To a solution of 2-((2-chloropyrimidin-4-yl)amino)-N-(2-(2,6-dioxopiperidin-3-yl)-1-oxoisoindolin-4-yl) acetamide (50 mg, 0.12 mmol) and 2,3-dihydro-1H-inden-5-amine (16 mg, 0.12 mmol) in ᵗBuOH (1 mL) was added TFA (18 μL, 0.24 mmol), and then the mixture was heated to reflux overnight. The mixture was then concentrated in vacuo, and purified by prep-HPLC (MeOH/H₂O, 0.05% TFA) to obtain compound 2 (4.4 mg, 6%).

¹H NMR (500 MHz, DMSO-d₆) δ 11.01 (s, 1H), 10.32 (s, 1H), 10.11 (s, 1H), 9.30 (t, J=5.9 Hz, 1H), 7.82 (d, J=7.2 Hz, 1H), 7.58-7.48 (m, 2H), 7.34 (s, 1H), 7.26-7.18 (m, 2H), 7.08 (d, J=8.0 Hz, 1H), 6.39 (d, J=7.2 Hz, 1H), 5.12 (dd, J=13.3, 5.1 Hz, 1H), 4.33-4.25 (m, 4H), 2.85 (dt, J=14.5, 7.7 Hz, 2H), 2.73 (q, J=7.5 Hz, 4H), 2.07-1.96 (m, 2H), 1.91 (p, J=7.0 Hz, 2H).

LCMS (m/z): 526 [M+H]⁺.

Example 3: Synthesis of 2-((2-((benzo[d][1,3]dioxol-5-ylmethyl)amino)pyrimidin-4-yl)amino)-N-(2-(2,6-dioxopiperidin-3-yl)-1-oxoisoindolin-4-yl)acetamide (3)

(3)

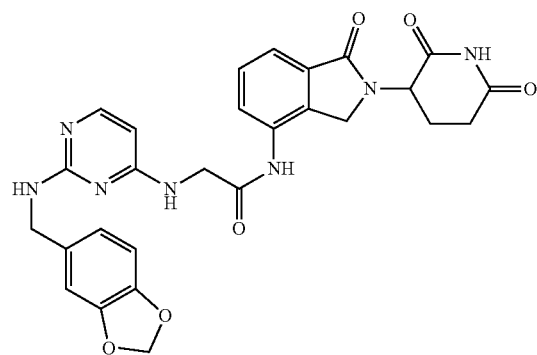

To a solution of 2-((2-chloropyrimidin-4-yl)amino)-N-(2-(2,6-dioxopiperidin-3-yl)-1-oxoisoindolin-4-yl) acetamide (50 mg, 0.12 mmol) and benzo[d][1,3]dioxol-5-ylmethanamine (18 mg, 0.12 mmol) in ᵗBuOH (1 mL) was added TFA (18 μL, 0.24 mmol), and then the mixture was heated to reflux overnight. The mixture was then concentrated in vacuo, and purified by prep-HPLC (MeOH/H₂O, 0.05% TFA) to obtain compound 3 (6.5 mg, 4%).

¹H NMR (500 MHz, DMSO-d₆) δ 11.02 (s, 1H), 9.85 (d, J=4.6 Hz, 1H), 7.78 (dd, J=7.6, 1.4 Hz, 1H), 7.68 (d, J=5.7 Hz, 1H), 7.54-7.43 (m, 2H), 7.32 (s, 1H), 6.94 (s, 1H), 6.82 (s, 1H), 6.76-6.65 (m, 2H), 5.90 (s, 2H), 5.86 (d, J=6.0 Hz, 1H), 5.14 (dd, J=13.3, 5.1 Hz, 1H), 4.36-4.22 (m, 4H), 4.09 (d, J=5.9 Hz, 2H), 2.92 (ddd, J=17.2, 13.6, 5.4 Hz, 1H), 2.69-2.57 (m, 1H), 2.32-2.18 (m, 1H), 2.03-1.96 (m, 1H).

LCMS (m/z): 544 [M+H]⁺.

Example 4: Synthesis of N-(2-(2,6-dioxopiperidin-3-yl)-1-oxoisoindolin-4-yl)-2-((2-((S)-2-(hydroxymethyl)pyrrolidin-1-yl)pyrimidin-4-yl)amino)acetamide (4)

(4)

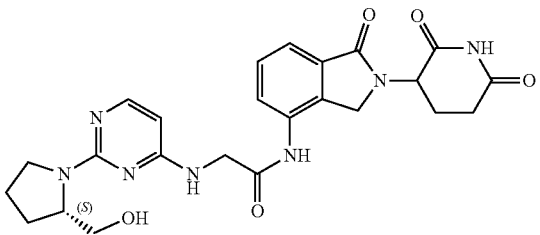

To a solution of 2-((2-chloropyrimidin-4-yl)amino)-N-(2-(2,6-dioxopiperidin-3-yl)-1-oxoisoindolin-4-yl) acetamide (50 mg, 0.12 mmol) and (S)-pyrrolidin-2-ylmethanol (12 mg, 0.12 mmol) in ᵗBuOH (1 mL) was added TFA (18 μL, 0.24 mmol), and then the mixture was heated to reflux overnight. The mixture was then concentrated in vacuo, and purified by prep-HPLC (MeOH/H₂O, 0.05% TFA) to obtain compound 4 (1.9 mg, 3%).

¹H NMR (500 MHz, DMSO-d₆) δ 11.88 (s, 1H), 11.04 (s, 1H), 10.13 (s, 1H), 9.12 (s, 1H), 7.83 (dd, J=7.6, 1.4 Hz, 1H), 7.73 (d, J=7.3 Hz, 1H), 7.57-7.46 (m, 2H), 6.29 (d, J=7.2 Hz, 1H), 5.18 (dd, J=13.3, 5.1 Hz, 1H), 4.42-4.26 (m, 4H), 3.64-3.34 (m, 4H), 2.94 (ddd, J=18.1, 13.5, 5.4 Hz, 1H), 2.67-2.60 (m, 1H), 2.30 (dd, J=13.1, 4.6 Hz, 1H), 2.10-1.90 (m, 6H).

LCMS (m/z): 494 [M+H]⁺.

Example 5: Synthesis of 2-((2-(benzo[d][1,3]dioxol-5-ylamino)pyrimidin-4-yl)amino)-N-(2-(2,6-dioxopiperidin-3-yl)-1-oxoisoindolin-4-yl)acetamide (5)

(5)

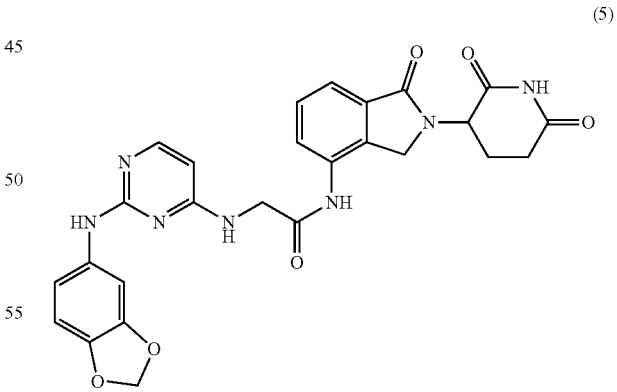

To a solution of 2-((2-chloropyrimidin-4-yl)amino)-N-(2-(2,6-dioxopiperidin-3-yl)-1-oxoisoindolin-4-yl) acetamide (60 mg, 0.14 mmol) and 2,3-dihydrobenzo[b][1,4]dioxin-6-amine (21 mg, 0.14 mmol) in ᵗBuOH (1 mL) was added TFA (21 μL, 0.28 mmol), and then the mixture was heated to reflux overnight. The mixture was then concentrated in vacuo, and purified by prep-HPLC (MeOH/H₂O, 0.05% TFA) to obtain compound 5 (5.2 mg, 6%).

¹H NMR (500 MHz, DMSO-d₆) δ 11.02 (s, 1H), 10.25 (s, 1H), 10.12 (s, 1H), 9.28 (s, 1H), 7.83-7.74 (m, 2H), 7.56-7.47 (m, 2H), 7.01 (d, J=2.5 Hz, 1H), 6.97 (d, J=8.6 Hz, 1H), 6.74 (d, J=8.7 Hz, 1H), 6.37 (d, J=7.2 Hz, 1H), 5.14 (dd, J=13.3, 5.1 Hz, 1H), 4.32 (s, 2H), 4.16-4.05 (m, 4H), 2.92 (ddd, J=17.2, 13.5, 5.4 Hz, 1H), 2.64-2.56 (m, 1H), 2.32-2.20 (m, 1H), 2.06-1.95 (m, 1H).

LCMS (m/z): 530 [M+H]⁺.

Example 6: Synthesis of N-(2-(2,6-dioxopiperidin-3-yl)-1-oxoisoindolin-4-yl)-2-((2-((3-(2-oxopyrrolidin-1-yl)propyl)amino)pyrimidin-4-yl)amino)acetamide (6)

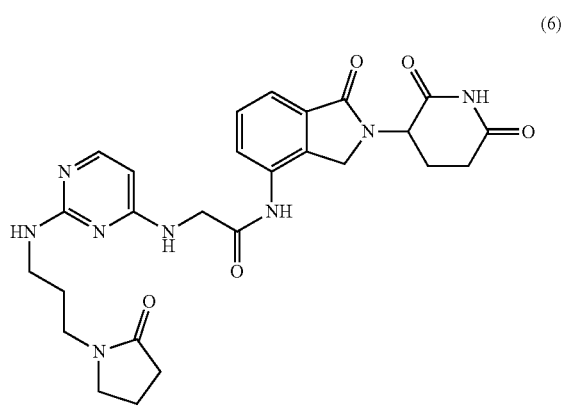 [SMILES: O=C1CCC(N2Cc3c(NC(=O)CNc4ccnc(NCCCN5CCCC5=O)n4)cccc3C2=O)C(=O)N1]

(6)

To a solution of 2-((2-chloropyrimidin-4-yl)amino)-N-(2-(2,6-dioxopiperidin-3-yl)-1-oxoisoindolin-4-yl) acetamide (60 mg, 0.14 mmol) and 11-(3-aminopropyl)pyrrolidin-2-one (20 mg, 0.14 mmol) in ᵗBuOH (1 mL) was added TFA (18 µL, 0.24 mmol), and then the mixture was heated to reflux overnight. The mixture was then concentrated in vacuo, and purified by prep-HPLC (MeOH/H₂O, 0.05% TFA) to obtain compound 6 (4.1 mg, 5%).

¹H NMR (500 MHz, DMSO-d₆) δ 11.94 (s, 1H), 11.04 (d, J=2.3 Hz, 1H), 10.20-10.08 (m, 1H), 8.04-7.93 (m, 1H), 7.85 (ddd, J=17.0, 7.4, 1.6 Hz, 1H), 7.74 (d, J=7.3 Hz, 1H), 7.58-7.46 (m, 2H), 6.30-6.23 (m, 1H), 5.17 (ddd, J=13.3, 5.2, 2.9 Hz, 1H), 4.49-4.21 (m, 4H), 3.31 (d, J=22.6 Hz, 2H), 3.19-3.08 (m, 2H), 2.98-2.90 (m, 1H), 2.67-2.59 (m, 1H), 2.34-2.25 (m, 1H), 2.14 (d, J=7.8 Hz, 1H), 2.08-1.99 (m, 1H), 1.81 (s, 1H), 1.62 (s, 1H).

LCMS (m/z): 535 [M+H]⁺.

Example 7: Synthesis of N-(2-(2,6-dioxopiperidin-3-yl)-1-oxoisoindolin-4-yl)-2-((2-((4-methoxyphenyl)amino)pyrimidin-4-yl)amino)acetamide (7)

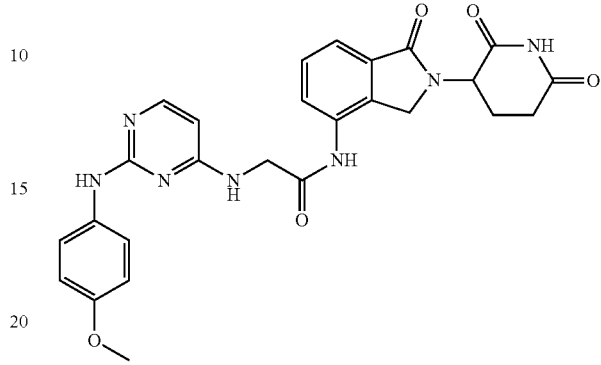

(7)

To a solution of 2-((2-chloropyrimidin-4-yl)amino)-N-(2-(2,6-dioxopiperidin-3-yl)-1-oxoisoindolin-4-yl) acetamide (100 mg, 0.234 mmol) and 4-methoxyaniline (29 mg, 0.234 mmol) in ᵗBuOH (1 mL) was added TFA (36 µL, 0.468 mmol), and then the mixture was heated to reflux overnight. The mixture was then concentrated in vacuo and purified by prep-HPLC (MeOH/H₂O, 0.05% TFA) to obtain compound 7 (10.9 mg, 7%).

¹H NMR (500 MHz, DMSO-d₆) δ 11.02 (s, 1H), 10.46 (s, 1H), 10.15 (s, 1H), 9.32 (d, J=5.7 Hz, 1H), 7.81 (td, J=9.1, 7.7, 4.1 Hz, 2H), 7.58-7.47 (m, 2H), 7.42 (d, J=8.5 Hz, 2H), 6.78 (d, J=8.5 Hz, 2H), 6.38 (d, J=7.2 Hz, 1H), 5.14 (dd, J=13.3, 5.1 Hz, 1H), 4.33-4.23 (m, 4H), 3.60 (s, 3H), 2.93 (ddd, J=17.2, 13.5, 5.4 Hz, 1H), 2.65-2.56 (m, 1H), 2.23 (qd, J=13.2, 4.4 Hz, 1H), 2.01 (dtd, J=12.4, 7.4, 6.2, 3.7 Hz, 1H).

LCMS (m/z): 516 [M+H]⁺.

Example 8: Synthesis of 2-((2-([1,1'-biphenyl]-4-yl)pyrimidin-4-yl)amino)-N-(2-(2,6-dioxopiperidin-3-yl)-1-oxoisoindolin-4-yl)acetamide (8)

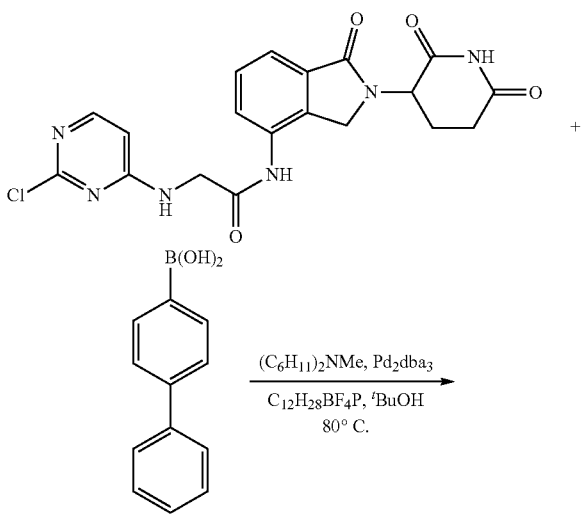

-continued

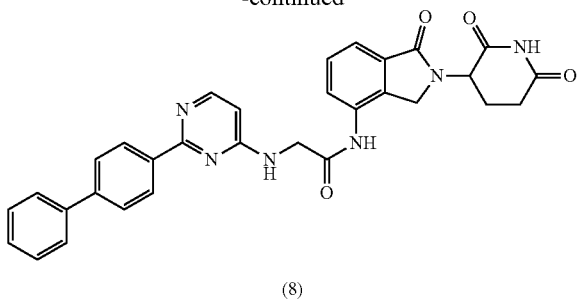

(8)

To a solution of 2-((2-chloropyrimidin-4-yl)amino)-N-(2-(2,6-dioxopiperidin-3-yl)-1-oxoisoindolin-4-yl) acetamide (110 mg, 0.24 mmol) and [1,1'-biphenyl]-4-ylboronic acid (54 mg, 0.28 mmol) in $^t$BuOH (2 mL) were added N,N-Dicyclohexylmethylamine (52 mg, 0.26 mmol), Pd$_2$dba$_3$ (22 mg, 0.024 mmol) and Tri-tert-butylphosphonium tetrafluoroborate (20 mg, 0.048 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 8 (4.4 mg, 3%).

$^1$H NMR (500 MHz, DMSO-d$_6$) δ 11.01 (s, 1H), 10.30 (s, 1H), 8.77 (dd, J=4.4, 1.4 Hz, 1H), 8.36 (d, J=8.2 Hz, 2H), 8.31-8.27 (m, 1H), 7.90-7.72 (m, 5H), 7.56-7.50 (m, 4H), 7.49-7.39 (m, 1H), 6.88 (d, J=6.7 Hz, 1H), 5.11 (dd, J=13.4, 5.0 Hz, 1H), 4.49 (d, J=5.4 Hz, 2H), 4.37 (s, 2H), 2.87 (t, J=13.9 Hz, 1H), 2.64 (d, J=5.1 Hz, 1H), 2.17 (d, J=13.4 Hz, 1H), 1.96 (s, 1H).

LCMS (m/z): 547 [M+H]$^+$.

Example 9: Synthesis of N-(2-(2,6-dioxopiperidin-3-yl)-1-oxoisoindolin-4-yl)-2-((2-(3-methoxyphenyl)pyrimidin-4-yl)amino)acetamide (9)

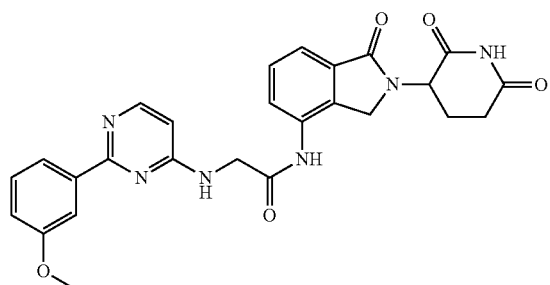

(9)

To a solution of 2-((2-chloropyrimidin-4-yl)amino)-N-(2-(2,6-dioxopiperidin-3-yl)-1-oxoisoindolin-4-yl) acetamide (100 mg, 0.23 mmol) and (3-methoxyphenyl)boronic acid (43 mg, 0.28 mmol) in $^t$BuOH (2 mL) were added N,N-Dicyclohexylmethylamine (49 mg, 0.25 mmol), Pd$_2$dba$_3$ (21 mg, 0.023 mmol) and Tri-tert-butylphosphonium tetrafluoroborate (13 mg, 0.046 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 9 (4.0 mg, 3%).

$^1$H NMR (500 MHz, DMSO-d$_6$) δ 11.03 (s, 1H), 10.31 (s, 1H), 9.79 (s, 1H), 8.24 (d, J=7.2 Hz, 1H), 8.19-8.17 (m, 1H), 7.81 (dd, J=7.6, 1.5 Hz, 1H), 7.68 (ddd, J=8.9, 7.3, 1.8 Hz, 1H), 7.56-7.52 (m, 2H), 7.32 (d, J=8.4 Hz, 1H), 7.11 (t, J=7.6 Hz, 1H), 6.98 (d, J=7.2 Hz, 1H), 5.14 (dd, J=13.3, 5.2 Hz, 1H), 4.50 (d, J=5.5 Hz, 2H), 4.36-4.25 (m, 2H), 3.98 (s, 3H), 2.92 (ddd, J=18.3, 13.4, 5.5 Hz, 1H), 2.62-2.56 (m, 1H), 2.15-2.07 (m, 1H), 2.00-1.96 (m, 1H).

LCMS (m/z): 501 [M+H]$^+$.

Example 10: Synthesis of 2-((2-(2,5-dimethoxyphenyl)pyrimidin-4-yl)amino)-N-(2-(2,6-dioxopiperidin-3-yl)-1-oxoisoindolin-4-yl)acetamide (10)

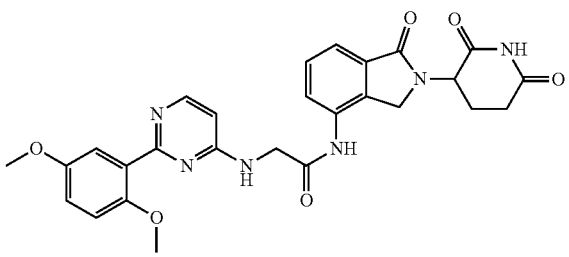

(10)

To a solution of 2-((2-chloropyrimidin-4-yl)amino)-N-(2-(2,6-dioxopiperidin-3-yl)-1-oxoisoindolin-4-yl) acetamide (100 mg, 0.23 mmol) and (2,5-dimethoxyphenyl)boronic acid (51 mg, 0.28 mmol) in $^t$BuOH (2 mL) were added N,N-Dicyclohexylmethylamine (49 mg, 0.25 mmol), Pd$_2$dba$_3$ (21 mg, 0.023 mmol) and Tri-tert-butylphosphonium tetrafluoroborate (13 mg, 0.046 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 10 (2.8 mg, 1%).

$^1$H NMR (500 MHz, DMSO-d$_6$) δ 11.01 (s, 1H), 10.30 (s, 1H), 9.60 (s, 1H), 8.23 (d, J=9.3 Hz, 1H), 8.16 (d, J=7.2 Hz, 1H), 7.84-7.78 (m, 1H), 7.59-7.49 (m, 2H), 6.88 (d, J=7.1 Hz, 1H), 6.80 (d, J=2.4 Hz, 1H), 6.66 (dt, J=8.9, 2.0 Hz, 1H), 5.13 (dd, J=13.3, 5.1 Hz, 1H), 4.47 (d, J=5.5 Hz, 2H), 4.32 (s, 2H), 4.01 (s, 3H), 3.89 (s, 3H), 2.92 (ddd, J=18.3, 13.5, 5.4 Hz, 1H), 2.58 (d, J=17.5 Hz, 1H), 2.20-2.08 (m, 1H), 2.01-1.90 (m, 1H).

LCMS (m/z): 531 [M+H]$^+$.

Example 11: Synthesis of N-(2-(2,6-dioxopiperidin-3-yl)-1-oxoisoindolin-4-yl)-2-((2-(4-fluorophenyl)pyrimidin-4-yl)amino)acetamide (11)

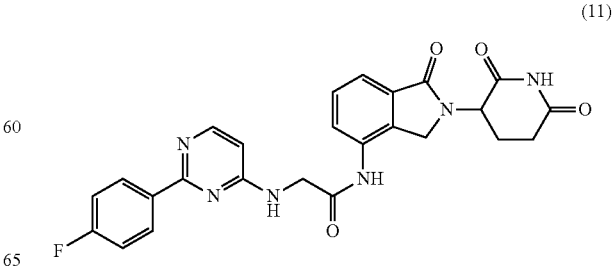

(11)

To a solution of 2-((2-chloropyrimidin-4-yl)amino)-N-(2-(2,6-dioxopiperidin-3-yl)-1-oxoisoindolin-4-yl) acetamide (100 mg, 0.23 mmol) and (4-fluorophenyl)boronic acid (50 mg, 0.28 mmol) in $^t$BuOH (2 mL) were added N,N-Dicyclohexylmethylamine (49 mg, 0.25 mmol), Pd$_2$dba$_3$ (21 mg, 0.023 mmol) and Tri-tert-butylphosphonium tetrafluoroborate (13 mg, 0.046 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 11 (10.0 mg, 3%).

$^1$H NMR (500 MHz, DMSO-d$_6$) δ 11.02 (s, 1H), 10.30 (s, 1H), 9.30 (s, 1H), 8.36-8.23 (m, 2H), 7.81 (d, J=7.2 Hz, 1H), 7.57-7.49 (m, 3H), 7.42 (t, J=8.6 Hz, 2H), 6.88 (d, J=6.8 Hz, 1H), 5.13 (dd, J=13.3, 5.1 Hz, 1H), 4.47 (d, J=5.3 Hz, 2H), 4.34 (s, 2H), 2.92 (ddt, J=18.1, 13.6, 4.7 Hz, 1H), 2.65-2.57 (m, 1H), 2.19-2.12 (m, 1H), 1.98 (d, J=10.2 Hz, 1H).

LCMS (m/z): 489 [M+H]$^+$.

Example 12: Synthesis of 2-((2-(4-acetylphenyl)pyrimidin-4-yl)amino)-N-(2-(2,6-dioxopiperidin-3-yl)-1-oxoisoindolin-4-yl)acetamide (12)

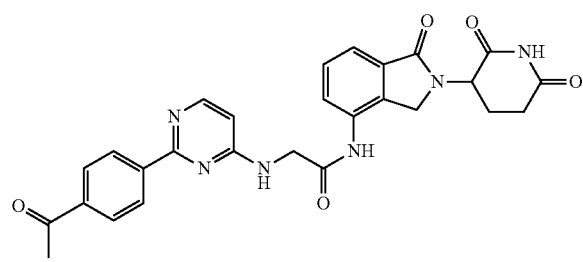

(12)

To a solution of 2-((2-chloropyrimidin-4-yl)amino)-N-(2-(2,6-dioxopiperidin-3-yl)-1-oxoisoindolin-4-yl) acetamide (100 mg, 0.23 mmol) and (4-acetylphenyl)boronic acid (45 mg, 0.28 mmol) in $^t$BuOH (2 mL) were added N,N-Dicyclohexylmethylamine (49 mg, 0.25 mmol), Pd$_2$dba$_3$ (21 mg, 0.023 mmol) and Tri-tert-butylphosphonium tetrafluoroborate (13 mg, 0.046 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain 12 (3.6 mg, 3%).

$^1$H NMR (500 MHz, DMSO-d$_6$) δ 10.99 (s, 1H), 10.22 (s, 1H), 8.75 (s, 1H), 8.40 (d, J=8.4 Hz, 2H), 8.29 (d, J=6.4 Hz, 1H), 8.06 (d, J=8.1 Hz, 2H), 7.81 (d, J=7.4 Hz, 1H), 7.57-7.47 (m, 2H), 6.82 (d, J=6.4 Hz, 1H), 5.11 (dd, J=13.1, 5.1 Hz, 1H), 4.43-4.38 (m, 2H), 4.33 (s, 2H), 2.90 (ddd, J=18.2, 13.5, 5.4 Hz, 1H), 2.63 (s, 3H), 2.57 (d, J=19.1 Hz, 1H), 2.14 (d, J=13.6 Hz, 1H), 2.00-1.91 (m, 1H).

LCMS (m/z): 513 [M+H]$^+$.

Example 13: Synthesis of 2-((2-(benzofuran-2-yl)pyrimidin-4-yl)amino)-N-(2-(2,6-dioxopiperidin-3-yl)-1-oxoisoindolin-4-yl)acetamide (13)

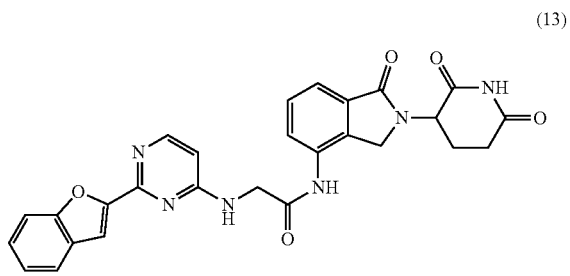 [SMILES: O=C1CCC(N2Cc3c(NC(=O)CNc4ccnc(-c5cc6ccccc6o5)n4)cccc3C2=O)C(=O)N1]

(13)

To a solution of 2-((2-chloropyrimidin-4-yl)amino)-N-(2-(2,6-dioxopiperidin-3-yl)-1-oxoisoindolin-4-yl) acetamide (150 mg, 0.35 mmol) and benzofuran-2-ylboronic acid (68 mg, 0.42 mmol) in $^t$BuOH (2 mL) were added N,N-Dicyclohexylmethylamine (75 mg, 0.39 mmol), Pd$_2$dba$_3$ (32 mg, 0.035 mmol) and Tri-tert-butylphosphonium tetrafluoroborate (20 mg, 0.07 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain 13 (12.3 mg, 6%).

$^1$H NMR (500 MHz, DMSO-d$_6$) δ 10.99 (s, 1H), 10.20 (s, 1H), 8.22 (d, J=5.8 Hz, 1H), 8.14 (s, 1H), 7.83 (dd, J=7.4, 1.6 Hz, 1H), 7.72 (d, J=7.8 Hz, 1H), 7.66 (s, 1H), 7.63 (d, J=8.3 Hz, 1H), 7.56-7.49 (m, 2H), 7.43-7.38 (m, 1H), 7.29 (s, 1H), 6.67 (s, 1H), 5.07 (dd, J=13.4, 4.9 Hz, 1H), 4.36 (d, J=22.3 Hz, 4H), 2.92-2.79 (m, 1H), 2.46 (s, 1H), 2.13 (d, J=13.9 Hz, 1H), 1.89 (s, 1H).

LCMS (m/z): 511 [M+H]$^+$.

Example 14: Synthesis of N-(2-(2,6-dioxopiperidin-3-yl)-1-oxoisoindolin-4-yl)-2-((2-((R)-2-(hydroxymethyl)pyrrolidin-1-yl)pyrimidin-4-yl)amino)acetamide (14)

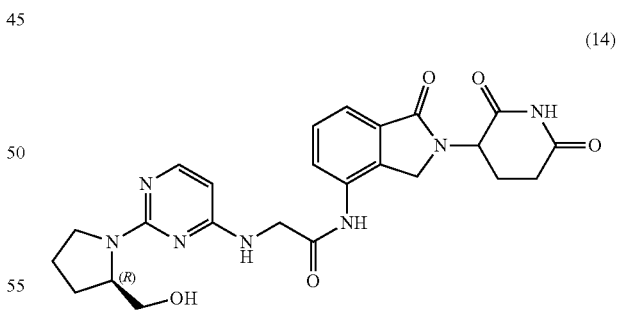

(14)

To a solution of 2-((2-chloropyrimidin-4-yl)amino)-N-(2-(2,6-dioxopiperidin-3-yl)-1-oxoisoindolin-4-yl) acetamide (210 mg, 0.5 mmol) and (R)-pyrrolidin-2-ylmethanol (50 mg, 0.5 mmol) in $^t$BuOH (2 mL) was added TFA (76 μL, 1.0 mmol), and then the mixture was heated to reflux overnight. The mixture was then concentrated in vacuo and purified by prep-HPLC (MeOH/H$_2$O, 0.05% TFA) to obtain compound 14 (5.1 mg, 2%).

$^1$H NMR (500 MHz, DMSO-d$_6$) δ 11.04 (s, 1H), 10.15 (s, 1H), 9.13 (s, 1H), 7.83 (d, J=7.6 Hz, 1H), 7.74 (d, J=7.2 Hz,

1H), 7.60-7.47 (m, 2H), 6.29 (d, J=7.2 Hz, 1H), 5.18 (dd, J=13.3, 5.2 Hz, 1H), 4.44-4.27 (m, 4H), 3.60-3.36 (m, 5H), 2.94 (ddd, J=18.1, 13.5, 5.5 Hz, 1H), 2.68-2.58 (m, 1H), 2.30 (tt, J=13.1, 6.7 Hz, 1H), 2.06-2.00 (m, 1H), 1.91 (dqd, J=18.5, 12.4, 6.4 Hz, 4H).

LCMS (m/z): 494 [M+H]$^+$.

Example 15: Synthesis of N-(2-(2,6-dioxopiperidin-3-yl)-1-oxoisoindolin-4-yl)-2-((2-((2-methoxyphenyl)amino)pyrimidin-4-yl)amino)acetamide (15)

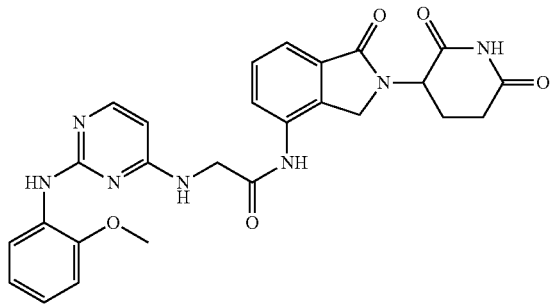

(15)

To a solution of 2-((2-chloropyrimidin-4-yl)amino)-N-(2-(2,6-dioxopiperidin-3-yl)-1-oxoisoindolin-4-yl) acetamide (140 mg, 0.33 mmol) and 2-methoxyaniline (40 mg, 0.33 mmol) in $^t$BuOH (2 mL) was added TFA (50 μL, 0.66 mmol), and then the mixture was heated to reflux overnight. The mixture was then concentrated in vacuo and purified by prep-HPLC (MeOH/H$_2$O, 0.05% TFA) to obtain compound 15 (9.5 mg, 5%).

$^1$H NMR (500 MHz, DMSO-d$_6$) δ 11.03 (s, 1H), 10.18 (s, 1H), 9.64 (s, 1H), 9.38 (t, J=5.8 Hz, 1H), 7.94-7.77 (m, 3H), 7.56-7.49 (m, 2H), 7.12 (t, J=7.7 Hz, 1H), 7.09-7.07 (m, 1H), 6.80 (t, J=7.7 Hz, 1H), 5.14 (dd, J=13.3, 5.2 Hz, 1H), 4.34-4.20 (m, 4H), 3.83 (s, 3H), 2.92 (ddd, J=17.2, 13.5, 5.4 Hz, 1H), 2.66-2.54 (m, 1H), 2.19 (qd, J=13.1, 4.4 Hz, 1H), 2.00 (dtd, J=12.8, 5.4, 2.2 Hz, 1H).

LCMS (m/z): 516 [M+H]$^+$.

Example 16: Synthesis of N-(2-(2,6-dioxopiperidin-3-yl)-1-oxoisoindolin-4-yl)-2-((2-(4-(3-(trifluoromethyl)phenyl)piperazin-1-yl)pyrimidin-4-yl)amino)acetamide (16)

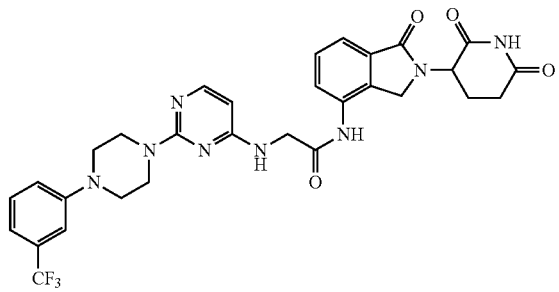

(16)

To a solution of 2-((2-chloropyrimidin-4-yl)amino)-N-(2-(2,6-dioxopiperidin-3-yl)-1-oxoisoindolin-4-yl) acetamide (135 mg, 0.316 mmol) and 1-(3-(trifluoromethyl)phenyl)piperazine (73 mg, 0.316 mmol) in $^t$BuOH (2 mL) was added TFA (48 μL, 0.632 mmol), and then the mixture was heated to reflux overnight. The mixture was then concentrated in vacuo and purified by prep-HPLC (MeOH/H$_2$O, 0.05% TFA) to obtain compound 16 (12.1 mg, 5%).

$^1$H NMR (500 MHz, DMSO-d$_6$) δ 11.04 (s, 1H), 10.27 (s, 1H), 9.27 (t, J=5.6 Hz, 1H), 7.88 (dd, J=7.4, 1.6 Hz, 1H), 7.80 (dd, J=7.2, 2.1 Hz, 1H), 7.59-7.51 (m, 2H), 7.47-7.43 (m, 1H), 7.29-7.22 (m, 1H), 7.17 (t, J=6.9 Hz, 1H), 7.11 (d, J=7.5 Hz, 1H), 5.18 (dd, J=13.3, 5.1 Hz, 1H), 4.36 (dd, J=34.4, 7.4 Hz, 4H), 3.85 (t, J=5.1 Hz, 4H), 3.37 (dt, J=48.5, 5.2 Hz, 4H), 2.93 (ddd, J=18.0, 13.5, 5.3 Hz, 1H), 2.64-2.57 (m, 1H), 2.31 (qd, J=13.2, 4.4 Hz, 1H), 2.04 (ddd, J=13.3, 5.8, 3.4 Hz, 1H).

LCMS (m/z): 623 [M+H]$^+$.

Example 17: Synthesis of N-(2-(2,6-dioxopiperidin-3-yl)-1-oxoisoindolin-4-yl)-2-((2-(methyl(phenyl)amino)pyrimidin-4-yl)amino)acetamide (17)

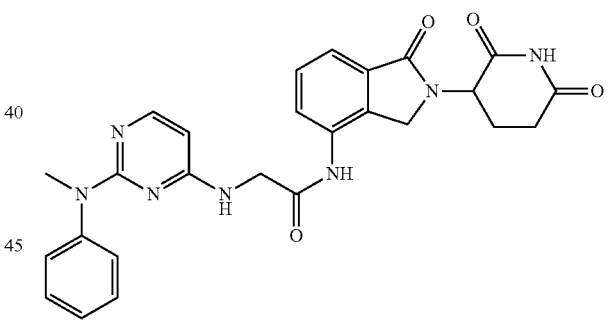

(17)

To a solution of 2-((2-chloropyrimidin-4-yl)amino)-N-(2-(2,6-dioxopiperidin-3-yl)-1-oxoisoindolin-4-yl) acetamide (135 mg, 0.316 mmol) and N-methylaniline (34 mg, 0.316 mmol) in $^t$BuOH (2 mL) was added TFA (48 μL, 0.632 mmol), and then the mixture was heated to reflux overnight. The mixture was then concentrated in and purified by prep-HPLC (MeOH/H$_2$O, 0.05% TFA) to obtain compound 17 (16.5 mg, 6%).

$^1$H NMR (500 MHz, DMSO-d$_6$) δ 11.04 (s, 1H), 10.20 (s, 1H), 9.35 (t, J=5.7 Hz, 1H), 7.86 (dd, J=7.4, 1.6 Hz, 1H), 7.60 (d, J=7.2 Hz, 1H), 7.57-7.53 (m, 2H), 7.49 (d, J=7.4 Hz, 2H), 7.45 (dt, J=8.2, 2.6 Hz, 3H), 6.38 (d, J=7.2 Hz, 1H), 5.18 (dd, J=13.3, 5.1 Hz, 1H), 4.46-4.28 (m, 4H), 3.44 (s, 3H), 2.99-2.87 (m, 1H), 2.67-2.58 (m, 1H), 2.31 (qd, J=13.2, 4.5 Hz, 1H), 2.13-1.96 (m, 1H).

LCMS (m/z): 500 [M+H]$^+$.

Example 18: Synthesis of 2-((2-(benzyl(ethyl)amino)pyrimidin-4-yl)amino)-N-(2-(2,6-dioxopiperidin-3-yl)-1-oxoisoindolin-4-yl)acetamide (25)

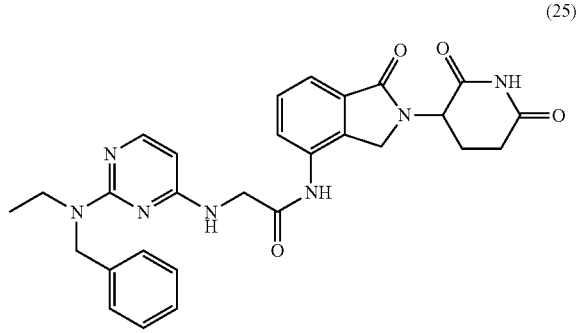 [SMILES: CCN(Cc1ccccc1)c1nccc(NCC(=O)Nc2cccc3c2CN(C2CCC(=O)NC2=O)C3=O)n1]

(25)

To a solution of 2-((2-chloropyrimidin-4-yl)amino)-N-(2-(2,6-dioxopiperidin-3-yl)-1-oxoisoindolin-4-yl) acetamide (98 mg, 0.23 mmol) and N-benzylethanamine (31 mg, 0.23 mmol) in $^t$BuOH (2 mL) was added TFA (36 μL, 0.46 mmol), and then the mixture was heated to reflux overnight. The mixture was then concentrated in vacuo and purified by prep-HPLC (MeOH/H$_2$O, 0.05% TFA) to obtain compound 25 (1.4 mg, 0.8%).

$^1$H NMR (500 MHz, DMSO-d$_6$) δ 11.04 (s, 1H), 10.05 (s, 1H), 7.77 (dt, J=13.2, 7.1 Hz, 2H), 7.54-7.46 (m, 2H), 7.40-7.18 (m, 6H), 6.33 (d, J=6.6 Hz, 1H), 5.15 (dd, J=13.2, 5.2 Hz, 1H), 4.78 (d, J=16.6 Hz, 2H), 4.30 (d, J=5.7 Hz, 4H), 3.52 (s, 2H), 2.93 (ddd, J=17.4, 13.6, 5.4 Hz, 1H), 2.68-2.57 (m, 1H), 2.17 (d, J=16.2 Hz, 1H), 2.01 (s, 1H), 1.03 (t, J=7.0 Hz, 3H).

LCMS (m/z): 528 [M+H]$^+$.

Example 19: Synthesis of N-(2-(2,6-dioxopiperidin-3-yl)-1-oxoisoindolin-4-yl)-2-((2-(4-fluoro-2-methoxyphenyl)pyrimidin-4-yl)amino)acetamide (34)

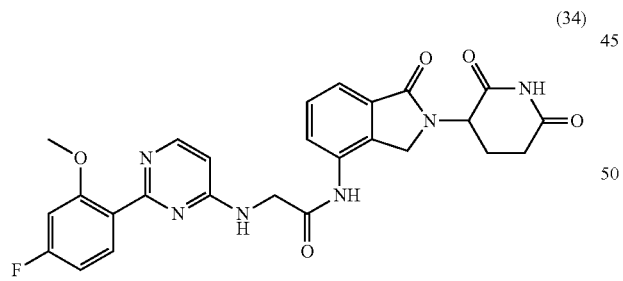

(34)

To a solution of 2-((2-chloropyrimidin-4-yl)amino)-N-(2-(2,6-dioxopiperidin-3-yl)-1-oxoisoindolin-4-yl) acetamide (100 mg, 0.23 mmol) and (4-fluoro-2-methoxyphenyl)boronic acid (60 mg, 0.28 mmol) in $^t$BuOH (2 mL) were added N,N-Dicyclohexylmethylamine (49 mg, 0.25 mmol), Pd$_2$dba$_3$ (21 mg, 0.023 mmol) and Tri-tert-butylphosphonium tetrafluoroborate (13 mg, 0.046 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 34 (1.6 mg, 1%).

LCMS (m/z): 519 [M+H]$^+$.

Examples 20: Synthesis of 3-(4-((2-((4-methoxyphenyl)amino)pyrimidin-4-yl)amino)-1-oxoisoindolin-2-yl)piperidine-2,6-dione (18)

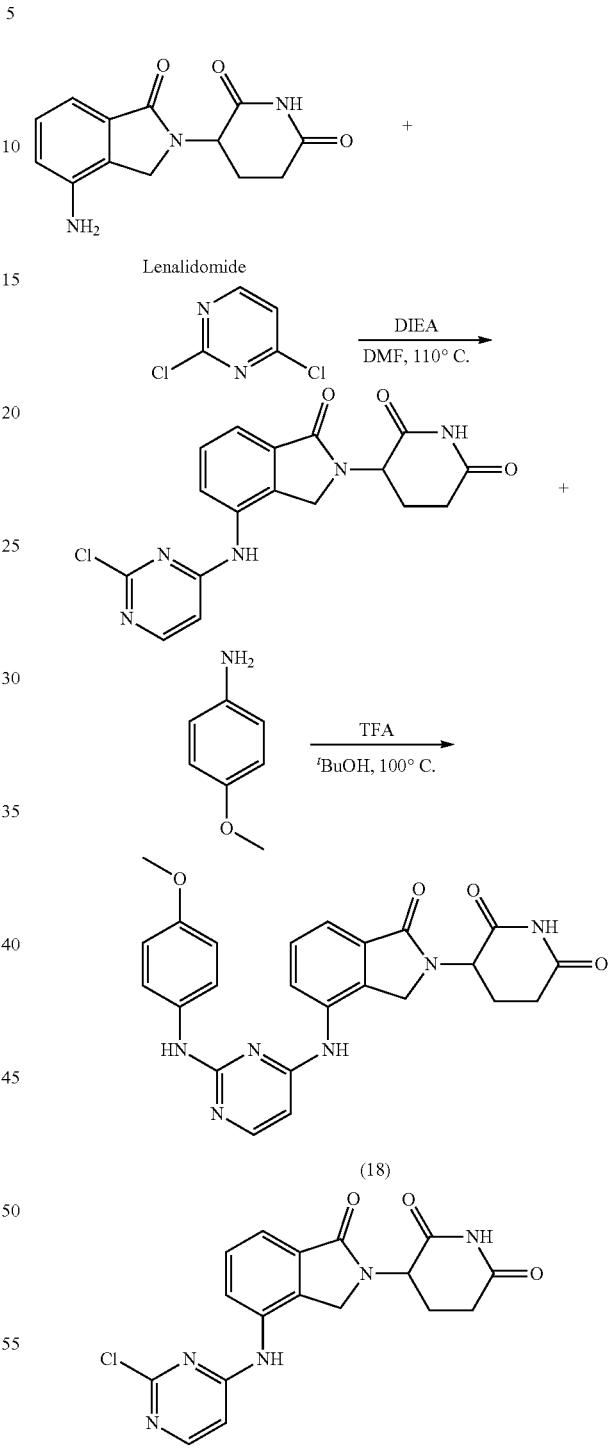

3-(4-((2-Chloropyrimidin-4-yl)amino)-1-oxoisoindolin-2-yl)piperidine-2,6-dione

To a solution of Lenalidomide (777 mg, 3 mmol) and 2,4-dichloropyrimidine (882 mg, 6 mmol) in DMF (6 mL)

was added DIEA (1.5 mL, 9 mmol), and then the mixture was heated to 110° C. overnight. The mixture was concentrated in vacuo and then purified by silica gel (MeOH/DCM=0-6%) to obtain the title compound (321 mg, 29%) as a pale white solid.

LCMS (m/z): 372 [M+H]+.

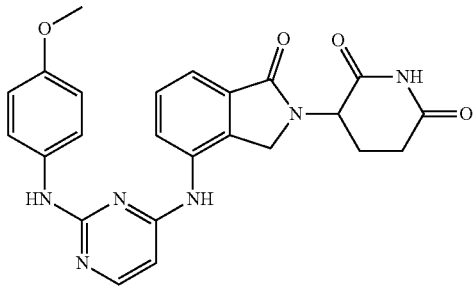

(18)

To a solution of 3-(4-((2-chloropyrimidin-4-yl)amino)-1-oxoisoindolin-2-yl)piperidine-2,6-dione (112 mg, 0.3 mmol) and 4-methoxyaniline (37 mg, 0.3 mmol) in $^t$BuOH (2 mL) was added TFA (45 µL, 0.6 mmol), and then the mixture was heated to reflux overnight. The mixture was then concentrated in vacuo and purified by prep-HPLC (MeOH/H$_2$O, 0.05% TFA) to obtain compound 18 (64.3 mg, 38%).

$^1$H NMR (500 MHz, DMSO-d$_6$) δ 11.01 (s, 1H), 10.36 (d, J=51.4 Hz, 2H), 7.94 (dd, J=41.2, 7.4 Hz, 2H), 7.65 (d, J=7.5 Hz, 1H), 7.56 (t, J=7.7 Hz, 1H), 7.32 (d, J=8.4 Hz, 2H), 6.85 (d, J=8.4 Hz, 2H), 6.43 (d, J=6.9 Hz, 1H), 5.14 (dd, J=13.2, 5.2 Hz, 1H), 4.46 (d, J=17.5 Hz, 1H), 4.33 (d, J=17.4 Hz, 1H), 3.74 (s, 3H), 2.90 (ddd, J=18.1, 13.6, 5.4 Hz, 1H), 2.62-2.53 (m, 1H), 2.35-2.24 (m, 1H), 1.87 (d, J=11.2 Hz, 1H).

LCMS (m/z): 459 [M+H]+.

Example 21: Synthesis of 3-(4-((2-((2,3-dihydrobenzo[b][1,4]dioxin-6-yl)amino)pyrimidin-4-yl)amino)-1-oxoisoindolin-2-yl)piperidine-2,6-dione (19)

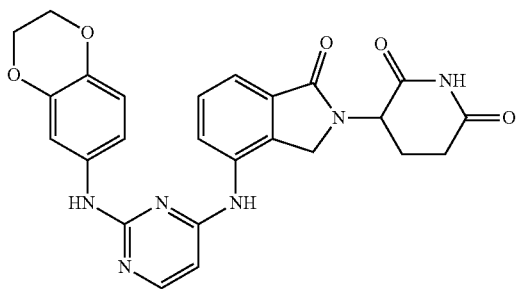

(19)

To a solution of 3-(4-((2-chloropyrimidin-4-yl)amino)-1-oxoisoindolin-2-yl)piperidine-2,6-dione (98 mg, 0.26 mmol) and 2,3-dihydrobenzo[b][1,4]dioxin-6-amine (40 mg, 0.26 mmol) in $^t$BuOH (2 mL) was added TFA (40 µL, 0.52 mmol), and then the mixture was heated to reflux overnight. The mixture was then concentrated in vacuo and purified by prep-HPLC (MeOH/H$_2$O, 0.05% TFA) to obtain compound 19 (15.9 mg, 10.1%).

$^1$H NMR (500 MHz, DMSO-d$_6$) δ 11.01 (s, 1H), 10.41 (d, J=52.9 Hz, 2H), 7.94 (dd, J=57.8, 7.2 Hz, 2H), 7.69-7.49 (m, 2H), 6.99 (s, 1H), 6.85-6.71 (m, 2H), 6.43 (d, J=6.9 Hz, 1H), 5.14 (dd, J=13.3, 5.3 Hz, 1H), 4.46 (d, J=17.5 Hz, 1H), 4.30 (d, J=17.4 Hz, 1H), 4.20 (s, 4H), 2.97-2.85 (m, 1H), 2.57 (s, 1H), 2.25 (s, 1H), 1.82 (s, 1H).

LCMS (m/z): 487 [M+H]+.

Example 22: Synthesis of 3-(4-((2-((2-fluorophenyl)amino)pyrimidin-4-yl)amino)-1-oxoisoindolin-2-yl)piperidine-2,6-dione (21)

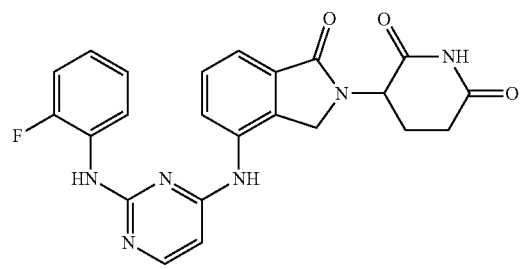

(21)

To a solution of 3-(4-((2-chloropyrimidin-4-yl)amino)-1-oxoisoindolin-2-yl)piperidine-2,6-dione (83 mg, 0.22 mmol) and 2-fluoroaniline (25 mg, 0.22 mmol) in $^t$BuOH (2 mL) was added TFA (33 µL, 0.44 mmol), and then the mixture was heated to reflux overnight. The mixture was then concentrated in vacuo and purified by prep-HPLC (MeOH/H$_2$O, 0.05% TFA) to obtain compound 21 (11.0 mg, 9%).

$^1$H NMR (500 MHz, DMSO-d$_6$) δ 11.02 (s, 1H), 10.31 (s, 1H), 10.01 (s, 1H), 8.07 (d, J=6.8 Hz, 1H), 7.89 (d, J=7.9 Hz, 1H), 7.59 (dd, J=9.9, 7.0 Hz, 2H), 7.46 (t, J=7.7 Hz, 1H), 7.30 (ddd, J=10.5, 8.3, 1.4 Hz, 1H), 7.24 (tdd, J=7.9, 5.2, 1.6 Hz, 1H), 7.11 (t, J=7.7 Hz, 1H), 6.49 (d, J=6.7 Hz, 1H), 5.14 (dd, J=13.3, 5.1 Hz, 1H), 4.45 (d, J=17.5 Hz, 1H), 4.33 (d, J=17.4 Hz, 1H), 2.96-2.84 (m, 1H), 2.59 (dt, J=17.0, 3.3 Hz, 1H), 2.31 (qd, J=13.2, 4.4 Hz, 1H), 1.97-1.84 (m, 1H).

LCMS (m/z): 447 [M+H]+.

Example 23: Synthesis of 3-(1-oxo-4-((2-((3-(2-oxopyrrolidin-1-yl)propyl)amino)pyrimidin-4-yl)amino)isoindolin-2-yl)piperidine-2,6-dione (22)

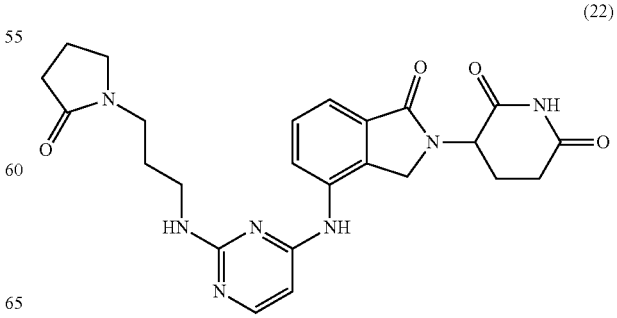

(22)

To a solution of 3-(4-((2-chloropyrimidin-4-yl)amino)-1-oxoisoindolin-2-yl)piperidine-2,6-dione (90 mg, 0.24 mmol) and 1-(3-aminopropyl)pyrrolidin-2-one (34 mg, 0.24 mmol) in 'BuOH (2 mL) was added TFA (36 μL, 0.48 mmol), and then the mixture was heated to reflux overnight. The mixture was then concentrated in vacuo and purified by prep-HPLC (MeOH/H$_2$O, 0.05% TFA) to obtain compound 22 (8.6 mg, 6%).

$^1$H NMR (500 MHz, DMSO-d$_6$) δ 11.03 (s, 1H), 10.58 (s, 1H), 8.32 (s, 1H), 7.93 (d, J=6.9 Hz, 2H), 7.65 (dd, J=18.8, 7.5 Hz, 2H), 6.38 (s, 1H), 5.19 (dd, J=13.3, 5.1 Hz, 1H), 4.48 (d, J=17.7 Hz, 1H), 4.38 (d, J=17.8 Hz, 1H), 3.17 (d, J=21.2 Hz, 6H), 2.94 (ddd, J=18.0, 13.7, 5.4 Hz, 1H), 2.60 (d, J=17.2 Hz, 1H), 2.39 (qd, J=13.2, 4.5 Hz, 1H), 2.14 (s, 2H), 2.02 (d, J=12.2 Hz, 1H), 1.73 (d, J=83.3 Hz, 4H).

LCMS (m/z): 478 [M+H]$^+$.

Example 24: Synthesis of 3-(1-oxo-4-((2-(4-(3-(trifluoromethyl)phenyl)piperazin-1-yl)pyrimidin-4-yl)amino)isoindolin-2-yl)piperidine-2,6-dione (23)

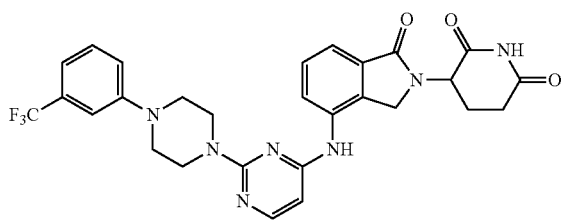

(23)

To a solution of 3-(4-((2-chloropyrimidin-4-yl)amino)-1-oxoisoindolin-2-yl)piperidine-2,6-dione (85 mg, 0.23 mmol) and 1-(3-(trifluoromethyl)phenyl)piperazine (53 mg, 0.23 mmol) in 'BuOH (2 mL) was added TFA (35 μL, 0.46 mmol), and then the mixture was heated to reflux overnight. The mixture was then concentrated in vacuo and purified by prep-HPLC (MeOH/H$_2$O, 0.05% TFA) to obtain compound 23 (10.9 mg, 7%).

$^1$H NMR (500 MHz, DMSO-d$_6$) δ 11.03 (s, 1H), 10.53 (s, 1H), 8.00 (d, J=6.9 Hz, 1H), 7.84 (d, J=7.8 Hz, 1H), 7.68 (d, J=7.4 Hz, 1H), 7.62 (t, J=7.7 Hz, 1H), 7.44 (t, J=8.0 Hz, 1H), 7.28-7.23 (m, 1H), 7.22 (t, J=1.9 Hz, 1H), 7.10 (d, J=7.6 Hz, 1H), 6.41 (d, J=6.9 Hz, 1H), 5.19 (dd, J=13.3, 5.2 Hz, 1H), 4.47 (d, J=17.6 Hz, 1H), 4.37 (d, J=17.5 Hz, 1H), 3.76 (q, J=4.0 Hz, 4H), 3.39 (t, J=4.3 Hz, 4H), 2.93 (ddd, J=17.4, 13.7, 5.4 Hz, 1H), 2.58 (dt, J=17.2, 3.1 Hz, 1H), 2.38 (qd, J=13.2, 4.4 Hz, 1H), 2.02 (ddq, J=10.5, 5.6, 3.3, 2.7 Hz, 1H).

LCMS (m/z): 566 [M+H]$^+$.

Example 25: Synthesis of 3-(4-((2-((2,3-dihydro-1H-inden-5-yl)amino)pyrimidin-4-yl)amino)-1-oxoisoindolin-2-yl)piperidine-2,6-dione (24)

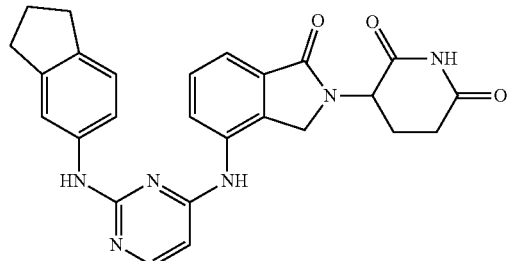

(24)

To a solution of 3-(4-((2-chloropyrimidin-4-yl)amino)-1-oxoisoindolin-2-yl)piperidine-2,6-dione (90 mg, 0.24 mmol) and 2,3-dihydro-1H-inden-5-amine (33 mg, 0.24 mmol) in 'BuOH (2 mL) was added TFA (36 μL, 0.48 mmol), and then the mixture was heated to reflux overnight. The mixture was then concentrated in vacuo and purified by prep-HPLC (MeOH/H$_2$O, 0.05% TFA) to obtain compound 24 (15.6 mg, 11%).

$^1$H NMR (500 MHz, DMSO-d$_6$) δ 10.99 (s, 1H), 10.47 (d, J=32.6 Hz, 2H), 8.03 (d, J=6.9 Hz, 1H), 7.87 (d, J=7.9 Hz, 1H), 7.68 (d, J=7.4 Hz, 1H), 7.58 (t, J=7.7 Hz, 1H), 7.32 (s, 1H), 7.09 (q, J=8.2 Hz, 2H), 6.45 (d, J=6.9 Hz, 1H), 5.12 (dd, J=13.3, 5.1 Hz, 1H), 4.46 (d, J=17.5 Hz, 1H), 4.31 (d, J=17.5 Hz, 1H), 2.88 (ddd, J=18.0, 13.6, 5.4 Hz, 1H), 2.79 (t, J=7.4 Hz, 2H), 2.68 (t, J=6.8 Hz, 2H), 2.57-2.55 (m, 1H), 2.22 (qd, J=13.3, 4.4 Hz, 1H), 1.98 (p, J=7.4 Hz, 2H), 1.75 (d, J=12.2 Hz, 1H).

LCMS (m/z): 469 [M+H]$^+$.

Example 26: Synthesis of 3-(4-((2-(benzyl(ethyl)amino)pyrimidin-4-yl)amino)-1-oxoisoindolin-2-yl)piperidine-2,6-dione (26)

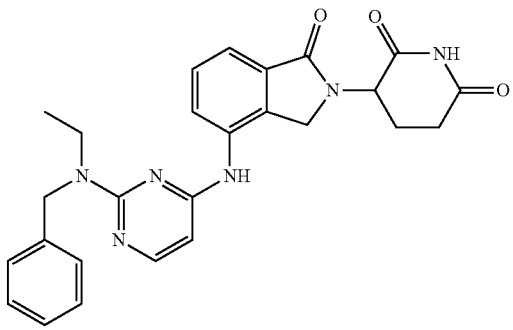

(26)

To a solution of 3-(4-((2-chloropyrimidin-4-yl)amino)-1-oxoisoindolin-2-yl)piperidine-2,6-dione (90 mg, 0.24 mmol) and N-benzylethanamine (33 mg, 0.24 mmol) in 'BuOH (2 mL) was added TFA (36 μL, 0.48 mmol), and then the mixture was heated to reflux overnight. The mixture was then concentrated in vacuo and purified by prep-HPLC (MeOH/H$_2$O, 0.05% TFA) to obtain compound 26 (7.6 mg, 5%).

¹H NMR (500 MHz, DMSO-d₆) δ 11.04 (s, 1H), 10.38 (s, 1H), 7.96 (d, J=7.0 Hz, 1H), 7.64-7.55 (m, 1H), 7.38-7.24 (m, 4H), 7.18 (s, 2H), 6.43 (s, 1H), 5.17 (dd, J=13.3, 5.1 Hz, 1H), 4.74 (s, 2H), 4.50-4.28 (m, 2H), 3.55 (s, 2H), 2.93 (ddd, J=17.3, 13.6, 5.4 Hz, 1H), 2.61 (dt, J=17.2, 3.3 Hz, 1H), 2.36 (qd, J=12.9, 4.4 Hz, 1H), 2.07-1.93 (m, 1H), 1.10 (s, 3H).
LCMS (m/z): 471 [M+H]⁺.

Example 27: Synthesis of 3-(4-((2-(methyl(phenyl)amino)pyrimidin-4-yl)amino)-1-oxoisoindolin-2-yl)piperidine-2,6-dione (27)

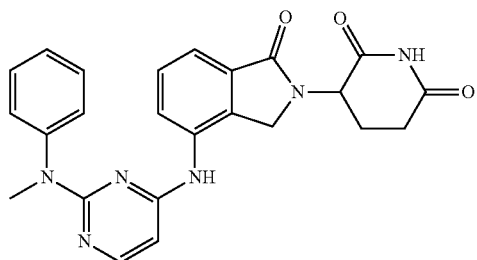

(27)

To a solution of 3-(4-((2-chloropyrimidin-4-yl)amino)-1-oxoisoindolin-2-yl)piperidine-2,6-dione (80 mg, 0.22 mmol) and N-methylaniline (23 mg, 0.22 mmol) in ᵗBuOH (2 mL) was added TFA (33 μL, 0.44 mmol), and then the mixture was heated to reflux overnight. The mixture was then concentrated in vacuo and purified by prep-HPLC (MeOH/H₂O, 0.05% TFA) to obtain compound 27 (17.4 mg, 14%).
¹H NMR (500 MHz, DMSO-d₆) δ 11.05 (s, 1H), 10.50 (s, 1H), 7.86 (dd, J=22.4, 7.5 Hz, 2H), 7.58 (d, J=7.5 Hz, 1H), 7.53 (t, J=7.6 Hz, 2H), 7.47-7.39 (m, 4H), 6.50 (d, J=7.0 Hz, 1H), 5.18 (dd, J=13.3, 5.1 Hz, 1H), 4.47 (d, J=17.5 Hz, 1H), 4.37 (d, J=17.5 Hz, 1H), 3.39 (s, 3H), 2.94 (ddd, J=17.3, 13.6, 5.4 Hz, 1H), 2.62 (dt, J=17.2, 3.4 Hz, 1H), 2.37 (qd, J=13.2, 4.4 Hz, 1H), 2.02 (dtd, J=12.8, 5.3, 2.3 Hz, 1H).
LCMS (m/z): 443 [M+H]⁺.

Example 28: Synthesis of 3-(4-((2-(mesitylamino)pyrimidin-4-yl)amino)-1-oxoisoindolin-2-yl)piperidine-2,6-dione (28)

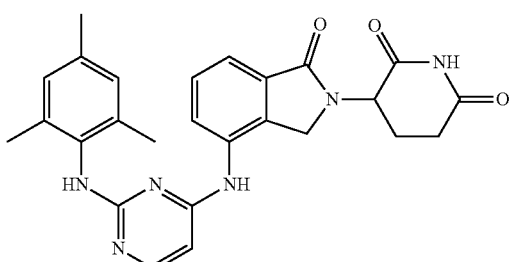

(28)

To a solution of 3-(4-((2-chloropyrimidin-4-yl)amino)-1-oxoisoindolin-2-yl)piperidine-2,6-dione (86 mg, 0.23 mmol) and 2,4,6-trimethylaniline (31 mg, 0.23 mmol) in ᵗBuOH (2 mL) was added TFA (35 μL, 0.46 mmol), and then the mixture was heated to reflux overnight. The mixture was then concentrated in vacuo and purified by prep-HPLC (MeOH/H₂O, 0.05% TFA) to obtain compound 28 (4.7 mg, 4%).
LCMS (m/z): 471 [M+H]⁺.

Example 29: Synthesis of 3-(4-((2-((S)-2-(hydroxymethyl)pyrrolidin-1-yl)pyrimidin-4-yl)amino)-1-oxoisoindolin-2-yl)piperidine-2,6-dione (29)

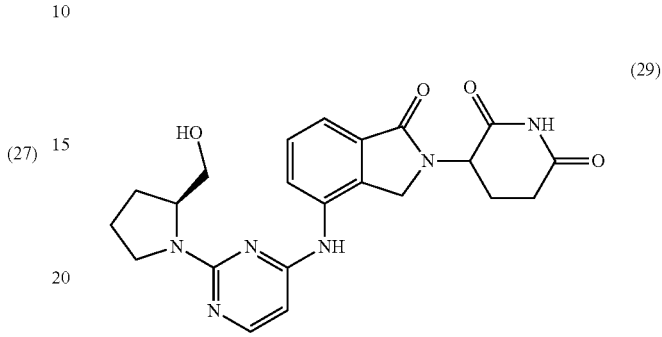

(29)

To a solution of 3-(4-((2-chloropyrimidin-4-yl)amino)-1-oxoisoindolin-2-yl)piperidine-2,6-dione (82 mg, 0.22 mmol) and (S)-pyrrolidin-2-ylmethanol (23 mg, 0.22 mmol) in ᵗBuOH (2 mL) was added TFA (33 μL, 0.44 mmol), and then the mixture was heated to reflux overnight. The mixture was then concentrated in vacuo and purified by prep-HPLC (MeOH/H₂O, 0.05% TFA) to obtain 29 (6.3 mg, 5%).
¹H NMR (500 MHz, DMSO-d₆) δ 11.03 (s, 1H), 10.46 (s, 2H), 8.12-7.87 (m, 2H), 7.63 (dd, J=20.9, 7.6 Hz, 2H), 6.44 (s, 1H), 5.19 (dt, J=13.3, 5.2 Hz, 1H), 4.57-4.31 (m, 2H), 4.11 (s, 1H), 3.47 (d, J=38.9 Hz, 4H), 2.94 (ddd, J=18.2, 13.9, 5.0 Hz, 1H), 2.66-2.56 (m, 1H), 2.40-2.31 (m, 1H), 2.09 (s, 1H), 2.05-1.84 (m, 4H).
LCMS (m/z): 437 [M+H]⁺.

Example 30: Synthesis of 3-(4-((2-((R)-2-(hydroxymethyl)pyrrolidin-1-yl)pyrimidin-4-yl)amino)-1-oxoisoindolin-2-yl)piperidine-2,6-dione (30)

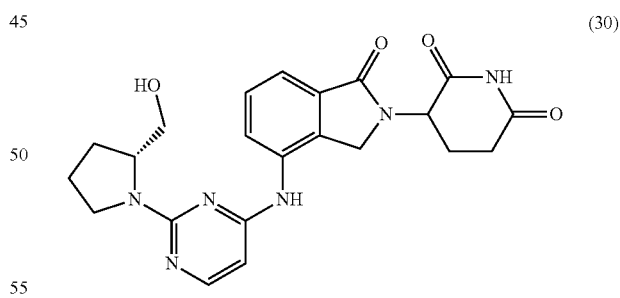

(30)

To a solution of 3-(4-((2-chloropyrimidin-4-yl)amino)-1-oxoisoindolin-2-yl)piperidine-2,6-dione (82 mg, 0.22 mmol) and (R)-pyrrolidin-2-ylmethanol (23 mg, 0.22 mmol) in ᵗBuOH (2 mL) was added TFA (33 μL, 0.44 mmol), and then the mixture was heated to reflux overnight. The mixture was then concentrated in vacuo and purified by prep-HPLC (MeOH/H₂O, 0.05% TFA) to obtain compound 30 (12.0 mg, 10%).
¹H NMR (500 MHz, DMSO-d₆) δ 11.03 (s, 1H), 10.49 (s, 1H), 8.22-7.88 (m, 2H), 7.74-7.37 (m, 2H), 6.44 (s, 1H), 5.18 (dt, J=13.3, 5.2 Hz, 1H), 4.56-4.28 (m, 2H), 4.11 (s, 1H), 3.63-3.37 (m, 4H), 2.99-2.85 (m, 1H), 2.67-2.56 (m, 1H), 2.43-2.32 (m, 1H), 2.11 (d, J=15.7 Hz, 1H), 2.06-1.83 (m, 5H).

LCMS (m/z): 437 [M+H]+.

Example 31: Synthesis of 3-(4-((2-(((R)-1-hydroxy-3-methylbutan-2-yl)amino)pyrimidin-4-yl)amino)-1-oxoisoindolin-2-yl)piperidine-2,6-dione (37)

(37)

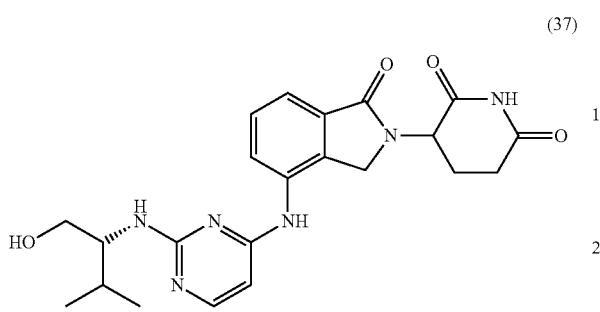

To a solution of 3-(4-((2-chloropyrimidin-4-yl)amino)-1-oxoisoindolin-2-yl)piperidine-2,6-dione (100 mg, 0.27 mmol) and (R)-2-amino-3-methylbutan-1-ol (28 mg, 0.27 mmol) in ᵗBuOH (2 mL) was added TFA (41 μL, 0.54 mmol), and then the mixture was heated to reflux overnight. The mixture was then concentrated in vacuo and purified by prep-HPLC (MeOH/H₂O, 0.05% TFA) to obtain compound 37 (4.5 mg, 3%).

¹H NMR (500 MHz, DMSO-d₆) δ 11.02 (s, 1H), 10.50 (s, 1H), 8.21 (s, 1H), 7.94 (d, J=7.3 Hz, 2H), 7.66 (d, J=7.1 Hz, 1H), 7.60 (t, J=7.7 Hz, 1H), 6.37 (s, 1H), 5.17 (dd, J=13.1, 5.1 Hz, 1H), 4.59-4.34 (m, 2H), 3.48 (d, J=9.0 Hz, 2H), 2.99-2.87 (m, 1H), 2.62 (dd, J=15.3, 11.7 Hz, 1H), 2.44-2.31 (m, 1H), 2.01 (d, J=16.2 Hz, 1H), 1.84 (s, 1H), 0.86 (d, J=42.6 Hz, 6H).

LCMS (m/z): 439 [M+H]+.

Example 32: Synthesis of 3-(4-((2-((2-methoxyphenyl)amino)pyrimidin-4-yl)amino)-1-oxoisoindolin-2-yl)piperidine-2,6-dione (38)

(38)

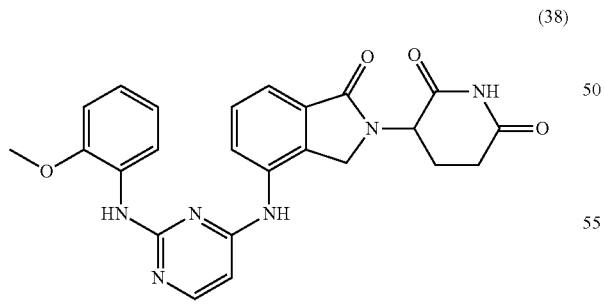

To a solution of 3-(4-((2-chloropyrimidin-4-yl)amino)-1-oxoisoindolin-2-yl)piperidine-2,6-dione (100 mg, 0.27 mmol) and 2-methoxyaniline (33 mg, 0.27 mmol) in ᵗBuOH (2 mL) was added TFA (41 μL, 0.54 mmol), and then the mixture was heated to reflux overnight. The mixture was then concentrated in vacuo and purified by prep-HPLC (MeOH/H₂O, 0.05% TFA) to obtain compound 38 (20.6 mg, 13%).

¹H NMR (500 MHz, DMSO-d₆) δ 11.02 (s, 1H), 10.64 (s, 1H), 9.86-9.75 (m, 1H), 8.04 (d, J=7.0 Hz, 1H), 7.88 (d, J=7.9 Hz, 1H), 7.65 (dd, J=7.5, 0.9 Hz, 1H), 7.53 (t, J=7.6 Hz, 2H), 7.20 (t, J=7.6 Hz, 1H), 7.11 (dd, J=8.4, 1.4 Hz, 1H), 6.82 (t, J=7.8 Hz, 1H), 6.51 (d, J=7.1 Hz, 1H), 5.14 (dd, J=13.2, 5.2 Hz, 1H), 4.47 (d, J=17.5 Hz, 1H), 4.34 (d, J=17.5 Hz, 1H), 3.82 (s, 3H), 2.90 (ddd, J=17.3, 13.7, 5.4 Hz, 1H), 2.57 (dt, J=17.2, 3.4 Hz, 1H), 2.28 (qd, J=13.2, 4.4 Hz, 1H), 1.87 (d, J=12.6 Hz, 1H).

LCMS (m/z): 459 [M+H]+.

Example 33: Synthesis of 4-((4-((2-(2,6-dioxopiperidin-3-yl)-1-oxoisoindolin-4-yl)amino)pyrimidin-2-yl)amino)benzenesulfonamide (40)

(40)

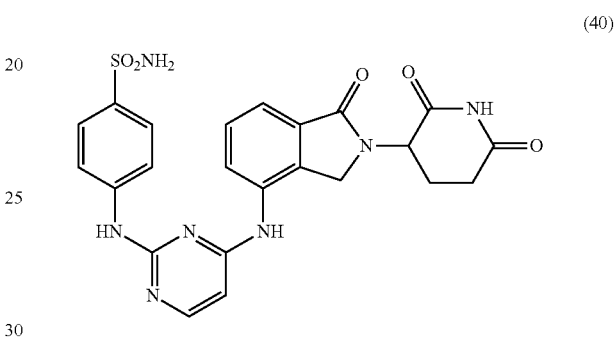

To a solution of 3-(4-((2-chloropyrimidin-4-yl)amino)-1-oxoisoindolin-2-yl)piperidine-2,6-dione (60 mg, 0.16 mmol) and 4-aminobenzenesulfonamide (28 mg, 0.16 mmol) in ᵗBuOH (2 mL) was added TFA (24 μL, 0.32 mmol), and then the mixture was heated to reflux overnight. The mixture was then concentrated in vacuo and purified by prep-HPLC (MeOH/H₂O, 0.05% TFA) to obtain compound 40 (9.0 mg, 9%).

¹H NMR (500 MHz, DMSO-d₆) δ 11.01 (s, 1H), 10.39 (s, 1H), 10.17 (s, 1H), 8.12 (d, J=6.5 Hz, 1H), 7.97 (d, J=7.7 Hz, 1H), 7.72-7.55 (m, 6H), 7.24 (s, 2H), 6.48 (d, J=6.6 Hz, 1H), 5.15 (dd, J=13.3, 5.2 Hz, 1H), 4.48 (d, J=17.5 Hz, 1H), 4.37 (d, J=17.5 Hz, 1H), 2.90 (ddd, J=17.3, 13.6, 5.4 Hz, 1H), 2.56 (dt, J=16.9, 3.4 Hz, 1H), 2.30 (qd, J=13.2, 4.5 Hz, 1H), 1.90 (dtd, J=12.9, 5.4, 2.3 Hz, 1H).

LCMS (m/z): 508 [M+H]+.

Example 34: Synthesis of 3-(4-((2-(indolin-5-ylamino)pyrimidin-4-yl)amino)-1-oxoisoindolin-2-yl)piperidine-2,6-dione (43)

(43)

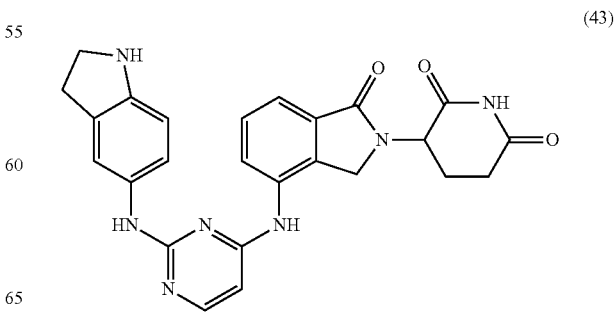

To a solution of 3-(4-((2-chloropyrimidin-4-yl)amino)-1-oxoisoindolin-2-yl)piperidine-2,6-dione (50 mg, 0.135 mmol) and tert-butyl 5-aminoindoline-1-carboxylate (32 mg, 0.135 mmol) in ᵗBuOH (2 mL) was added TFA (21 μL, 0.27 mmol), and then the mixture was heated to reflux overnight. The mixture was then concentrated in vacuo and purified by prep-HPLC (MeOH/H₂O, 0.05% TFA) to obtain compound 43 (10.4 mg, 13%).

¹H NMR (500 MHz, DMSO-d₆) δ 11.01 (s, 1H), 10.48 (d, J=30.2 Hz, 2H), 8.02 (d, J=6.9 Hz, 1H), 7.95 (d, J=7.8 Hz, 1H), 7.66 (dd, J=7.5, 1.1 Hz, 1H), 7.61 (t, J=7.6 Hz, 1H), 7.07 (s, 1H), 7.01 (s, 2H), 6.46 (d, J=6.9 Hz, 1H), 5.15 (dd, J=13.2, 5.1 Hz, 1H), 4.49 (d, J=17.5 Hz, 1H), 4.34 (d, J=17.5 Hz, 1H), 3.56 (t, J=8.2 Hz, 2H), 2.99 (t, J=8.1 Hz, 2H), 2.94-2.85 (m, 1H), 2.64-2.55 (m, 1H), 2.33 (ddd, J=26.6, 13.2, 3.2 Hz, 1H), 2.25 (s, 1H), 1.90 (dd, J=11.1, 5.2 Hz, 1H).

LCMS (m/z): 470 [M+H]⁺.

Example 35: Synthesis of 3-(4-((2-(((3s,5s,7s)-adamantan-1-yl)amino)pyrimidin-4-yl)amino)-1-oxoisoindolin-2-yl)piperidine-2,6-dione (44)

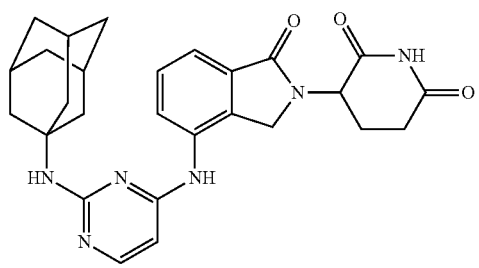

(44)

To a solution of 3-(4-((2-chloropyrimidin-4-yl)amino)-1-oxoisoindolin-2-yl)piperidine-2,6-dione (50 mg, 0.135 mmol) and (3s,5s,7s)-adamantan-1-amine (24 mg, 0.162 mmol) in ᵗBuOH (2 mL) was added TFA (67 μL, 0.405 mmol), and then the mixture was heated to reflux overnight. The mixture was then concentrated in vacuo and purified by prep-HPLC (MeOH/H₂O, 0.05% TFA) to obtain compound 44 (4.1 mg, 3%).

¹H NMR (500 MHz, DMSO-d₆) δ 11.01 (s, 1H), 10.61 (s, 1H), 7.99 (s, 1H), 7.93 (d, J=7.2 Hz, 1H), 7.72 (dd, J=10.6, 7.6 Hz, 2H), 7.62 (t, J=7.6 Hz, 1H), 6.33 (d, J=7.2 Hz, 1H), 5.16 (dd, J=13.3, 5.2 Hz, 1H), 4.40 (d, J=17.6 Hz, 1H), 4.30 (d, J=17.6 Hz, 1H), 2.92 (ddd, J=17.3, 13.6, 5.4 Hz, 1H), 2.64-2.53 (m, 1H), 2.44-2.36 (m, 1H), 2.09 (s, 1H), 1.96-1.91 (m, 1H), 1.86 (s, 3H), 1.76 (s, 6H), 1.50 (d, J=12.2 Hz, 3H), 1.33 (d, J=11.9 Hz, 3H).

LCMS (m/z): 487 [M+H]⁺.

Example 36: Synthesis of 3-(4-((2-(naphthalen-2-ylamino)pyrimidin-4-yl)amino)-1-oxoisoindolin-2-yl)piperidine-2,6-dione (45)

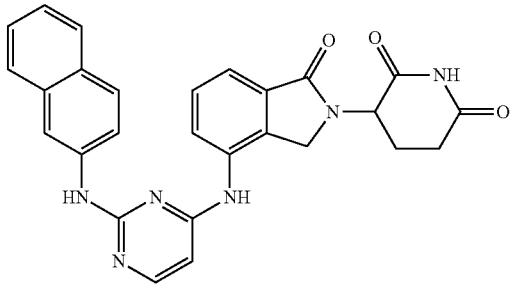

(45)

To a solution of 3-(4-((2-chloropyrimidin-4-yl)amino)-1-oxoisoindolin-2-yl)piperidine-2,6-dione (50 mg, 0.135 mmol) and tert-butyl 5-aminoindoline-1-carboxylate (23 mg, 0.162 mmol) in ᵗBuOH (2 mL) was added TFA (21 μL, 0.27 mmol), and then the mixture was heated to reflux overnight. The mixture was then concentrated in vacuo and purified by prep-HPLC (MeOH/H₂O, 0.05% TFA) to obtain compound 45 (16.8 mg, 21%).

¹H NMR (500 MHz, DMSO-d₆) δ 10.98 (s, 1H), 10.79 (s, 1H), 10.61 (s, 1H), 8.11 (d, J=7.0 Hz, 1H), 8.03-8.00 (m, 1H), 7.95 (d, J=7.9 Hz, 1H), 7.84 (t, J=8.3 Hz, 2H), 7.71 (d, J=7.5 Hz, 1H), 7.58 (d, J=7.7 Hz, 1H), 7.55-7.39 (m, 4H), 6.52 (d, J=6.9 Hz, 1H), 5.08 (dd, J=13.2, 5.2 Hz, 1H), 4.49 (d, J=17.6 Hz, 1H), 4.35 (d, J=17.6 Hz, 1H), 2.81 (ddd, J=17.2, 13.7, 5.4 Hz, 1H), 2.45 (s, 1H), 2.16 (dt, J=11.5, 5.3 Hz, 1H), 1.62 (s, 1H).

LCMS (m/z): 479 [M+H]⁺.

Example 37: Synthesis of 3-(4-((2-((9H-fluoren-3-yl)amino)pyrimidin-4-yl)amino)-1-oxoisoindolin-2-yl)piperidine-2,6-dione (46)

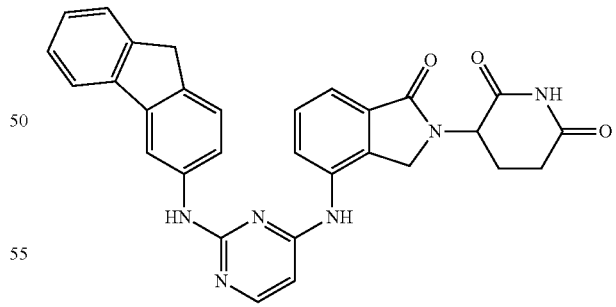

(46)

To a solution of 3-(4-((2-chloropyrimidin-4-yl)amino)-1-oxoisoindolin-2-yl)piperidine-2,6-dione (50 mg, 0.135 mmol) and 9H-fluoren-3-amine (24 mg, 0.135 mmol) in ᵗBuOH (2 mL) was added TFA (21 μL, 0.27 mmol), and then the mixture was heated to reflux overnight. The mixture was then concentrated and purified by prep-HPLC (MeOH/H₂O, 0.05% TFA) to obtain compound 46 (30.0 mg, 37%).

¹H NMR (500 MHz, DMSO-d₆) δ 10.99 (s, 1H), 10.79 (s, 1H), 10.64 (s, 1H), 8.10 (d, J=6.9 Hz, 1H), 7.92 (d, J=7.9 Hz,

1H), 7.82 (d, J=7.5 Hz, 1H), 7.79-7.74 (m, 1H), 7.74-7.70 (m, 2H), 7.63 (t, J=7.7 Hz, 1H), 7.55 (d, J=7.4 Hz, 1H), 7.39-7.33 (m, 2H), 7.28 (td, J=7.4, 1.2 Hz, 1H), 6.50 (d, J=7.0 Hz, 1H), 5.12 (dd, J=13.2, 5.2 Hz, 1H), 4.51 (d, J=17.6 Hz, 1H), 4.36 (d, J=17.5 Hz, 1H), 2.85 (ddd, J=17.3, 13.6, 5.4 Hz, 1H), 2.54 (d, J=11.7 Hz, 1H), 2.30-2.15 (m, 1H), 1.80-1.67 (m, 1H).

LCMS (m/z): 517 [M+H]$^+$.

Example 38: Synthesis of 3-(1-oxo-4-((2-((5,6,7,8-tetrahydronaphthalen-2-yl)amino)pyrimidin-4-yl)amino)isoindolin-2-yl)piperidine-2,6-dione (52)

(52)

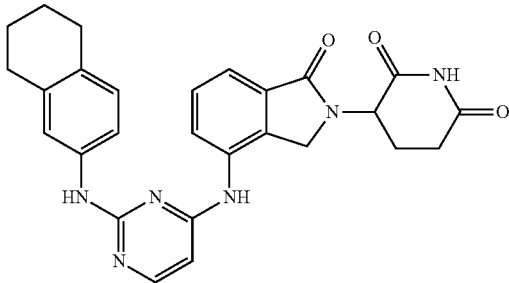

To a solution of 3-(4-((2-chloropyrimidin-4-yl)amino)-1-oxoisoindolin-2-yl)piperidine-2,6-dione (100 mg, 0.27 mmol) and 5,6,7,8-tetrahydronaphthalen-2-amine (40 mg, 0.27 mmol) in $^t$BuOH (2 mL) was added TFA (41 µL, 0.54 mmol), and then the mixture was heated to reflux overnight. The mixture was then concentrated in vacuo and purified by prep-HPLC (MeOH/H$_2$O, 0.05% TFA) to obtain compound 52 (70.4 mg, 44%).

$^1$H NMR (500 MHz, DMSO-d$_6$) δ 10.99 (s, 1H), 10.62 (s, 1H), 10.54 (s, 1H), 8.03 (d, J=7.0 Hz, 1H), 7.85 (d, J=7.9 Hz, 1H), 7.68 (d, J=7.5 Hz, 1H), 7.58 (t, J=7.7 Hz, 1H), 7.09 (d, J=2.2 Hz, 1H), 7.04 (dd, J=8.3, 2.2 Hz, 1H), 6.93 (d, J=8.3 Hz, 1H), 6.46 (d, J=7.0 Hz, 1H), 5.12 (dd, J=13.2, 5.2 Hz, 1H), 4.45 (d, J=17.6 Hz, 1H), 4.29 (d, J=17.5 Hz, 1H), 2.89 (ddd, J=17.3, 13.7, 5.4 Hz, 1H), 2.64 (t, J=6.2 Hz, 2H), 2.55 (d, J=2.6 Hz, 1H), 2.45 (s, 2H), 2.20 (qd, J=13.4, 4.3 Hz, 1H), 1.68 (dd, J=7.6, 4.3 Hz, 4H). LCMS (m/z): 483 [M+H]$^+$.

Example 39: Synthesis of 3-(4-((2-(4-acetylphenyl)pyrimidin-4-yl)amino)-1-oxoisoindolin-2-yl)piperidine-2,6-dione (20)

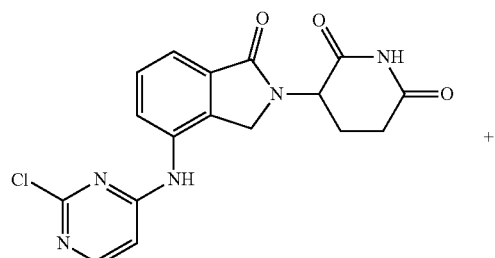

+

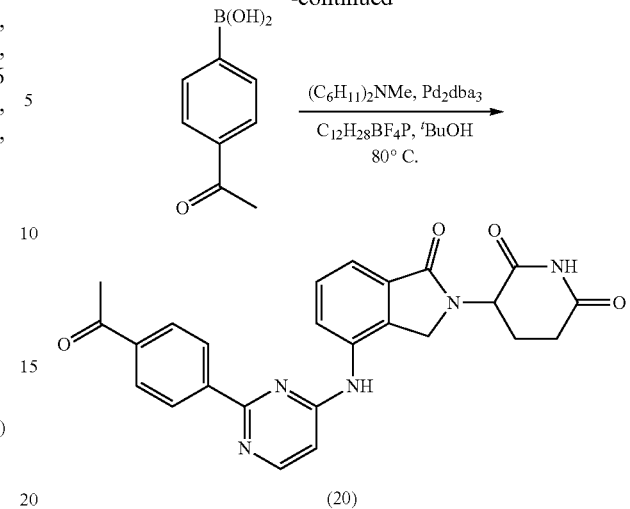

(20)

To a solution of 3-(4-((2-chloropyrimidin-4-yl)amino)-1-oxoisoindolin-2-yl)piperidine-2,6-dione (115 mg, 0.3 mmol) and (4-acetylphenyl)boronic acid (61 mg, 0.36 mmol) in $^t$BuOH (2 mL) were added N,N-dicyclohexylmethylamine (64 mg, 0.33 mmol), Pd$_2$dba$_3$ (27 mg, 0.03 mmol) and Tri-tert-butylphosphonium tetrafluoroborate (18 mg, 0.06 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 20 (10.0 mg, 6%).

$^1$H NMR (500 MHz, DMSO-d$_6$) δ 11.00 (s, 1H), 9.65 (s, 1H), 8.49 (d, J=5.8 Hz, 1H), 8.37 (d, J=8.3 Hz, 2H), 8.13 (d, J=7.8 Hz, 1H), 8.07 (d, J=8.3 Hz, 2H), 7.67-7.53 (m, 2H), 6.87 (d, J=5.9 Hz, 1H), 5.17 (dd, J=13.3, 5.1 Hz, 1H), 4.52 (d, J=17.3 Hz, 1H), 4.43 (d, J=17.3 Hz, 1H), 2.92 (ddd, J=17.2, 13.6, 5.4 Hz, 1H), 2.63 (s, 3H), 2.61-2.55 (m, 1H), 2.35 (qd, J=13.2, 4.4 Hz, 1H), 2.01 (dtd, J=12.7, 5.3, 2.2 Hz, 1H).

LCMS (m/z): 456 [M+H]$^+$.

Example 40: Synthesis of 3-(4-((2-([1,1'-biphenyl]-4-yl)pyrimidin-4-yl)amino)-1-oxoisoindolin-2-yl)piperidine-2,6-dione (31)

(31)

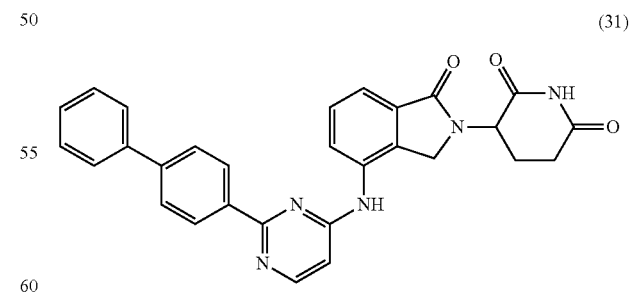

To a solution of 3-(4-((2-chloropyrimidin-4-yl)amino)-1-oxoisoindolin-2-yl)piperidine-2,6-dione (100 mg, 0.27 mmol) and [1,1'-biphenyl]-4-ylboronic acid (80 mg, 0.41 mmol) in $^t$BuOH (2 mL) were added N,N-Dicyclohexylmethylamine (58 mg, 0.30 mmol), Pd$_2$dba$_3$ (25 mg, 0.027 mmol) and Tri-tert-butylphosphonium tetrafluoroborate (16 mg, 0.054 mmol). The mixture was heated to 80° C. and stirred under N₂ atmosphere overnight. The mixture was then filtered, concentrated in vacuo and purified by prep-HPLC (MeOH/H₂O, 0.05% TFA) to obtain compound 31 (4.0 mg, 2%).

¹H NMR (500 MHz, DMSO-d₆) δ 11.01 (s, 1H), 9.99 (s, 1H), 8.47 (d, J=6.1 Hz, 1H), 8.30 (d, J=8.5 Hz, 2H), 8.10 (dd, J=7.3, 1.6 Hz, 1H), 7.85 (d, J=8.5 Hz, 2H), 7.79-7.75 (m, 2H), 7.67-7.61 (m, 2H), 7.51 (dd, J=8.4, 7.0 Hz, 2H), 7.44-7.39 (m, 1H), 6.88 (d, J=6.2 Hz, 1H), 5.18 (dd, J=13.4, 5.1 Hz, 1H), 4.54 (d, J=17.4 Hz, 1H), 4.44 (d, J=17.4 Hz, 1H), 2.92 (ddd, J=18.0, 13.6, 5.4 Hz, 1H), 2.64-2.54 (m, 1H), 2.35 (qd, J=13.2, 4.5 Hz, 1H), 2.07-1.96 (m, 1H).

LCMS (m/z): 490 [M+H]⁺.

Example 41: Synthesis of 3-(4-((2-(3-methoxyphenyl)pyrimidin-4-yl)amino)-1-oxoisoindolin-2-yl)piperidine-2,6-dione (32)

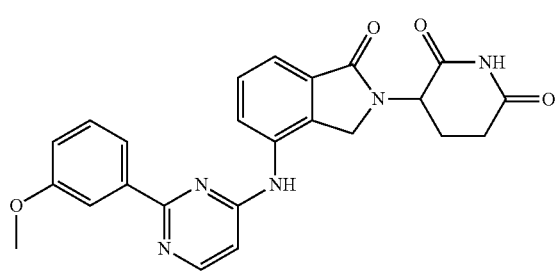

(32)

To a solution of 3-(4-((2-chloropyrimidin-4-yl)amino)-1-oxoisoindolin-2-yl)piperidine-2,6-dione (78 mg, 0.21 mmol) and (3-methoxyphenyl)boronic acid (48 mg, 0.32 mmol) in ᵗBuOH (2 mL) were added N,N-Dicyclohexylmethylamine (45 mg, 0.23 mmol), Pd₂dba₃ (19 mg, 0.021 mmol) and Tri-tert-butylphosphonium tetrafluoroborate (12 mg, 0.042 mmol). The mixture was heated to 80° C. and stirred under N₂ atmosphere overnight. The mixture was then filtered, concentrated in vacuo and purified by prep-HPLC (MeOH/H₂O, 0.05% TFA) to obtain compound 32 (13.7 mg, 12%).

¹H NMR (500 MHz, DMSO-d₆) δ 11.19 (s, 1H), 11.02 (s, 1H), 8.44 (d, J=7.1 Hz, 1H), 7.96 (d, J=7.8 Hz, 1H), 7.86 (d, J=7.8 Hz, 1H), 7.73 (dd, J=7.5, 1.1 Hz, 1H), 7.67 (td, J=7.8, 7.3, 1.3 Hz, 2H), 7.32 (dd, J=8.5, 0.9 Hz, 1H), 7.17 (td, J=7.5, 1.0 Hz, 1H), 7.06 (d, J=6.9 Hz, 1H), 5.18 (dd, J=13.3, 5.1 Hz, 1H), 4.52 (d, J=17.6 Hz, 1H), 4.42 (d, J=17.6 Hz, 1H), 3.98 (s, 3H), 2.93 (ddd, J=17.3, 13.7, 5.4 Hz, 1H), 2.64-2.55 (m, 1H), 2.38-2.29 (m, 1H), 2.00 (ddq, J=10.3, 5.4, 3.1, 2.6 Hz, 1H).

LCMS (m/z): 444 [M+H]⁺.

Example 42: Synthesis of 3-(4-((2-(4-fluoro-2-methoxyphenyl)pyrimidin-4-yl)amino)-1-oxoisoindolin-2-yl)piperidine-2,6-dione (33)

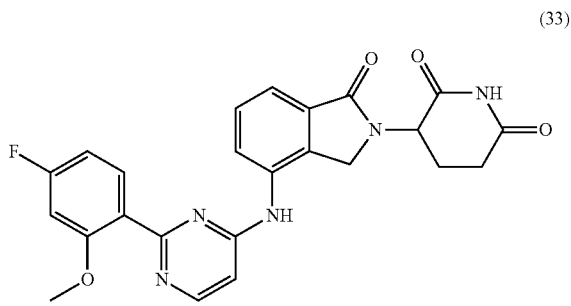 [SMILES: COc1cc(F)ccc1-c1nccc(Nc2cccc3c2CN(C2CCC(=O)NC2=O)C3=O)n1]

(33)

To a solution of 3-(4-((2-chloropyrimidin-4-yl)amino)-1-oxoisoindolin-2-yl)piperidine-2,6-dione (96 mg, 0.26 mmol) and (4-fluoro-2-methoxyphenyl)boronic acid (66 mg, 0.39 mmol) in ᵗBuOH (2 mL) were added N,N-Dicyclohexylmethylamine (56 mg, 0.29 mmol), Pd₂dba₃ (22 mg, 0.026 mmol) and Tri-tert-butylphosphonium tetrafluoroborate (15 mg, 0.052 mmol). The mixture was heated to 80° C. and stirred under N₂ atmosphere overnight. The mixture was then filtered, concentrated in vacuo and purified by prep-HPLC (MeOH/H₂O, 0.05% TFA) to obtain compound 33 (17.1 mg, 11%).

¹H NMR (500 MHz, DMSO-d₆) δ 11.14 (s, 1H), 11.03 (s, 1H), 8.43 (d, J=7.0 Hz, 1H), 7.94 (d, J=7.8 Hz, 1H), 7.89 (dd, J=8.8, 6.7 Hz, 1H), 7.72 (dd, J=7.6, 1.0 Hz, 1H), 7.66 (t, J=7.7 Hz, 1H), 7.26 (dd, J=11.3, 2.4 Hz, 1H), 7.03 (td, J=8.5, 4.1 Hz, 2H), 5.18 (dd, J=13.3, 5.1 Hz, 1H), 4.50 (d, J=17.6 Hz, 1H), 4.41 (d, J=17.6 Hz, 1H), 3.98 (s, 3H), 2.93 (ddd, J=17.3, 13.6, 5.4 Hz, 1H), 2.64-2.56 (m, 1H), 2.33 (qd, J=13.2, 4.4 Hz, 1H), 2.00 (dtd, J=12.6, 5.1, 2.1 Hz, 1H).

LCMS (m/z): 462 [M+H]⁺.

Example 43: Synthesis of 3-(4-((2-(2,4-dimethoxyphenyl)pyrimidin-4-yl)amino)-1-oxoisoindolin-2-yl)piperidine-2,6-dione (35)

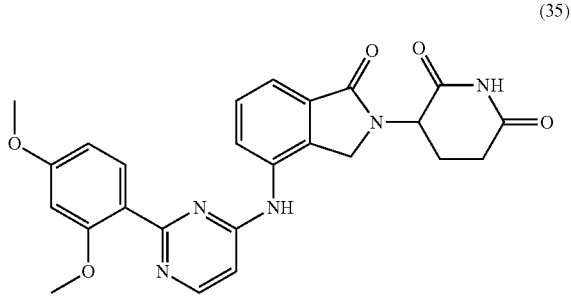 [SMILES: COc1ccc(-c2nccc(Nc3cccc4c3CN(C3CCC(=O)NC3=O)C4=O)n2)c(OC)c1]

(35)

To a solution of 3-(4-((2-chloropyrimidin-4-yl)amino)-1-oxoisoindolin-2-yl)piperidine-2,6-dione (100 mg, 0.27 mmol) and (2,4-dimethoxyphenyl)boronic acid (74 mg, 0.41 mmol) in ᵗBuOH (2 mL) were added N,N-Dicyclohexylmethylamine (58 mg, 0.30 mmol), Pd₂dba₃ (25 mg, 0.027 mmol) and Tri-tert-butylphosphonium tetrafluoroborate (16 mg, 0.054 mmol). The mixture was heated to 80° C. and stirred under N₂ atmosphere overnight. The mixture was then filtered, concentrated in vacuo and purified by prep-HPLC (MeOH/H$_2$O, 0.05% TFA) to obtain compound 35 (9.3 mg, 6%).

$^1$H NMR (500 MHz, DMSO-d$_6$) δ 11.11 (s, 1H), 11.02 (s, 1H), 8.35 (d, J=7.1 Hz, 1H), 7.93 (d, J=8.5 Hz, 2H), 7.74 (d, J=7.5 Hz, 1H), 7.68 (t, J=7.7 Hz, 1H), 6.99 (s, 1H), 6.82 (d, J=2.3 Hz, 1H), 6.80-6.76 (m, 1H), 5.18 (dd, J=13.3, 5.1 Hz, 1H), 4.51 (d, J=17.6 Hz, 1H), 4.40 (d, J=17.6 Hz, 1H), 4.03 (s, 3H), 3.89 (s, 3H), 2.92 (ddd, J=17.3, 13.6, 5.4 Hz, 1H), 2.63-2.55 (m, 1H), 2.33 (qd, J=12.9, 4.2 Hz, 1H), 2.00 (td, J=6.0, 2.3 Hz, 1H).

LCMS (m/z): 474 [M+H]$^+$.

Example 44: Synthesis of 3-(4-((2-(benzofuran-2-yl)pyrimidin-4-yl)amino)-1-oxoisoindolin-2-yl)piperidine-2,6-dione (36)

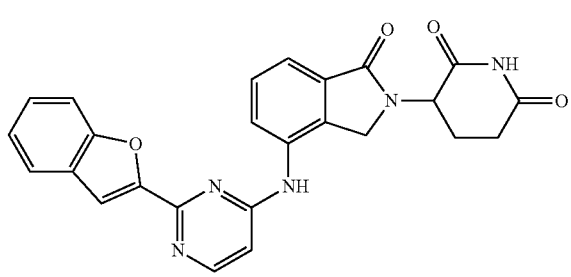

(36)

To a solution of 3-(4-((2-chloropyrimidin-4-yl)amino)-1-oxoisoindolin-2-yl)piperidine-2,6-dione (100 mg, 0.27 mmol) and benzofuran-2-ylboronic acid (65 mg, 0.41 mmol) in $^t$BuOH (2 mL) were added N,N-Dicyclohexylmethylamine (58 mg, 0.30 mmol), Pd$_2$dba$_3$ (25 mg, 0.027 mmol) and Tri-tert-butylphosphonium tetrafluoroborate (16 mg, 0.054 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 36 (5.0 mg, 3%).

$^1$H NMR (500 MHz, DMSO-d$_6$) δ 10.99 (s, 1H), 9.75 (s, 1H), 8.44 (d, J=5.9 Hz, 1H), 8.08 (d, J=7.7 Hz, 1H), 7.78 (dt, J=7.8, 1.0 Hz, 1H), 7.68 (dq, J=8.3, 0.9 Hz, 1H), 7.63 (t, J=7.6 Hz, 1H), 7.61-7.57 (m, 2H), 7.43 (ddd, J=8.4, 7.2, 1.4 Hz, 1H), 7.34-7.30 (m, 1H), 6.83 (d, J=6.0 Hz, 1H), 5.16 (dd, J=13.2, 5.1 Hz, 1H), 4.60 (d, J=17.4 Hz, 1H), 4.44 (d, J=17.4 Hz, 1H), 2.90 (ddd, J=17.3, 13.6, 5.4 Hz, 1H), 2.59-2.53 (m, 1H), 2.37 (ddd, J=15.6, 12.4, 4.5 Hz, 1H), 2.03 (ddq, J=10.6, 5.6, 3.3, 2.7 Hz, 1H).

LCMS (m/z): 454 [M+H]$^+$.

Example 45: Synthesis of 3-(4-((2-(4-fluorophenyl)pyrimidin-4-yl)amino)-1-oxoisoindolin-2-yl)piperidine-2,6-dione (39)

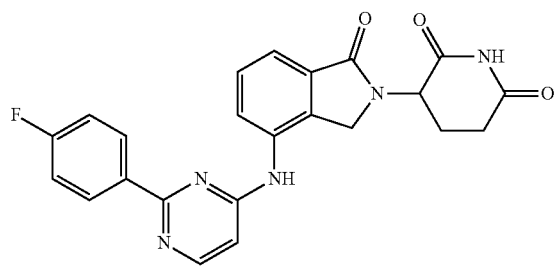

(39)

To a solution of 3-(4-((2-chloropyrimidin-4-yl)amino)-1-oxoisoindolin-2-yl)piperidine-2,6-dione (60 mg, 0.16 mmol) and (4-fluorophenyl)boronic acid (34 mg, 0.24 mmol) in $^t$BuOH (2 mL) were added N,N-Dicyclohexylmethylamine (34 mg, 0.18 mmol), Pd$_2$dba$_3$ (15 mg, 0.016 mmol) and Tri-tert-butylphosphonium tetrafluoroborate (10 mg, 0.032 mmol). The mixture was heated to 80° C. and stirred under N$_2$ atmosphere overnight. The mixture was then filtered, concentrated in vacuo and purified by prep-HPLC (MeOH/H$_2$O, 0.05% TFA) to obtain compound 39 (1.5 mg, 2%).

$^1$H NMR (500 MHz, DMSO-d$_6$) δ 11.01 (s, 1H), 9.96 (s, 1H), 8.44 (d, J=6.1 Hz, 1H), 8.25 (dd, J=8.6, 5.7 Hz, 1H), 8.04 (dd, J=7.0, 1.9 Hz, 1H), 7.84 (dd, J=8.3, 6.3 Hz, 1H), 7.62 (d, J=7.0 Hz, 2H), 7.36 (t, J=8.7 Hz, 1H), 7.15 (t, J=8.9 Hz, 1H), 6.86 (d, J=6.1 Hz, 1H), 5.17 (dd, J=13.3, 5.1 Hz, 1H), 4.50 (d, J=17.4 Hz, 1H), 4.42 (d, J=17.4 Hz, 1H), 2.92 (ddd, J=18.2, 13.5, 5.4 Hz, 1H), 2.66-2.55 (m, 1H), 2.34 (qd, J=13.3, 4.6 Hz, 1H), 2.03-1.97 (m, 1H).

LCMS (m/z): 432 [M+H]$^+$.

Example 46: Synthesis of 3-(4-((2-((2,3-dihydro-1H-inden-5-yl)amino)-9-isopropyl-9H-purin-6-yl)amino)-1-oxoisoindolin-2-yl)piperidine-2,6-dione (53)

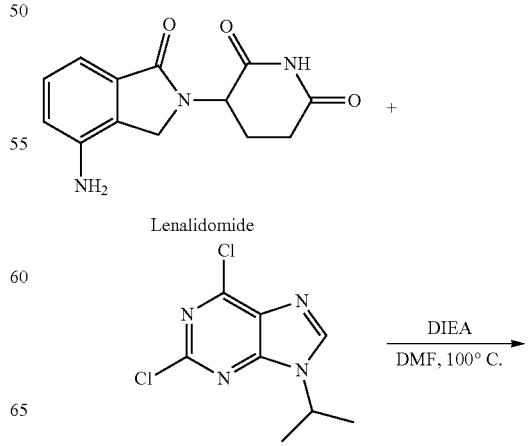

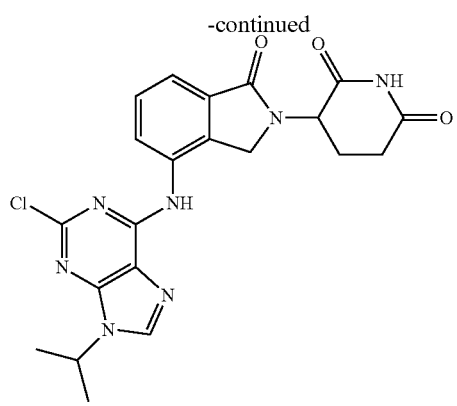

+

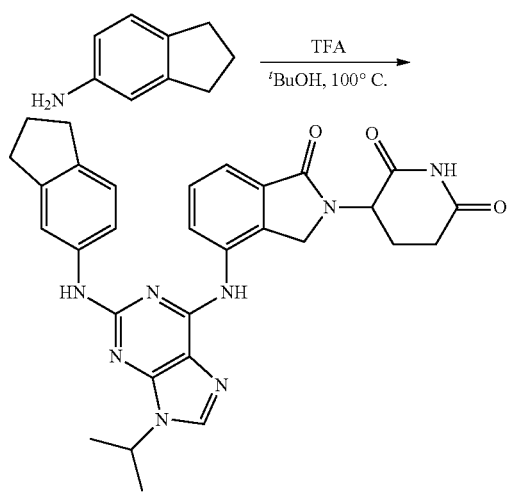

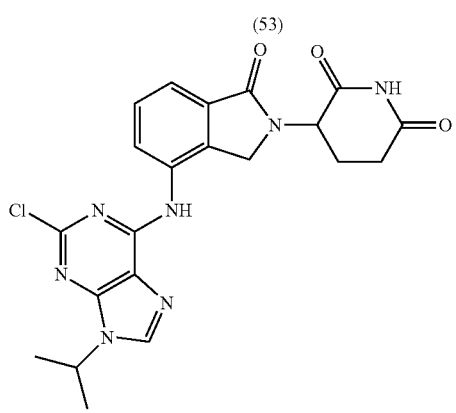

3-(4-((2-chloro-9-isopropyl-9H-purin-6-yl)amino)-1-oxoisoindolin-2-yl)piperidine-2,6-dione To a solution of Lenalidomide (78 mg, 0.34 mmol) and 2,6-dichloro-9-isopropyl-9H-purine (88 mg, 0.34 mmol) in DMF (2 mL) was added DIEA (169 μL, 1.02 mmol), and then the mixture was heated to 100° C. overnight. The mixture was then concentrated in vacuo and purified by prep-HPLC (MeOH/H$_2$O, 0.05% TFA) to obtain the title compound.

LCMS (m/z): 454 [M+H]$^+$.

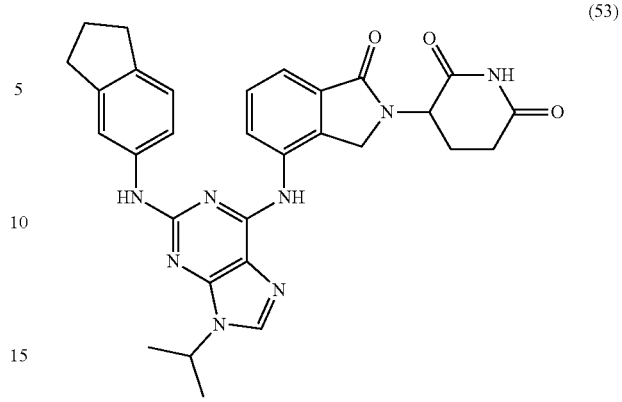

To a solution of 3-(4-((2-chloro-9-isopropyl-9H-purin-6-yl)amino)-1-oxoisoindolin-2-yl)piperidine-2,6-dione (60 mg, 0.13 mmol) and 2,3-dihydro-1H-inden-5-amine (18 mg, 0.13 mmol) in $^t$BuOH (1 mL) was added TFA (20 μL, 0.26 mmol), and then the mixture was heated to reflux overnight. The mixture was then concentrated in vacuo and purified by prep-HPLC (MeOH/H$_2$O, 0.05% TFA) to obtain compound 53 (19.8 mg, 23%).

$^1$H NMR (500 MHz, DMSO-d$_6$) δ 10.93 (s, 1H), 9.74 (s, 1H), 9.03 (s, 1H), 8.31 (s, 1H), 7.85 (d, J=7.7 Hz, 1H), 7.69-7.50 (m, 3H), 7.28 (d, J=8.3 Hz, 1H), 6.96 (d, J=8.2 Hz, 1H), 5.08 (dd, J=13.2, 5.2 Hz, 1H), 4.78-4.68 (m, 1H), 4.57 (d, J=17.3 Hz, 1H), 4.34 (d, J=17.3 Hz, 1H), 2.85 (ddd, J=18.3, 13.6, 5.4 Hz, 1H), 2.74 (t, J=7.3 Hz, 2H), 2.64 (t, J=7.5 Hz, 2H), 2.48 (s, 1H), 2.20 (dd, J=13.3, 4.5 Hz, 1H), 1.98-1.88 (m, 2H), 1.74-1.67 (m, 1H), 1.57 (d, J=6.7 Hz, 6H).

LCMS (m/z): 551 [M+H]$^+$.

Example 47: Synthesis of 3-(4-((9-isopropyl-2-((5,6,7,8-tetrahydronaphthalen-2-yl)amino)-9H-purin-6-yl)amino)-1-oxoisoindolin-2-yl)piperidine-2,6-dione (55)

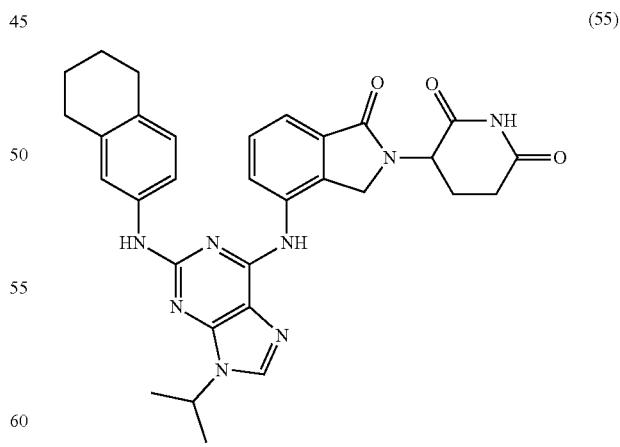

To a solution of 3-(4-((2-chloro-9-isopropyl-9H-purin-6-yl)amino)-1-oxoisoindolin-2-yl)piperidine-2,6-dione (45 mg, 0.1 mmol) and 5,6,7,8-tetrahydronaphthalen-2-amine (15 mg, 0.1 mmol) in $^t$BuOH (1 mL) was added TFA (15 μL, 0.2 mmol), and then the mixture was heated to reflux overnight. The mixture was then concentrated in vacuo and purified by prep-HPLC (MeOH/H$_2$O, 0.05% TFA) to obtain compound 55 (11.0 mg, 16%).

$^1$H NMR (500 MHz, DMSO-d$_6$) δ 10.94 (s, 1H), 9.82 (s, 1H), 9.01 (s, 1H), 8.40 (s, 1H), 7.91 (d, J=7.6 Hz, 1H), 7.63-7.50 (m, 2H), 7.41 (s, 1H), 7.26 (dd, J=8.3, 2.3 Hz, 1H), 6.80 (d, J=8.3 Hz, 1H), 5.08 (dd, J=13.2, 5.1 Hz, 1H), 4.71 (p, J=6.8 Hz, 1H), 4.59 (d, J=17.3 Hz, 1H), 4.35 (d, J=17.3 Hz, 1H), 3.08 (qd, J=7.3, 4.7 Hz, 4H), 2.91-2.81 (m, 1H), 2.56-2.52 (m, 1H), 1.77 (d, J=12.2 Hz, 1H), 1.68 (t, J=3.3 Hz, 4H), 1.58 (d, J=6.7 Hz, 6H).

LCMS (m/z): 565 [M+H]$^+$.

Example 48: Synthesis of 3-(4-((9-isopropyl-2-(mesitylamino)-9H-purin-6-yl)amino)-1-oxoisoindolin-2-yl)piperidine-2,6-dione (56)

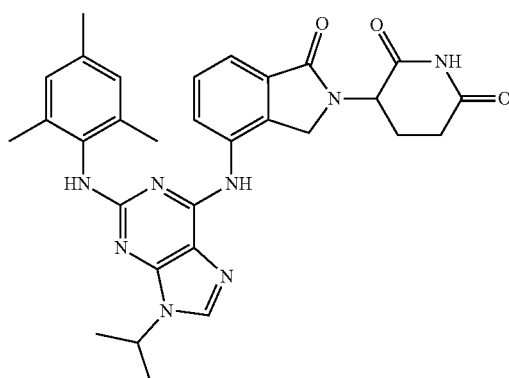

(56)

To a solution of 3-(4-((2-chloro-9-isopropyl-9H-purin-6-yl)amino)-1-oxoisoindolin-2-yl)piperidine-2,6-dione (45 mg, 0.1 mmol) and 2,4,6-trimethylaniline (14 mg, 0.1 mmol) in $^t$BuOH (1 mL) was added TFA (15 μL, 0.2 mmol), and then the mixture was heated to reflux overnight. The mixture was then concentrated in vacuo and purified by prep-HPLC (MeOH/H$_2$O, 0.05% TFA) to obtain compound 56 (0.5 mg, 0.8%).

LCMS (m/z): 553 [M+H]$^+$.

Example 49: Synthesis of 3-(4-((2-(2-methoxyphenyl)-9H-purin-6-yl)amino)-1-oxoisoindolin-2-yl)piperidine-2,6-dione (47)

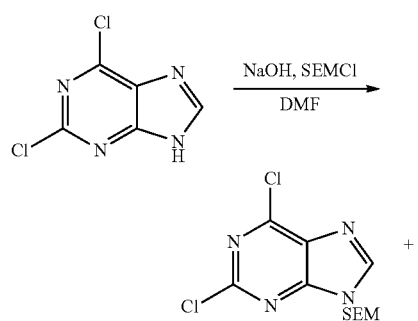

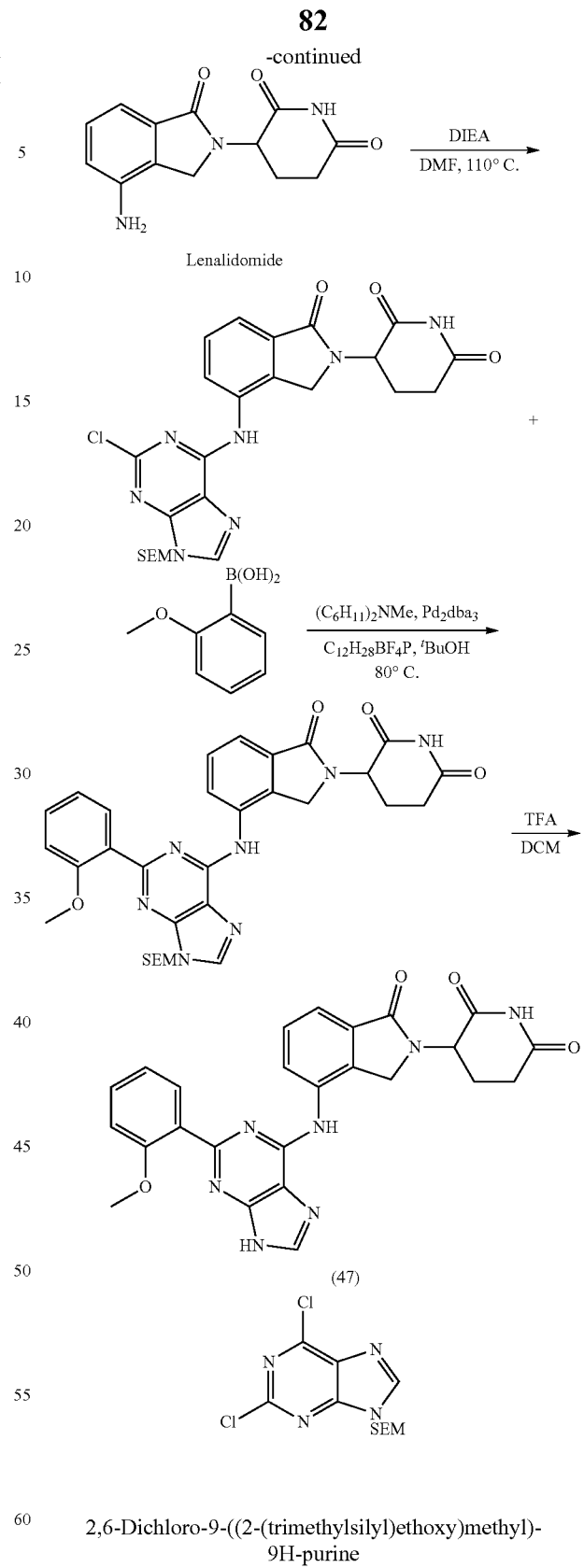

2,6-Dichloro-9-((2-(trimethylsilyl)ethoxy)methyl)-9H-purine

To a solution of 2,6-dichloro-9H-purine (1.89 g, 10 mmol) and NaOH (1.2 g, 30 mmol) in DMF (30 mL) was added 2-(Trimethylsilyl)ethoxymethyl chloride (3.5 mL, 20 mmol), and then the mixture was stirred for 4h. The mixture was then extracted with EtOAc, washed with brine, dried over Na$_2$SO$_4$, and concentrated in vacuo to the next step without any purification.

LCMS (m/z): 319 [M+H]$^+$.

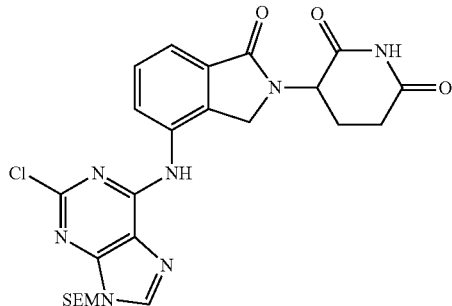 [SMILES: C[Si](C)(C)CCOCn1cnc2c(Nc3cccc4c3CN(C3CCC(=O)NC3=O)C4=O)nc(Cl)nc21]

3-(4-((2-Chloro-9-((2-(trimethylsilyl)ethoxy)
methyl)-9H-purin-6-yl)amino)-1-oxoisoindolin-2-yl)
piperidine-2,6-dione To a solution of 2,6-dichloro-9-((2-(trimethylsilyl) ethoxy)methyl)-9H-purine (10 mmol) and lenalidomide (2.6 g, 10 mmol) in DMF (30 mL) was added DIEA (3.3 mL, 20 mmol), and then heated up to 110° C., stirred overnight. The mixture was purified by silica gel (MeOH/DCM=0-4%) directly to provide the title compound (1.0 g, 19% for 2 steps) as a yellow solid.

LCMS (m/z): 542 [M+H]$^+$.

(47)

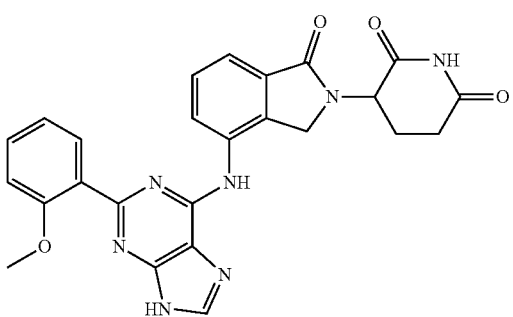

To a solution of 3-(4-((2-chloro-9-((2-(trimethylsilyl) ethoxy)methyl)-9H-purin-6-yl)amino)-1-oxoisoindolin-2-yl)piperidine-2,6-dione (83 mg, 0.15 mmol) and (2-methoxyphenyl)boronic acid (27 mg, 0.18 mmol) in $^t$BuOH (2 mL) were added N,N-Dicyclohexylmethylamine (32 mg, 0.17 mmol), Pd$_2$dba$_3$ (14 mg, 0.015 mmol) and Tri-tert-butylphosphonium tetrafluoroborate (9 mg, 0.03 mmol). The mixture was heated to 80° C. and stirred under N$_2$ atmosphere overnight. The mixture was then filtered, concentrated in vacuo and purified by silica gel (MeOH/DCM=0-4%) to provide the intermediate. The intermediate was then concentrated in vacuo, dissolved in TFA/DCM=1/1, stirred for 2h, and then concentrated again in vacuo, purified by prep-HPLC (MeOH/H$_2$O, 0.05% TFA) to provide compound 47 (26.0 mg, 29%).

$^1$H NMR (500 MHz, DMSO-d$_6$) δ 10.99 (s, 1H), 8.50 (s, 1H), 8.05 (dd, J=6.9, 2.1 Hz, 1H), 7.62-7.50 (m, 4H), 7.45 (ddd, J=8.9, 7.5, 1.8 Hz, 1H), 7.17-7.12 (m, 1H), 7.04 (td, J=7.5, 0.9 Hz, 1H), 5.15 (dd, J=13.3, 5.1 Hz, 1H), 4.60 (d, J=17.5 Hz, 1H), 4.45 (d, J=17.4 Hz, 1H), 2.92 (ddd, J=17.2, 13.6, 5.4 Hz, 1H), 2.60 (d, J=3.3 Hz, 1H), 2.55 (s, 3H), 2.32 (qd, J=13.3, 4.6 Hz, 1H), 1.95 (dt, J=10.0, 4.0 Hz, 1H).

LCMS (m/z): 484 [M+H]$^+$.

Example 50: Synthesis of 3-(4-((2-([1,1'-biphenyl]-4-yl)-9H-purin-6-yl)amino)-1-oxoisoindolin-2-yl) piperidine-2,6-dione (48)

(48)

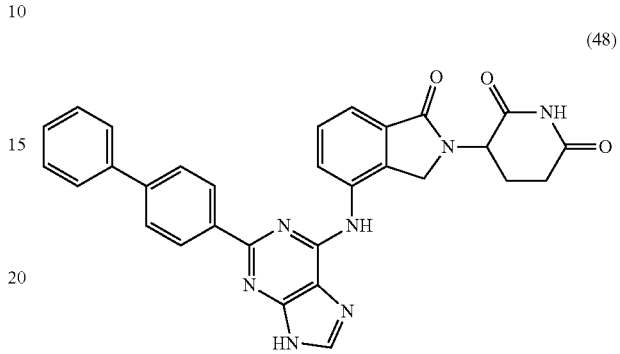

To a solution of 3-(4-((2-chloro-9-((2-(trimethylsilyl) ethoxy)methyl)-9H-purin-6-yl)amino)-1-oxoisoindolin-2-yl)piperidine-2,6-dione (72 mg, 0.13 mmol) and [1,1'-biphenyl]-4-ylboronic acid (32 mg, 0.16 mmol) in $^t$BuOH (2 mL) were added N,N-Dicyclohexylmethylamine (27 mg, 0.14 mmol), Pd$_2$dba$_3$ (12 mg, 0.013 mmol) and Tri-tert-butylphosphonium tetrafluoroborate (8 mg, 0.026 mmol). The mixture was heated to 80° C. and stirred under N$_2$ atmosphere overnight. The mixture was then filtered, concentrated in vacuo and purified by silica gel (MeOH/DCM=0-4%) to provide the intermediate. The intermediate was then concentrated in vacuo, dissolved in TFA/DCM=1/1, stirred for 2h, and then concentrated again, purified by prep-HPLC (MeOH/H$_2$O, 0.05% TFA) to provide compound 48 (1.7 mg, 2%).

$^1$H NMR (500 MHz, DMSO-d$_6$) δ 10.94 (s, 1H), 9.91 (s, 1H), 8.36-8.24 (m, 3H), 8.01-7.96 (m, 1H), 7.75 (dd, J=9.9, 7.9 Hz, 4H), 7.64-7.59 (m, 2H), 7.49 (dd, J=8.3, 7.1 Hz, 2H), 7.42-7.35 (m, 1H), 5.13 (dd, J=13.1, 5.1 Hz, 1H), 4.64 (d, J=17.4 Hz, 1H), 4.51 (d, J=17.4 Hz, 1H), 2.93-2.78 (m, 1H), 2.51 (d, J=1.9 Hz, 1H), 2.34 (qd, J=13.2, 4.8 Hz, 1H), 1.96 (dd, J=14.9, 8.4 Hz, 1H).

LCMS (m/z): 530 [M+H]$^+$.

Example 51: Synthesis of 3-(4-((2-(4-fluoro-2-methoxyphenyl)-9H-purin-6-yl)amino)-1-oxoisoindolin-2-yl)piperidine-2,6-dione (49)

(49)

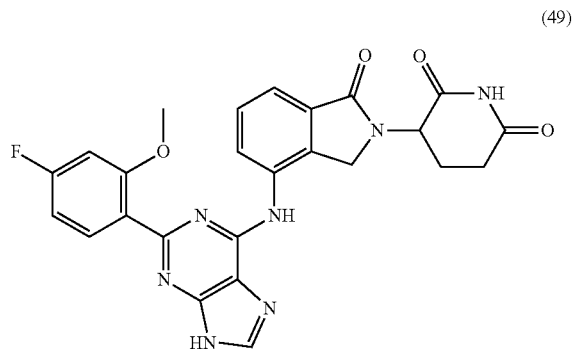 [SMILES: COc1cc(F)ccc1-c1nc(Nc2cccc3c2CN(C2CCC(=O)NC2=O)C3=O)c2nc[nH]c2n1]

To a solution of 3-(4-((2-chloro-9-((2-(trimethylsilyl)ethoxy)methyl)-9H-purin-6-yl)amino)-1-oxoisoindolin-2-yl)piperidine-2,6-dione (82 mg, 0.15 mmol) and (4-fluoro-2-methoxyphenyl)boronic acid (31 mg, 0.18 mmol) in ᵗBuOH (2 mL) were added N,N-Dicyclohexylmethylamine (32 mg, 0.17 mmol), Pd₂dba₃ (14 mg, 0.015 mmol) and Tri-tert-butylphosphonium tetrafluoroborate (9 mg, 0.03 mmol). The mixture was heated to 80° C. and stirred under N₂ atmosphere overnight. The mixture was then filtered, concentrated in vacuo and purified by silica gel (MeOH/DCM=0-4%) to provide the intermediate. The intermediate was then concentrated in vacuo, dissolved in TFA/DCM=1/1, stirred for 2h, and then concentrated again, purified by prep-HPLC (MeOH/H₂O, 0.05% TFA) to provide compound 49 (16.4 mg, 18%).

¹H NMR (500 MHz, DMSO-d₆) δ 10.98 (s, 1H), 9.74 (s, 1H), 8.30 (s, 1H), 8.11-7.99 (m, 1H), 7.58-7.48 (m, 3H), 6.98 (dd, J=11.6, 2.4 Hz, 1H), 6.82 (td, J=8.4, 2.4 Hz, 1H), 5.13 (dd, J=13.3, 5.1 Hz, 1H), 4.59 (d, J=17.4 Hz, 1H), 4.45 (d, J=17.3 Hz, 1H), 3.77 (s, 3H), 2.91 (ddd, J=17.9, 13.5, 5.4 Hz, 1H), 2.63-2.55 (m, 1H), 2.36 (qd, J=13.2, 4.5 Hz, 1H), 1.94 (d, J=12.8 Hz, 1H).

LCMS (m/z): 502 [M+H]⁺.

Example 52: Synthesis of 3-(4-((2-(4-fluorophenyl)-9H-purin-6-yl)amino)-1-oxoisoindolin-2-yl)piperidine-2,6-dione (50)

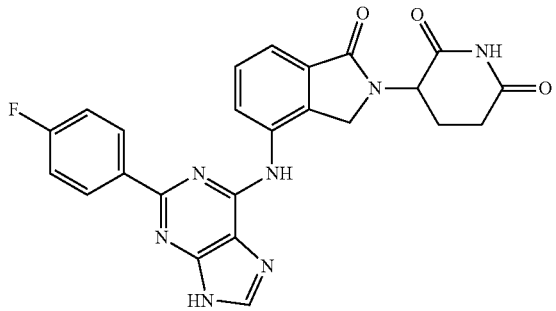

(50)

To a solution of 3-(4-((2-chloro-9-((2-(trimethylsilyl)ethoxy)methyl)-9H-purin-6-yl)amino)-1-oxoisoindolin-2-yl)piperidine-2,6-dione (82 mg, 0.15 mmol) and (4-fluorophenyl)boronic acid (25 mg, 0.18 mmol) in ᵗBuOH (2 mL) were added N,N-Dicyclohexylmethylamine (32 mg, 0.17 mmol), Pd₂dba₃ (14 mg, 0.015 mmol) and Tri-tert-butylphosphonium tetrafluoroborate (9 mg, 0.03 mmol). The mixture was heated to 80° C. and stirred under N₂ atmosphere overnight. The mixture was then filtered, concentrated in vacuo and purified by silica gel (MeOH/DCM=0-4%) to provide the intermediate. The intermediate was then concentrated in vacuo, dissolved in TFA/DCM=1/1, stirred for 2h, and then concentrated again, purified by prep-HPLC (MeOH/H₂O, 0.05% TFA) to provide compound 50 (6.3 mg, 7%).

¹H NMR (500 MHz, DMSO-d₆) δ 10.94 (s, 1H), 9.89 (s, 1H), 8.34 (s, 1H), 8.27-8.20 (m, 2H), 7.95 (dd, J=6.0, 2.9 Hz, 1H), 7.61 (q, J=3.9, 3.1 Hz, 2H), 7.31-7.19 (m, 2H), 5.13 (dd, J=13.2, 5.1 Hz, 1H), 4.58 (d, J=17.4 Hz, 1H), 4.48 (d, J=17.3 Hz, 1H), 2.88 (ddd, J=18.0, 11.5, 5.4 Hz, 1H), 2.55 (s, 1H), 2.33 (qd, J=13.1, 4.4 Hz, 1H), 2.01-1.91 (m, 1H).

LCMS (m/z): 472 [M+H]⁺.

Example 53: Synthesis of 3-(4-((2-(3,5-dimethoxyphenyl)-9H-purin-6-yl)amino)-1-oxoisoindolin-2-yl)piperidine-2,6-dione (51)

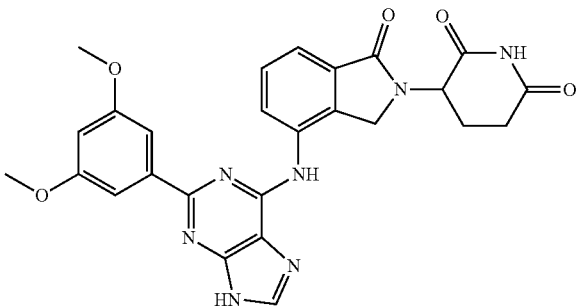

(51)

To a solution of 3-(4-((2-chloro-9-((2-(trimethylsilyl)ethoxy)methyl)-9H-purin-6-yl)amino)-1-oxoisoindolin-2-yl)piperidine-2,6-dione (90 mg, 0.17 mmol) and (3,5-dimethoxyphenyl)boronic acid (36 mg, 0.2 mmol) in ᵗBuOH (2 mL) were added N,N-Dicyclohexylmethylamine (36 mg, 0.18 mmol), Pd₂dba₃ (15 mg, 0.017 mmol) and Tri-tert-butylphosphonium tetrafluoroborate (10 mg, 0.03 mmol). The mixture was heated to 80° C. and stirred under N₂ atmosphere overnight. The mixture was then filtered, concentrated in vacuo and purified by silica gel (MeOH/DCM=0-4%) to provide the intermediate. The intermediate was then concentrated in vacuo, dissolved in TFA/DCM=1/1, stirred for 2h, and then concentrated again in vacuo, purified by prep-HPLC (MeOH/H₂O, 0.05% TFA) to provide compound 51 (4.5 mg, 4%).

LCMS (m/z): 514 [M+H]⁺.

Example 54: Synthesis of 4-(3-((2-((2,3-dihydro-1H-inden-5-yl)amino)pyrimidin-4-yl)amino)propyl)-2-(2,6-dioxopiperidin-3-yl)isoindoline-1,3-dione (57)

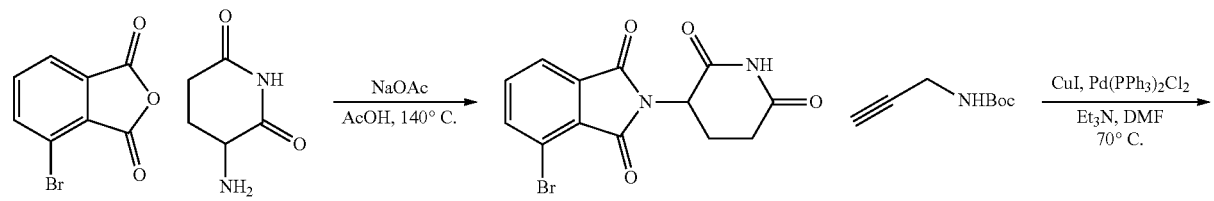

87
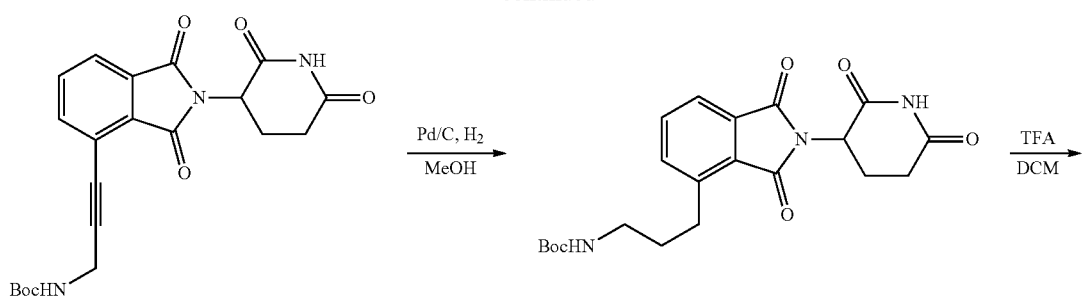
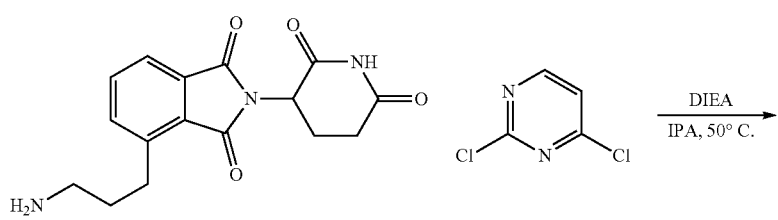
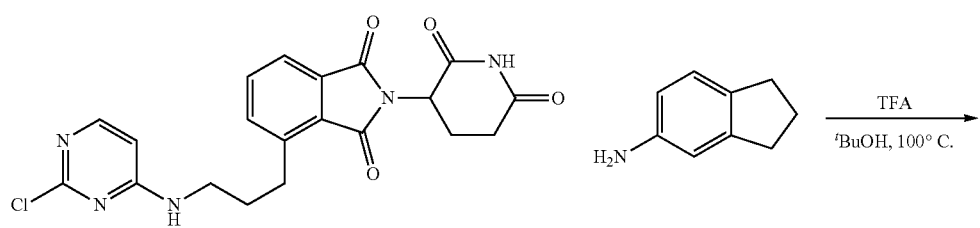
88
-continued
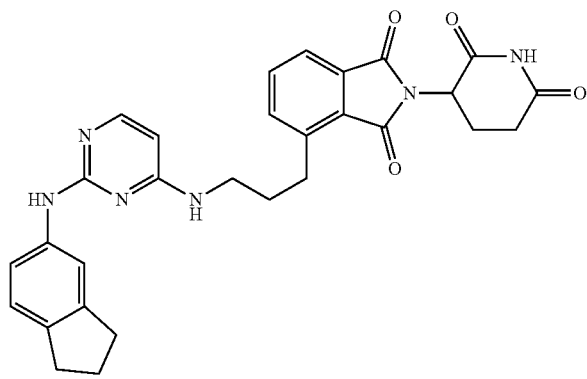
(57)
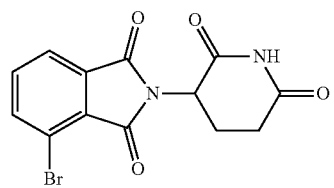

4-bromo-2-(2,6-dioxopiperidin-3-yl)isoindoline-1,3-dione

To a solution of 4-bromoisobenzofuran-1,3-dione (2.27 g, 10 mml) and 3-aminopiperidine-2,6-dione hydrochloride (1.8 g, 11 mmol) in AcOH (30 mL) was added NaOAc (984 mg, 12 mmol), then the mixture was heated to reflux at 140° C. overnight. The mixture was allowed to cool down, then the mixture was filtered, washed with water, and then dried over air to provide the crude product without any purification.

LCMS (m/z): 337 [M+H]$^+$.

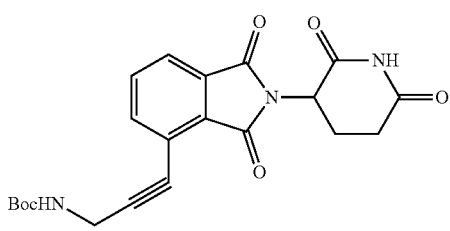 [SMILES: CC(C)(C)OC(=O)NCC#Cc1cccc2c1C(=O)N(C1CCC(=O)NC1=O)C2=O]

tert-Butyl (3-(2-(2,6-dioxopiperidin-3-yl)-1,3-di-oxoisoindolin-4-yl)prop-2-yn-1-yl)carbamate To a solution of 4-bromo-2-(2,6-dioxopiperidin-3-yl) isoindoline-1,3-dione (336 mg, 1 mmol) and tert-butyl prop-2-yn-1-ylcarbamate (310 mg, 2 mmol) in DMF (5 mL) were added CuI (38 mg, 0.2 mmol), Et$_3$N (2.5 mL) and Pd(PPh$_3$)$_2$Cl$_2$ (70 mg, 0.1 mmol). The resulting mixture was then heated up to 70° C. and stirred under N$_2$ atmosphere for 3h. The mixture was then filtered, concentrated in vacuo, and purified by silica gel (MeOH/DCM=0-4%) to obtain the title compound.

LCMS (m/z): 412 [M+H]$^+$.

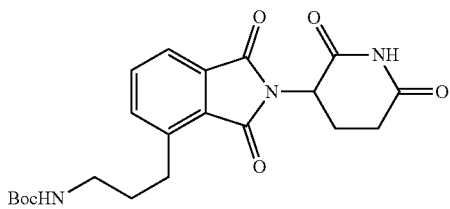 [SMILES: CC(C)(C)OC(=O)NCCCc1cccc2c1C(=O)N(C1CCC(=O)NC1=O)C2=O]

tert-Butyl (3-(2-(2,6-dioxopiperidin-3-yl)-1,3-di-oxoisoindolin-4-yl)propyl)carbamate To a solution of tert-butyl (3-(2-(2,6-dioxopiperidin-3-yl)-1,3-dioxoisoindolin-4-yl)prop-2-yn-1-yl)carbamate in MeOH was added Pd/C (10 wt. % loading, matrix carbon), then the mixture was hydrogenated at room temperature overnight. The reaction mixture was filtered and the filtrate was concentrated in vacuo to provide the title compound.

LCMS (m/z): 415 [M+H]$^+$.

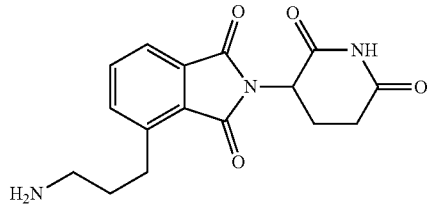 [SMILES: NCCCc1cccc2c1C(=O)N(C1CCC(=O)NC1=O)C2=O]

4-(3-Aminopropyl)-2-(2,6-dioxopiperidin-3-yl)isoin-doline-1,3-dione

A solution of tert-butyl (3-(2-(2,6-dioxopiperidin-3-yl)-1,3-dioxoisoindolin-4-yl)propyl)carbamate in TFA/DCM=1/2 (v/v) was stirred at room temperature for 3 h, and then concentrated in vacuo. The crude title compound was used in the next step without any purification.

LCMS (m/z): 315 [M+H]$^+$.

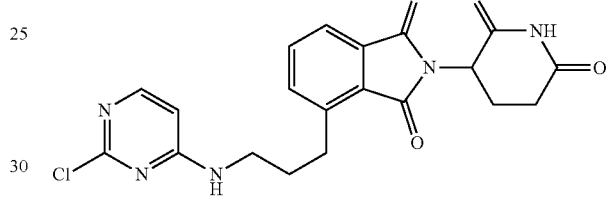

4-(3-((2-chloropyrimidin-4-yl)amino)propyl)-2-(2,6-dioxopiperidin-3-yl)isoindoline-1,3-dione To a solution of 4-(3-aminopropyl)-2-(2,6-dioxopiperi-din-3-yl)isoindoline-1,3-dione and 2,4-dichloropyrimidine (1 eq) in isopropanol was added DIEA (3 eq), and then the mixture was stirred at 50° C. for 3h. The mixture was then concentrated in vacuo, purified by silica gel (MeOH/DCM=0-10%) to provide the title compound (115 mg).

LCMS (m/z): 428 [M+H]$^+$.

(57)

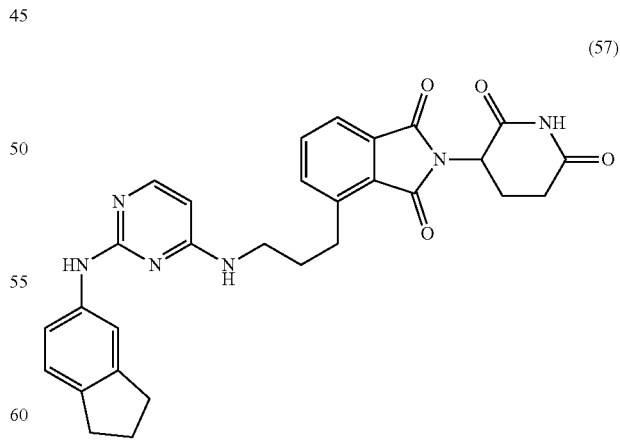

To a solution of 4-(3-((2-chloropyrimidin-4-yl)amino) propyl)-2-(2,6-dioxopiperidin-3-yl)isoindoline-1,3-dione (50 mg, 0.12 mmol) and 2,3-dihydro-1H-inden-5-amine (16 mg, 0.12 mmol) in $^t$BuOH (2 mL) was added TFA (18 μL, 0.24 mmol), then the mixture was stirred at 100° C. overnight. The mixture was concentrated in vacuo and purified by prep-HPLC to provide compound 57 (13.3 mg, 17%).

¹H NMR (500 MHz, DMSO-d₆) δ 11.12 (s, 1H), 10.42 (s, 1H), 9.05 (t, J=5.6 Hz, 1H), 7.82 (d, J=7.6 Hz, 1H), 7.79-7.65 (m, 3H), 7.39 (s, 1H), 7.27-7.15 (m, 2H), 6.19 (d, J=7.2 Hz, 1H), 5.14 (dd, J=12.9, 5.4 Hz, 1H), 3.39 (q, J=6.4 Hz, 2H), 2.94-2.88 (m, 1H), 2.84 (qd, J=7.4, 2.8 Hz, 8H), 2.65-2.56 (m, 1H), 1.99 (dq, J=29.1, 7.4 Hz, 6H).

LCMS (m/z): 525 [M+H]⁺.

Example 56: Synthesis of 2-(2,6-dioxopiperidin-3-yl)-4-(3-((2-(mesitylamino)pyrimidin-4-yl)amino)propyl)isoindoline-1,3-dione (58)

To a solution of 4-(3-((2-chloropyrimidin-4-yl)amino)propyl)-2-(2,6-dioxopiperidin-3-yl)isoindoline-1,3-dione (50 mg, 0.12 mmol) and 2,4,6-trimethylaniline (16 mg, 0.12 mmol) in ᵗBuOH (2 mL) was added TFA (18 μL, 0.24 mmol), then the mixture was stirred at 100° C. overnight. The mixture was concentrated and purified by prep-HPLC to provide compound 58 (6.3 mg, 8%).

LCMS (m/z): 527 [M+H]⁺.

Example 57: Synthesis of 4-(6-((2-((2,3-dihydro-1H-inden-5-yl)amino)pyrimidin-4-yl)amino)hexyl)-2-(2,6-dioxopiperidin-3-yl)isoindoline-1,3-dione (59)

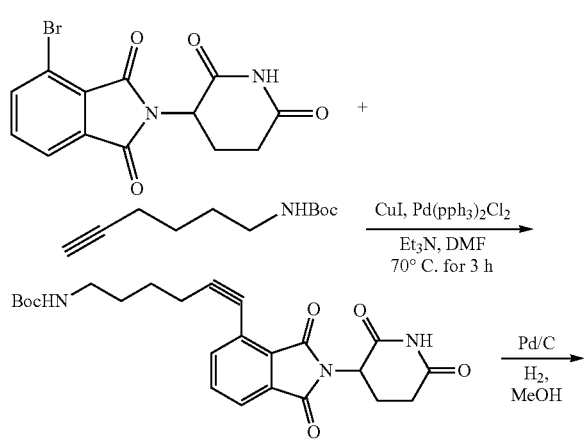

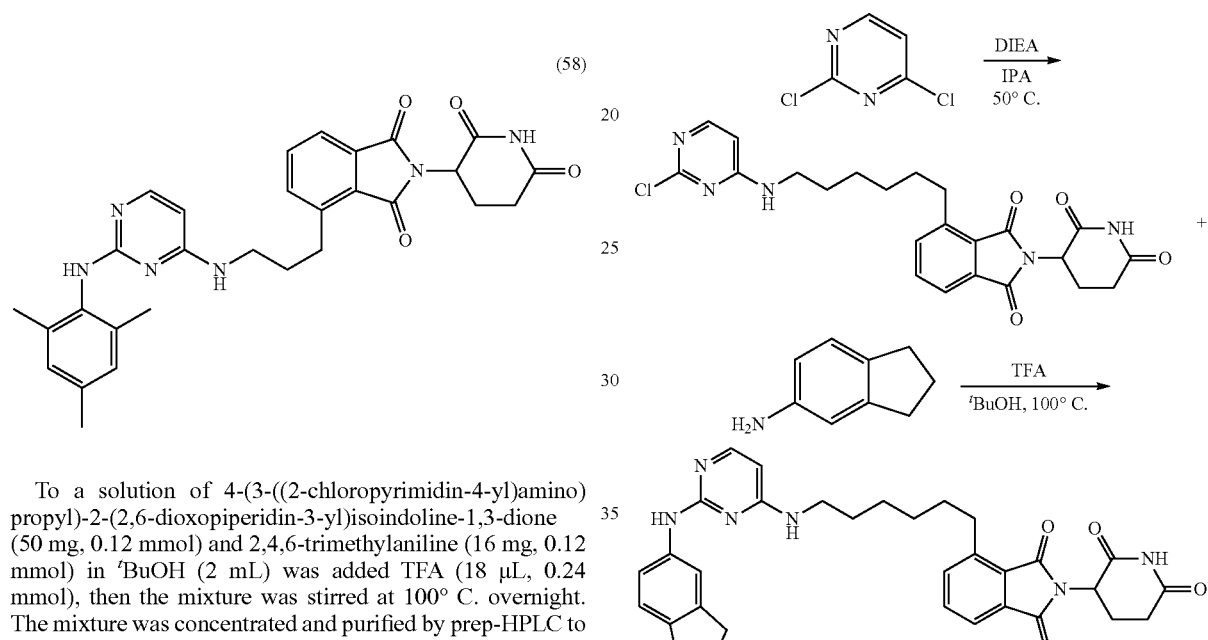

tert-Butyl (6-(2-(2,6-dioxopiperidin-3-yl)-1,3-dioxoisoindolin-4-yl)hex-5-yn-1-yl)carbamate To a solution of 4-bromo-2-(2,6-dioxopiperidin-3-yl)isoindoline-1,3-dione (672 mg, 2 mmol) and tert-butyl hex-5-yn-1-ylcarbamate (788 mg, 4 mmol) in DMF (10 mL) were added CuI (76 mg, 0.4 mmol), Et₃N (5 mL) and Pd(PPh₃)₂Cl₂ (140 mg, 0.2 mmol). The resulting mixture was then heated up to 70° C. and stirred under N₂ atmosphere for 3h. The mixture was then filtered, concentrated in vacuo, and purified by silica gel (MeOH/DCM=0-6%) to provide the title compound.

LCMS (m/z): 454 [M+H]⁺.

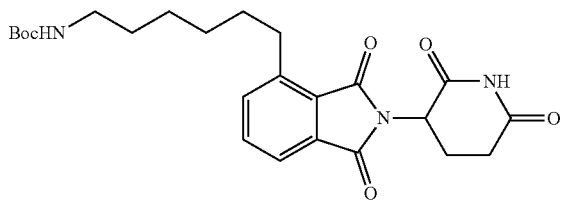 [SMILES: CC(C)(C)OC(=O)NCCCCCCc1cccc2c1C(=O)N(C1CCC(=O)NC1=O)C2=O]

tert-Butyl (6-(2-(2,6-dioxopiperidin-3-yl)-1,3-di-oxoisoindolin-4-yl)hexyl)carbamate To a solution of tert-butyl (6-(2-(2,6-dioxopiperidin-3-yl)-1,3-dioxoisoindolin-4-yl)hex-5-yn-1-yl)carbamate in MeOH was added Pd/C (10 wt. % loading, matrix carbon), then the mixture was hydrogenated at room temperature overnight. The reaction mixture was filtered and the filtrate was concentrated in vacuo to provide the title compound.

LCMS (m/z): 458 [M+H]$^+$.

4-(6-Aminohexyl)-2-(2,6-dioxopiperidin-3-yl)isoin-doline-1,3-dione

A solution of tert-Butyl (6-(2-(2,6-dioxopiperidin-3-yl)-1,3-dioxoisoindolin-4-yl)hexyl)carbamate in TFA/DCM=1/2 (v/v) was stirred at room temperature for 3h, and then concentrated in vacuo. The crude title compound was used in the next step without any purification.

LCMS (m/z): 358 [M+H]$^+$.

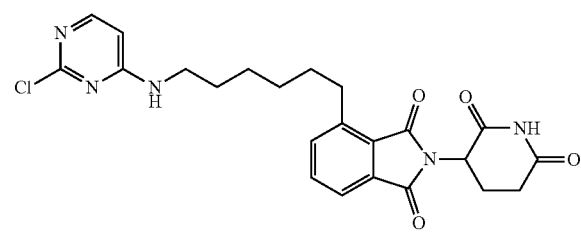 [SMILES: O=C1CCC(N2C(=O)c3cccc(CCCCCCNc4ccnc(Cl)n4)c3C2=O)C(=O)N1]

4-(6-((2-Chloropyrimidin-4-yl)amino)hexyl)-2-(2,6-dioxopiperidin-3-yl)isoindoline-1,3-dione To a solution of 4-(6-aminohexyl)-2-(2,6-dioxopiperidin-3-yl)isoindoline-1,3-dione and 2,4-dichloropyrimidine (1 eq) in isopropanol was added DIEA (3 eq), and then the mixture was stirred at 50° C. for 3h. The mixture was then concentrated in vacuo, purified by silica gel (MeOH/DCM=0-10%) to provide the title compound (120 mg).

LCMS (m/z): 470 [M+H]$^+$.

(59)

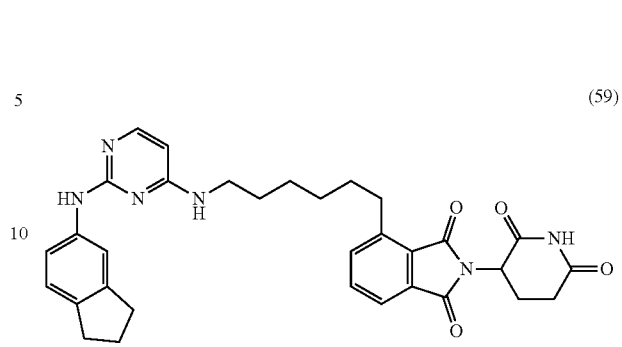

To a solution of 4-(6-((2-Chloropyrimidin-4-yl)amino)hexyl)-2-(2,6-dioxopiperidin-3-yl)isoindoline-1,3-dione (40 mg, 0.085 mmol) and 2,3-dihydro-1H-inden-5-amine (11 mg, 0.085 mmol) in $^t$BuOH (2 mL) was added TFA (13 µL, 0.17 mmol), then the mixture was stirred at 100° C. overnight. The mixture was concentrated in vacuo and purified by prep-HPLC to provide compound 59 (3.2 mg, 6%).

$^1$H NMR (500 MHz, DMSO-d$_6$) δ 11.12 (d, J=3.5 Hz, 1H), 8.83 (s, 1H), 7.97-7.62 (m, 5H), 7.42 (s, 1H), 7.08-6.99 (m, 1H), 6.65-6.57 (m, 1H), 5.94-5.85 (m, 1H), 5.22-5.06 (m, 1H), 2.90 (ddd, J=16.9, 13.8, 5.4 Hz, 1H), 2.77 (td, J=15.8, 13.9, 7.2 Hz, 4H), 2.61 (d, J=19.1 Hz, 1H), 2.34 (dt, J=46.4, 7.0 Hz, 2H), 2.13-2.03 (m, 1H), 2.03-1.90 (m, 2H), 1.69-1.49 (m, 4H), 1.38 (d, J=18.4 Hz, 2H).

LCMS (m/z): 567 [M+H]$^+$.

Example 58: Synthesis of 4-(6-((2-((9H-fluoren-2-yl)amino)pyrimidin-4-yl)amino)hexyl)-2-(2,6-di-oxopiperidin-3-yl)isoindoline-1,3-dione (60)

(60)

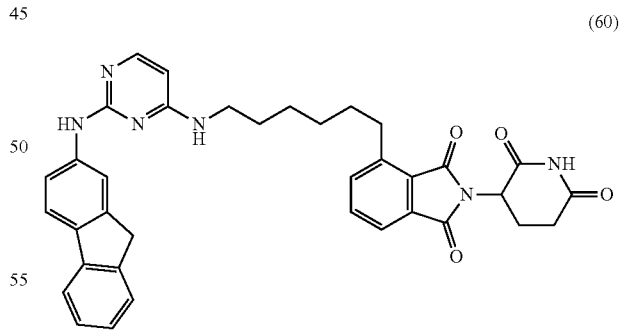

To a solution of 4-(6-aminohexyl)-2-(2,6-dioxopiperidin-3-yl)isoindoline-1,3-dione and 2,4-dichloropyrimidin (40 mg, 0.085 mmol) and 9H-fluoren-3-amine (15 mg, 0.085 mmol) in $^t$BuOH (2 mL) was added TFA (13 µL, 0.17 mmol), then the mixture was stirred at 100° C. overnight. The mixture was concentrated in vacuo and purified by prep-HPLC to provide compound 60. (5.6 mg, 9%).

LCMS (m/z): 615 [M+H]$^+$.

Example 59: Synthesis of 2-(2,6-dioxopiperidin-3-yl)-4-(6-((2-(4-(3-(trifluoromethyl)phenyl)piperazin-1-yl)pyrimidin-4-yl)amino)hexyl)isoindoline-1,3-dione (61)

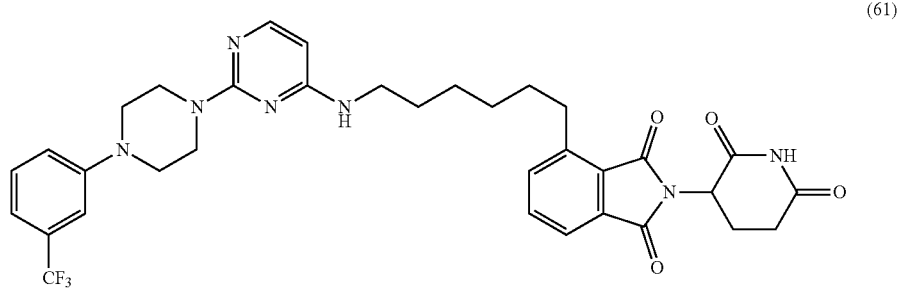 [SMILES: O=C1CCC(N2C(=O)c3cccc(CCCCCCNc4ccnc(N5CCN(c6cccc(C(F)(F)F)c6)CC5)n4)c3C2=O)C(=O)N1]

(61)

To a solution of 4-(6-aminohexyl)-2-(2,6-dioxopiperidin-3-yl)isoindoline-1,3-dione and 2,4-dichloropyrimidin (40 mg, 0.085 mmol) and 1-(3-(trifluoromethyl)phenyl)piperazine (19 mg, 0.085 mmol) in $^t$BuOH (2 mL) was added TFA (13 µL, 0.17 mmol), then the mixture was stirred at 100° C. overnight. The mixture was concentrated in vacuo and purified by prep-HPLC to provide compound 61 (5.5 mg, 8%).

$^1$H NMR (500 MHz, DMSO-$d_6$) δ 11.30-10.99 (m, 1H), 8.84 (s, 1H), 8.00-7.75 (m, 3H), 7.70 (td, J=6.7, 2.4 Hz, 1H), 7.48-7.40 (m, 1H), 7.22 (s, 1H), 7.10 (d, J=3.4 Hz, 1H), 6.68-6.60 (m, 1H), 6.18-6.07 (m, 1H), 5.14 (ddd, J=13.2, 5.2, 3.3 Hz, 1H), 3.85 (d, J=5.6 Hz, 4H), 3.48 (s, 4H), 2.98-2.85 (m, 1H), 2.67-2.55 (m, 1H), 2.31 (q, J=6.9 Hz, 1H), 2.05 (dt, J=11.6, 5.0 Hz, 1H), 1.71-1.49 (m, 4H), 1.24 (s, 4H).

LCMS (m/z): 664 [M+H]$^+$.

Example of 60: Synthesis of 3-(5-(((5-chloro-4-((2-(isopropylsulfonyl)phenyl)amino)pyrimidin-2-yl)amino)methyl)-1-oxoisoindolin-2-yl)piperidine-2,6-dione (41)

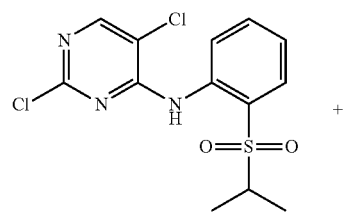

+

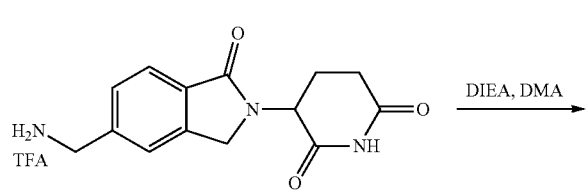

DIEA, DMA

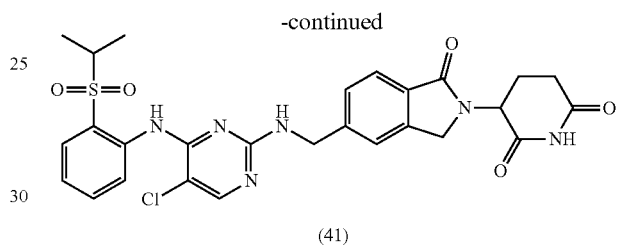

(41)

To a solution of 2,5-dichloro-N-(2-(isopropylsulfonyl)phenyl)pyrimidin-4-amine (67 mg, 0.19 mmol) and 3-(5-(aminomethyl)-1-oxoisoindolin-2-yl)piperidine-2,6-dione TFA (50 mg, 0.13 mmol) in DMA (2 mL), DIEA (67 mg, 0.52 mmol) was added at room temperature. The reaction mixture was heated up to 130° C. overnight. The crude mixture was purified by HPLC to yield compound 41 (18 mg, 0.031 mmol, 24%).

$^1$H NMR (500 MHz, DMSO-$d_6$) δ 10.98 (s, 1H), 9.50 (s, 1H), 8.30-7.93 (m, 3H), 7.90-7.54 (m, 3H), 7.50-7.27 (m, 3H), 5.09 (dd, J=13.3, 5.1 Hz, 1H), 4.54 (d, J=48.2 Hz, 2H), 4.42-4.16 (m, 2H), 3.39 (d, J=58.0 Hz, 1H), 2.90 (ddd, J=17.3, 13.6, 5.5 Hz, 1H), 2.59 (dd, J=17.1, 3.8 Hz, 1H), 2.37 (qd, J=13.2, 4.4 Hz, 1H), 1.14 (m, 6H).

LCMS (m/z): 583 [M+H]$^+$.

Example 61: Synthesis of 3-(4-((5-chloro-4-((2-(isopropylsulfonyl)phenyl)amino)pyrimidin-2-yl)amino)-1-oxoisoindolin-2-yl)piperidine-2,6-dione (42)

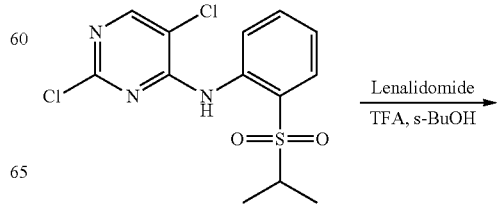

Lenalidomide
TFA, s-BuOH

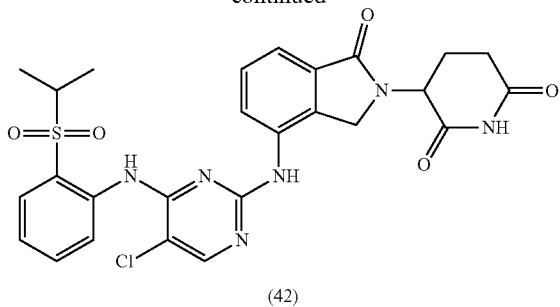

(42)

To a solution of 2,5-dichloro-N-(2-(isopropylsulfonyl) phenyl)pyrimidin-4-amine (67 mg, 0.19 mmol) and Lenalidomide (50 mg, 0.19 mmol) in s-BuOH (2 mL), TFA (33 mg, 0.29 mmol) was added at room temperature. The reaction mixture was heated up to 100° C. overnight. The crude mixture was purified by HPLC to yield compound 42 (21 mg, 0.037 mmol, 19%). (M+H)$^+$ calculated: 569.13, found 569.14.

$^1$H NMR (500 MHz, DMSO-d$_6$) δ 10.97 (s, 1H), 9.60 (s, 1H), 9.43 (s, 1H), 8.47 (d, J=8.4 Hz, 1H), 8.29 (s, 1H), 7.82 (td, J=7.7, 7.1, 2.1 Hz, 2H), 7.61-7.46 (m, 3H), 7.35-7.26 (m, 1H), 5.10 (dd, J=13.3, 5.1 Hz, 1H), 4.51-4.28 (m, 2H), 3.47 (p, J=6.8 Hz, 1H), 2.87 (ddd, J=17.3, 13.7, 5.4 Hz, 1H), 2.54 (d, J=4.0 Hz, 1H), 2.28 (qd, J=13.3, 4.5 Hz, 1H), 1.88-1.76 (m, 1H), 1.17 (dd, J=10.0, 6.8 Hz, 6H).

LCMS (m/z): 569 [M+H]$^+$.

Example 62: Lenalidomide Displacement Assay

Various inventive compounds were analyzed for cereblon binding. Compounds in an Atto565-Lenalidomide displacement assay were dispensed in a 384-well microplate (Corning, 4514) using D300e Digital Dispenser (HP) normalized to 1% DMSO into 10 nM Atto565-Leanlidomide, 100 nM DDB1AB-CRBN, 50 mM Tris pH 7.5, 200 mM NaCl, 0.1% Pluronic® F-68 solution (Sigma). Compound titrations were incubated for 60 min at room temperature. The change in fluorescence polarization was monitored using a PHERAstar® FS microplate reader (BMG Labtech) for 1 h in 120s cycles. Data from two independent replicates (n=2) was used to estimate IC$_{50}$ values using variable slope equation in GraphPad Prism 7. The Ki was calculated with probe Kd of 40 nM for the conditions described above following equations described in Nikolovska-Coleska et al., Analytical Biochemistry 332(2): 261-273 (2004) for competitive model using free concentrations.

The results, shown in IC$_{50}$ and Ki values, are set forth below in Table 1.

Example 63: Cellular CRBN dBET6 Displacement Assay

BRD4BD2 were subcloned into mammalian pcDNA5/FRT Vector (Ampicillin and Hygromycin B resistant) modified to contain MCS-eGFP-P2A-mCherry. Stable cell lines expressing eGFP-protein fusion and mCherry reporter were generated using the Flip-In™ 293 system. Plasmid (0.3 µg) and pOG44 (4.7 µg) DNA were preincubated in 100 µl of Opti-MEM I (Gibco™, Life Technologies™) media containing 0.05 mg/ml Lipofectamine® 2000 (Invitrogen™) for 20 minutes and added to Flip-In™ 293 cells containing 1.9 ml of DMEM media (Gibco™, Life Technologies™) per well in a 6-well plate format (Falcon®, 353046). Cells were propagated after 48 hours and transferred into a 10 cm2 plate (Corning, 430165) in DMEM media containing 50 µg/ml of Hygromycin B (REF 10687010, Invitrogen™) as a selection marker.

Following a 2-3 passage cycle, FACS (FACSAria™ II, BD) was used to enrich for cells expressing eGFP and mCherry.

Cells stably expressing BRD4BD2-GFP with mCherry reporter were seeded at 30-50% confluency in 96 well plates (3596, Costar) with 100 µl DMEM media containing 10% FBS per well a day before compound treatment. Compounds and 100 nM dBET6 were dispensed using D300e Digital Dispenser (HP) normalized to 0.5% DMSO and incubated with cells for 5 hours following trypsinization and resuspension in DMEM media, transferred into 96-well plates (353910, Falcon®) and analyzed by flow cytometer (guava easyCyte™ HT, Millipore™). Signal from minimal 3000 events per well was acquired and the eGFP and mCherry florescence monitored. Data was analyzed using FlowJo® (FlowJo®, LCC). Forward and side scatter outliers, frequently associated with cell debris, were removed leaving >90% of total cells, followed by removal of eGFP and mCherry signal outliers, leaving 88-90% of total cells creating the set used for quantification. The eGFP protein abundance relative to mCherry was then quantified as a ten-fold amplified ratio for each individual cell using the formula: 10×eGFP/mCherry. The median of the ratio was then calculated per set, normalized to the median of the DMSO ratio.

TABLE 1

Characterization of compounds with in vitro CRBN binding, CRBN-dependent proliferation, and cellular engagement assays.

| Compound | CRBN Binding IC$_{50}$ µM | CRBN Binding Ki µM | Cellular CRBN-BRD4 dBET6 displacement EC$_{50}$ µM |
|---|---|---|---|
| Lenalidomide | 5.19 | 1.49 | 0.82 |
| 1 | 29.7 | 8.5 | |
| 2 | 47.5 | 13.6 | 47.93 |
| 3 | 12.5 | 13.6 | |
| 4 | 8.5 | 2.4 | |
| 5 | 42.5 | 12.2 | |
| 6 | 22.9 | 6.5 | |
| 7 | 38.9 | 11.1 | |
| 8 | N | N | |
| 9 | 22.1 | 6.3 | |
| 10 | 18.9 | 5.4 | |
| 11 | 14.7 | 4.2 | |
| 12 | 13.8 | 3.9 | |
| 13 | 28.9 | 8.3 | |
| 14 | 1.6 | 0.44 | |
| 15 | 15.2 | 4.3 | |
| 16 | 0.517 | 0.13 | |
| 17 | 3.44 | 0.97 | |
| 18 | | | 2.694 |
| 19 | | | 3.63 |
| 20 | | | 1.264 |
| 21 | | | 2.311 |
| 22 | | | Not binding |
| 23 | | | 0.66 |
| 24 | | | 1.347 |
| 25 | | | |
| 26 | | | 0.67 |
| 27 | | | 1.246 |
| 28 | | | 3.247 |
| 29 | | | 8.138 |
| 30 | | | 8.146 |
| 31 | | | 8.66 |
| 32 | | | 4.164 |

TABLE 1-continued

Characterization of compounds with in vitro CRBN binding, CRBN-dependent proliferation, and cellular engagement assays.

| Compound | CRBN Binding IC$_{50}$ µM | CRBN Binding Ki µM | Cellular CRBN-BRD4 dBET6 displacement EC$_{50}$ µM |
|---|---|---|---|
| 33 | | | 2.594 |
| 34 | | | Not binding |
| 35 | | | 1.86 |
| 36 | | | 2.24 |
| 37 | | | 9.737 |
| 38 | | | 2.604 |
| 39 | | | 0.742 |
| 40 | | | Not binding |
| 41 | | | |
| 42 | | | |
| 43 | | | 25.27 |
| 44 | | | 0.913 |
| 45 | | | 2.06 |
| 46 | | | 1.127 |
| 47 | | | 27.07 |
| 48 | | | 12.45 |
| 49 | | | 12.42 |
| 50 | | | 8.29 |
| 51 | | | 6.83 |
| 52 | | | 0.46 |
| 53 | | | 0.665 |

As shown in Table 1, compounds 1-17 that share the same amine based linkage to the lenalidomide moiety bound CRBN in vitro with the K$_i$ in the range of 13 to 0.13 µM. Compound 14 and 16 and 17 showed affinity that exceeds that of lenalidomide (K$_i$ 1.49 µM).

These molecules were further assessed in a cellular CRBN engagement assay, which relies on displacement of CRBN-based degrader molecule dBET6 from CRBN by a competing ligand, hence a rescue in degradation of second bromodomain of BRD4. This assay provided a readout of cellular CRBN binding impacted by the permeability of the molecule tested. Data is shown in Table 1.

As indicated in the Table 1, cellular CRBN engagement varied from inactive compounds (compounds 22, 34, 40) to compounds with EC$_{50}$ exceeding that of FDA approved lenalidomide (EC$_{50}$ of 0.82 µM) for compounds 23, 26, 39, 52 with EC$_{50}$ of 0.66, 0.67, 0.742, 0.46 µM, respectively. The same pyrimidine-based attachment of IMiD core is shared by the most potent compounds, compounds 23, 26, 39 and 52. The remaining compounds tested in this assay showed good to moderate cellular CRBN engagement as compared to that of lenalidomide.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound of Formula (Ia1) or Formula (Ib1):

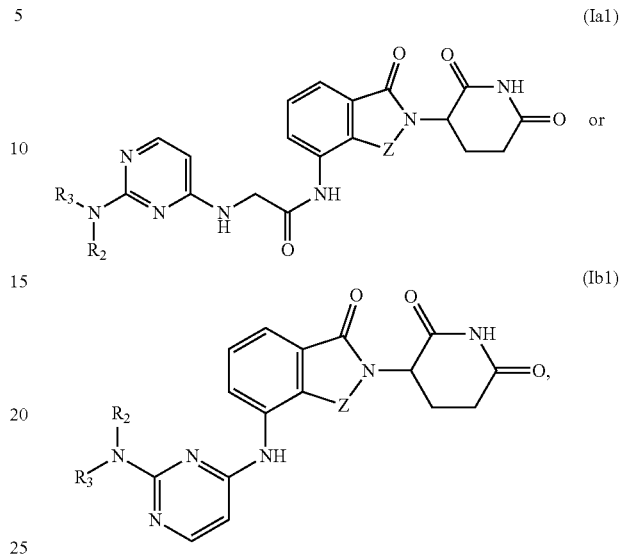

wherein:
Z represents CH$_2$;
R$_2$ is H or C1-C2 alkyl; and
R$_3$ is optionally substituted C1-C5 alkyl, optionally substituted C6-C14 aryl, optionally substituted C6-C14 heteroaryl, optionally substituted C5-C14 carbocyclic or optionally substituted C5-C14 heterocyclic, or R2 and R3 together with the N to which they are bound form an optionally substituted C6-C14 heterocyclic group or an optionally substituted C6-C14 heteroaryl group;
or a pharmaceutically acceptable salt or stereoisomer thereof.

2. The compound of claim 1, wherein R$_3$ represents C6-C14 aryl or substituted C6-C14 aryl, or the compound of formula (Ia1) has a structure represented by formula (Ia1a):

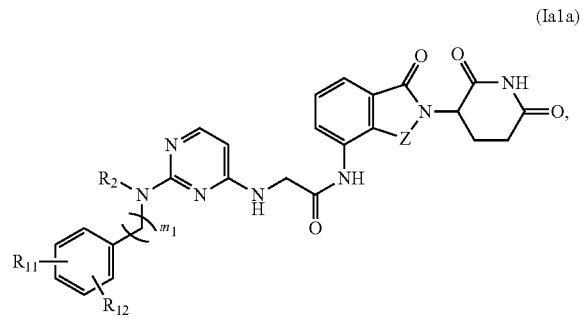

wherein:
m$_1$ is 0 or 1; and
R$_{11}$ and R$_{12}$ are each independently H, halo, CF$_3$, or C1-C2 alkoxy, or
R$_{11}$ and R$_{12}$ are each independently C or a heteroatom and together with the atoms to which they are bound form an optionally substituted C5-C7 carbocyclic, optionally substituted C5-C7 heterocyclic, optionally substituted C6-aryl or optionally substituted C6-heteroaryl group, or a pharmaceutically acceptable salt or stereoisomer thereof.

3. The compound of claim 1, wherein $R_2$ and $R_3$ together with the atoms to which they are bound form an optionally substituted C6-C14 heterocyclic, and the compound of formula (Ia1) has a structure represented by formula (Ia1c):

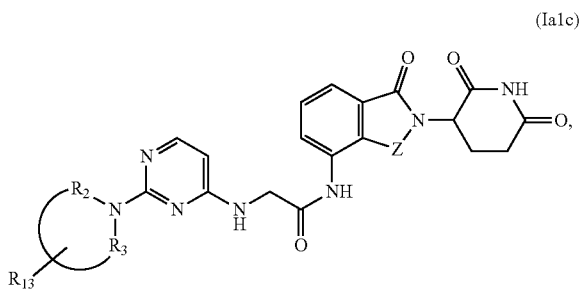

(Ia1c)

wherein:
$R_{13}$ is H or optionally substituted C1-C5 alkyl, optionally substituted C6-C14 aryl, optionally substituted C6-C14 heteroaryl, optionally substituted C5-C14 carbocyclic, or optionally substituted C5-C14 heterocyclic,
or a pharmaceutically acceptable salt or stereoisomer thereof.

4. The compound of claim 1, wherein R3 is an optionally substituted C6-C14 aryl, or the compound of formula (Ib1) has a structure represented by formula (Ib1a):

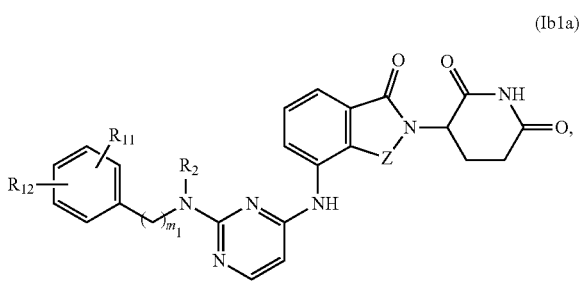

(Ib1a)

wherein:
$m_1$ is 0 or 1,
$R_{11}$ and $R_{12}$ are independently H, halo, $CF_3$, or C1-C2 alkoxy, or wherein $R_{11}$ and $R_{12}$ each independently represent C or a heteroatom and together with the atoms to which they are bound form an optionally substituted C5-C10 carbocyclic, optionally substituted C5-C10 heterocyclic, optionally substituted C6-C10 aryl, or optionally substituted C6-C10 heteroaryl,
or a pharmaceutically acceptable salt or stereoisomer thereof.

5. The compound of claim 1, wherein $R_2$ and $R_3$ together with the atoms to which they are bound form an optionally substituted C6-C14 heterocyclic group, and the compound of formula (Ib1) has a structure represented by formula (Ib1c):

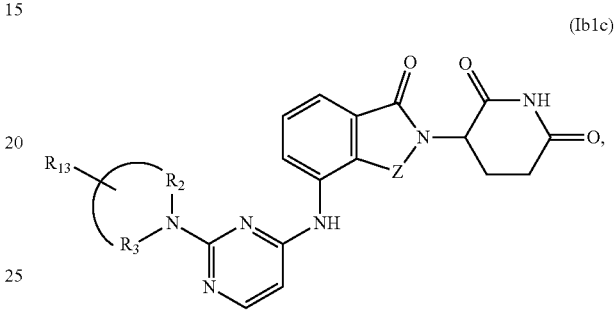

(Ib1c)

wherein:
$R_{13}$ is H or optionally substituted C1-C5 alkyl, optionally substituted C6-C14 aryl, optionally substituted C6-C14 heteroaryl, optionally substituted C5-C14 carbocyclic, or optionally substituted C5-C14 heterocyclic,
or a pharmaceutically acceptable salt or stereoisomer thereof.

6. The compound of claim 1, wherein $R_3$ represents an optionally substituted C6-C14 aryl or an optionally substituted C6-C14 heteroaryl group.

7. The compound of claim 1, wherein $R_3$ represents an optionally substituted C5-C14 carbocyclic or an optionally substituted C5-C14 heterocyclic group.

8. The compound of claim 1, wherein $R_3$ is an optionally substituted a C6-C14 aryl group or a substituted C6-C14 heteroaryl group.

9. The compound of claim 8, wherein $R_3$ is an optionally substituted phenyl group.

10. A compound which is selected from the group consisting of:

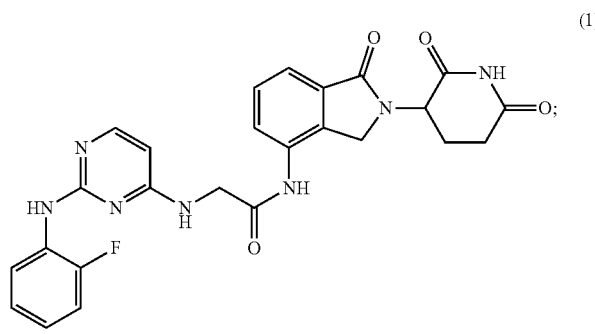

(1)

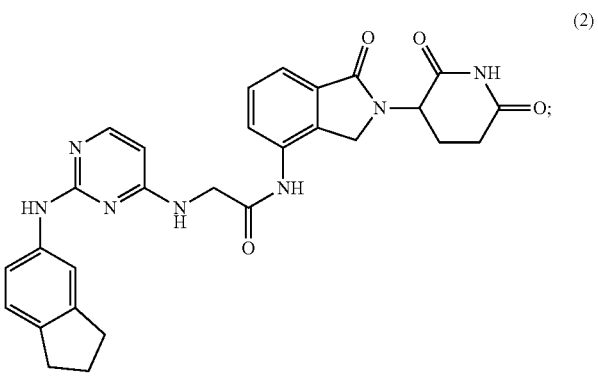

(2)

-continued
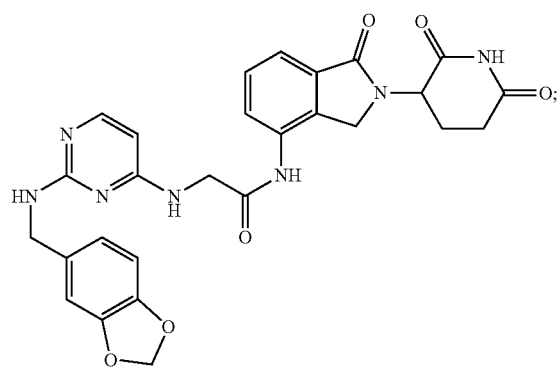
(3)
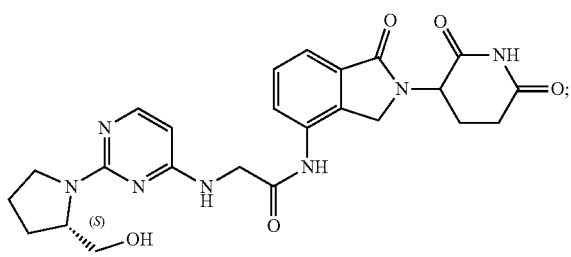
(4)
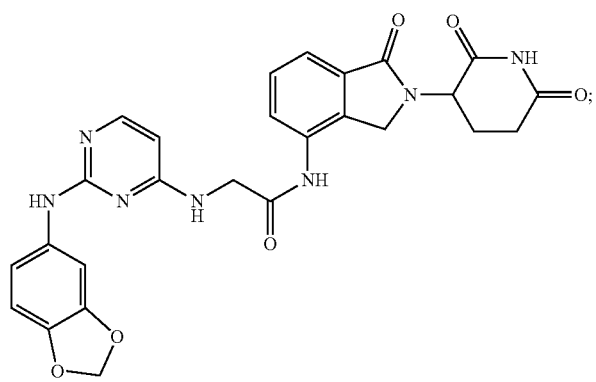
(5)
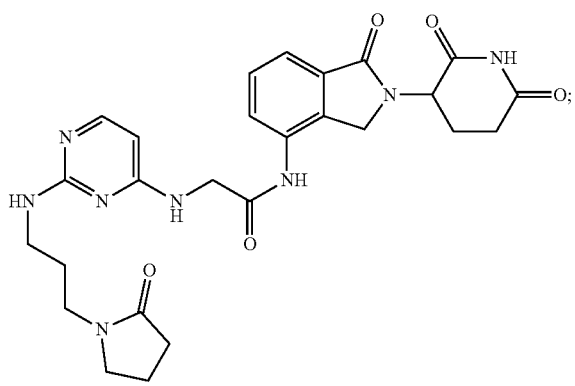
(6)
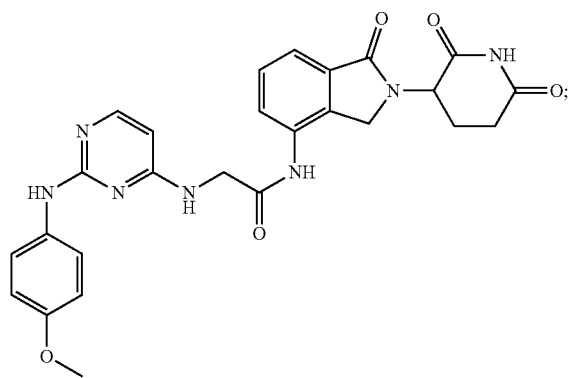
(7)
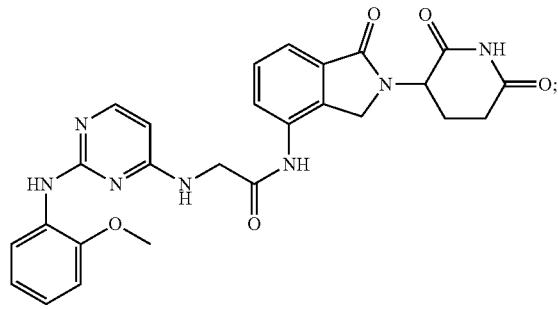
(15)
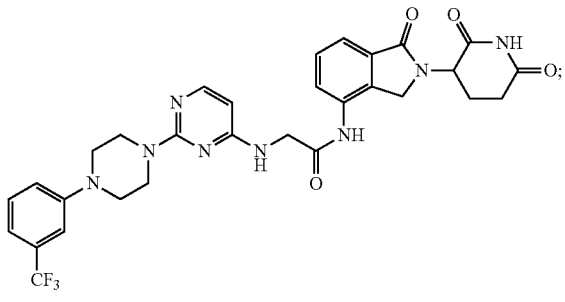
(16)

-continued
(17)
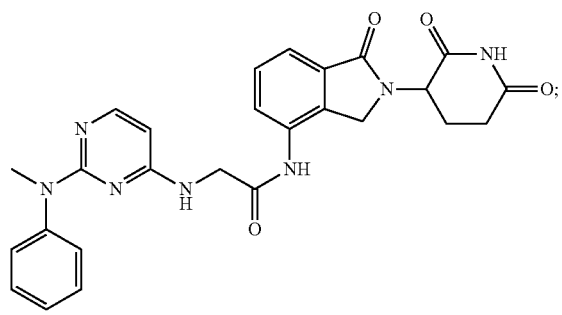
(18)
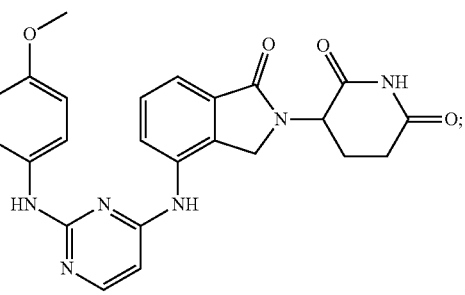
(19)
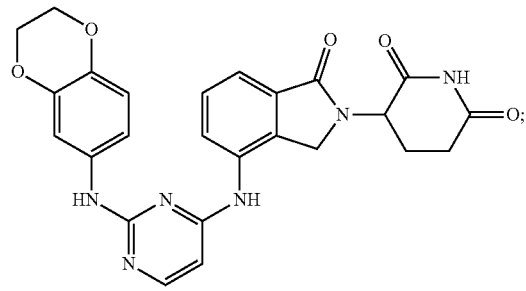
(21)
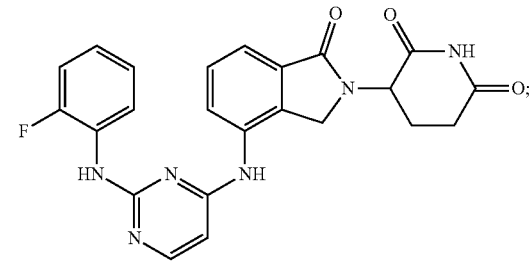
(23)
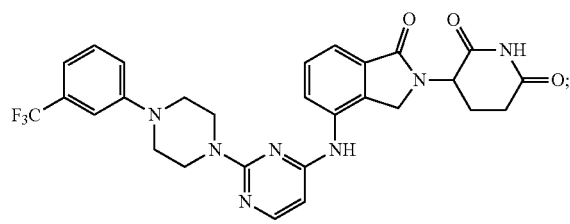
(24)
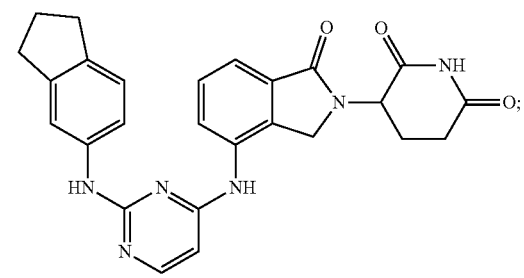
(25)
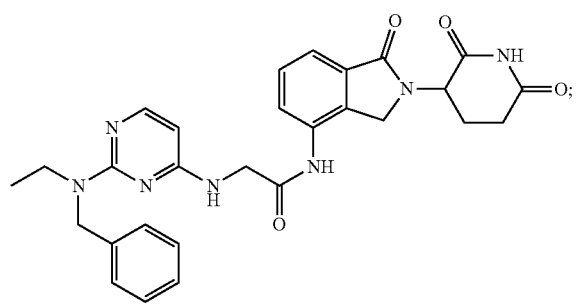
(26)
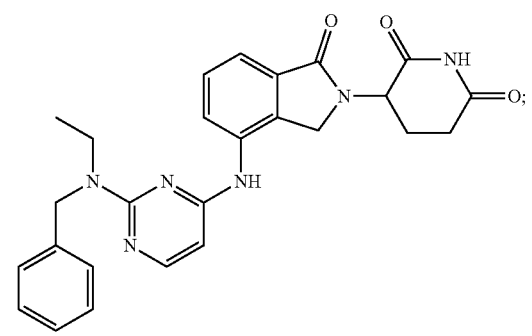
(27)
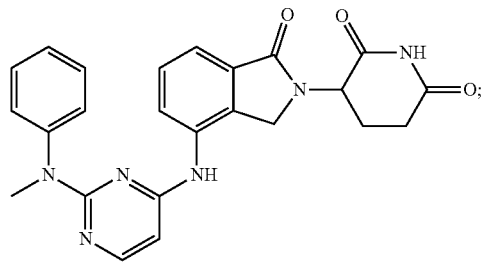
(28)
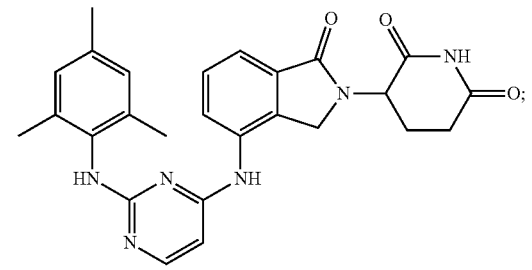

-continued
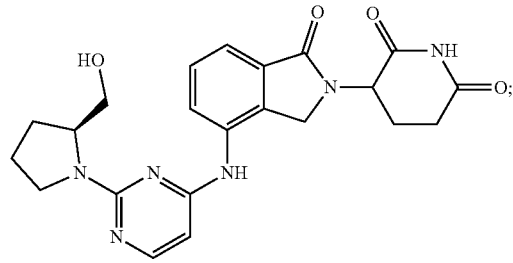
(29)
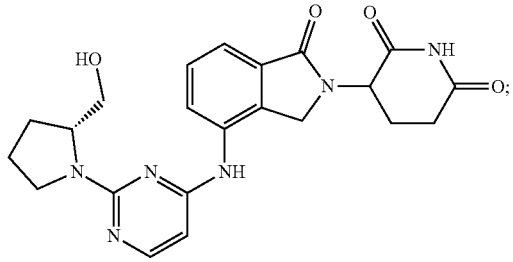
(30)
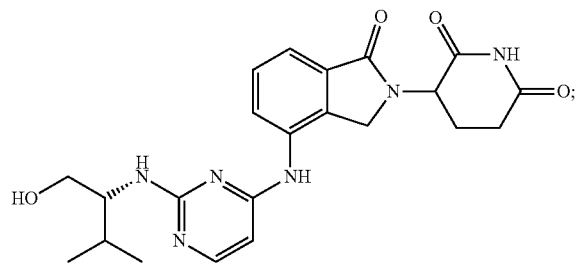
(37)
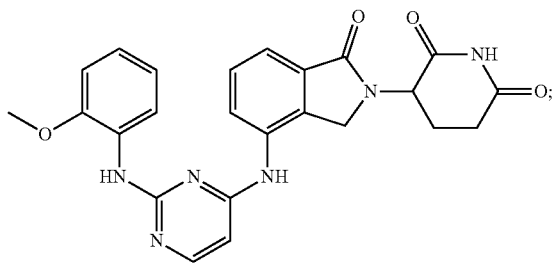
(38)
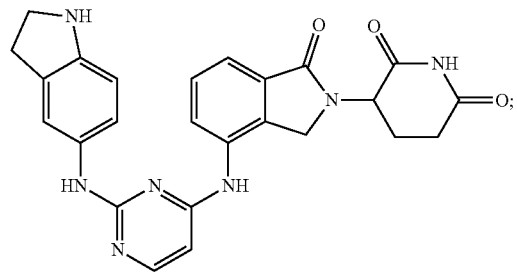
(43)
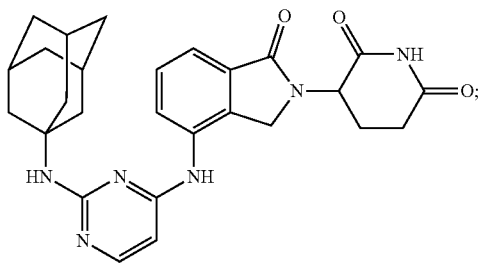
(44)
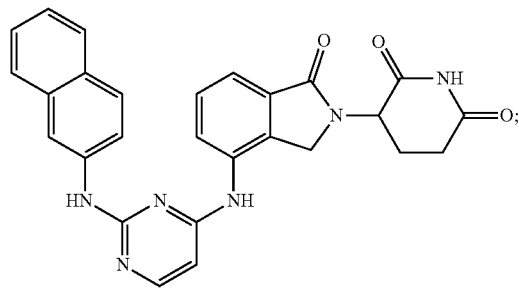
(45)
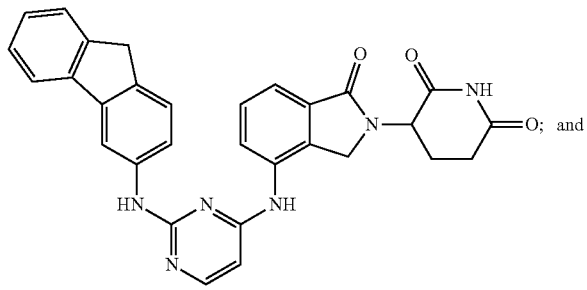
(46); and
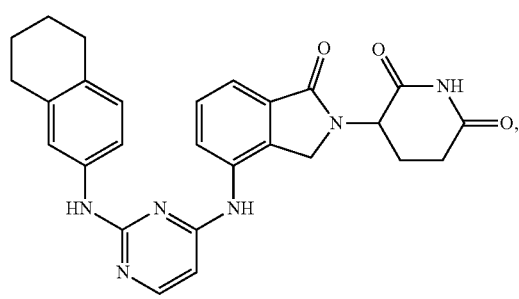
(52)

or a pharmaceutically acceptable salt or stereoisomer thereof.

11. A pharmaceutical composition comprising a therapeutically effective amount of the compound of claim 1, or a pharmaceutically acceptable salt or stereoisomer thereof, and a pharmaceutically acceptable carrier.

12. The pharmaceutically composition of claim 11, which is in the form of a capsule or tablet.

13. The pharmaceutical composition of claim 11, which is a solution or suspension.

14. A method of treating a cancer characterized or mediated by aberrant activity of a protein selected from the group consisting of casein kinase 1 alpha (CK1α), family with sequence similarity 83 member F (FAM83F), DTW domain containing 1 (DTWD1), zinc finger protein 91 homolog (ZFP91), ZFP62, ZFP36 ring finger protein like (ZFP36L2), ring finger protein 166 (RNF166), Ikaros family zinc finger protein 1 (IKZF1), IKZF2, IKZF3, IKZF4, IKZF5, Ras-related protein Rab-28 (RAB28), glutathione S-transferase pi 1 (GSTPI), GSPT2, mitochondrial import inner membrane translocase subunit Tim10 (TIMM10), GDNF inducible zinc finger protein I (GZFI), early growth response 1 (EGR1), hypermethylated in cancer 1 (HIC 1), HIC2, insulinoma-associated protein 2 (INSM2), odd-skipped related transcription factor 2 (OSR2), protein polybromo-1 (PB1), PR domain zinc finger protein 15 (PRD15), spalt like transcription factor 1 (SALL1), SALL3, SALL4, WIZ, zinc finger and BTB domain-containing protein 17 (ZBT17), ZBT41, ZBT49, ZBT7A, ZBT7B, ZBTB2, ZBTB39, zinc finger protein interacting with K protein 1 (ZIK1), zinc finger protein 3 (ZNF3), ZNF217, ZNF276, ZNF316, ZNF324B, ZNF335, ZNF397, ZNF407, ZNF408, ZNF462, ZNF483, SNF517, ZNF526, ZNF581, ZNF587, ZNF589, ZNF618, ZNF644, ZNF646, ZNF653, ZNF654, ZNF692, ZNF724, ZNF771, ZNF782, ZNF784, ZNF814, zinc finger and SCAN domain containing 10 (ZSC10), ZSC22, ZC827, and zinc finger with UFMI-specific peptidase domain (ZUFSP), comprising administering a therapeutically effective amount of the compound of claim 1, or a pharmaceutically acceptable salt or stereoisomer thereof, to a subject in need thereof.

15. The method of claim 14, wherein the cancer is a hematological cancer selected from leukemia, lymphoma, and multiple myeloma.

16. The method of claim 15, wherein the cancer is multiple myeloma.

* * * * *